United States Patent
Vandyck et al.

(10) Patent No.: US 9,433,609 B2
(45) Date of Patent: Sep. 6, 2016

(54) BENZIMIDAZOLE-IMIDAZOLE DERIVATIVES

(71) Applicant: Janssen Sciences Ireland UC, Little Island, Co. Cork (IE)

(72) Inventors: Koen Vandyck, Paal-Beringen (BE); Stefaan Julien Last, Lint (BE); Ioannis Nicolaos Houpis, Antwerp (BE); Pierre Jean-Marie Bernard Raboisson, Rosieres (BE)

(73) Assignee: Janssen Sciences Ireland UC, Little Island, Co. Cork (IE)

( * ) Notice: Subject to any disclaimer, the term of this patent is extended or adjusted under 35 U.S.C. 154(b) by 0 days.

(21) Appl. No.: 13/836,816

(22) Filed: Mar. 15, 2013

(65) Prior Publication Data

US 2014/0107172 A1    Apr. 17, 2014

Related U.S. Application Data

(62) Division of application No. 13/508,186, filed as application No. PCT/EP2010/066668 on Nov. 3, 2010.

(30) Foreign Application Priority Data

Nov. 4, 2009  (EP) ..................................... 09175015
Feb. 24, 2010 (EP) ..................................... 10154583

(51) Int. Cl.
| | | |
|---|---|---|
| A61K 31/40 | (2006.01) | |
| A61K 31/41 | (2006.01) | |
| A61K 31/4164 | (2006.01) | |
| A61K 31/4184 | (2006.01) | |
| C07D 403/14 | (2006.01) | |
| A61K 45/06 | (2006.01) | |
| C07D 405/14 | (2006.01) | |

(52) U.S. Cl.
CPC ........... *A61K 31/4184* (2013.01); *A61K 31/40* (2013.01); *A61K 31/41* (2013.01); *A61K 31/4164* (2013.01); *A61K 45/06* (2013.01); *C07D 403/14* (2013.01); *C07D 405/14* (2013.01)

(58) Field of Classification Search
CPC .. A61K 31/41; A61K 31/4164; A61K 31/40; A61K 31/4184
USPC .......................................................... 514/387
See application file for complete search history.

(56) References Cited

U.S. PATENT DOCUMENTS

| | | |
|---|---|---|
| 5,807,876 A | 9/1998 | Armistead et al. |
| 6,054,472 A | 4/2000 | Armistead et al. |
| 6,344,465 B1 | 2/2002 | Armistead et al. |
| 6,498,178 B2 | 12/2002 | Stamos et al. |
| 8,101,643 B2 | 1/2012 | Qiu et al. |
| 8,618,151 B2* | 12/2013 | Li ......................... C07D 403/14 514/394 |
| 2009/0202483 A1 | 8/2009 | Bachand et al. |

FOREIGN PATENT DOCUMENTS

| | | |
|---|---|---|
| WO | WO97/40028 A | 10/1997 |
| WO | WO98/40381 A | 9/1998 |
| WO | WO00/56331 A | 9/2000 |
| WO | WO02/18369 A | 3/2002 |
| WO | WO2004/050035 A | 6/2004 |
| WO | WO2006/133326 A | 12/2006 |
| WO | WO2008/021927 A | 2/2008 |
| WO | WO2008/021928 A | 2/2008 |
| WO | WO2008/048589 A | 4/2008 |
| WO | WO2008/070447 A | 6/2008 |
| WO | WO2009/102318 A | 8/2009 |
| WO | WO2009/102325 A | 8/2009 |
| WO | WO2010/065668 A | 6/2010 |
| WO | WO2010/065674 A | 6/2010 |
| WO | WO2010/065681 A | 6/2010 |
| WO | WO2010/096302 | 8/2010 |
| WO | WO2010/099527 A | 9/2010 |
| WO | WO2010/132601 | 11/2010 |

OTHER PUBLICATIONS

Hirokazu Awano, et al., "Synthesis and Antiviral Activity of 5-Substituted (2's)-2'-Deoxy-2'-C-Methylcytidines and -uridines", Arch. Pharm. Pharm. Med. Chem., 329, 1996, pp. 66-72.

L. W. Brox, et al., "Studies on the Growth Inhibition and Metabolism of 2'-Deoxy-2'-fluorocytidine in Cultured Human Lymphoblasts", Cancer Research, vol. 34., 1974, pp. 1838-1842.

(Continued)

*Primary Examiner* — Yong Chong
(74) *Attorney, Agent, or Firm* — Baker & Hostetler LLP

(57) ABSTRACT

Inhibitors of HCV replication of formula I

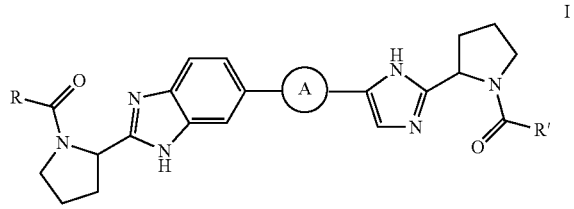

including stereochemically isomeric forms, and salts, solvates thereof, wherein R and R' are, each independently, —CR₁R₂R₃, aryl, heteroaryl or heteroC$_{4-6}$cycloalkyl, whereby aryl and heteroaryl may optionally be substituted with 1 or 2 substituents selected from halo and methyl.

The present invention also relates to processes for preparing said compounds, pharmaceutical compositions containing them and their use in HCV therapy.

10 Claims, No Drawings

(56) References Cited

OTHER PUBLICATIONS

M. A. Ivanov, et al., "Synthesis and Biological Properties of Pyrimidine 4'-Fluoronucleosides and 4'-Fluorouridine 5'-O-Triphosphate", Russian Journal of Bioorganic Chemistry, vol. 36, No. 4, 2010, pp. 488-496.

Lars Petter Jordheim, et al., "Advances in the Development of Nucleoside and Nucleotide Analogues for Cancer and Viral Diseases", Nature Reviews, Drug Discovery, vol. 12, 2013, pp. 447-464.

Klaus Klumpp, et al., "2'-Deoxy-4'-azido Nucleoside Analogs Are Highly Potent Inhibitors of Hepatitis C Virus Replication Despite the Lack of 2'-α-Hydroxyl Groups", The Journal of Biological Chemistry, vol. 283, No. 4, 2008, pp. 2167-2175.

Peng Liu, et al., "Fluorinated Nucleosides: Synthesis and Biological Implication", J Fluor Chem., 129 (9), 2008, pp. 743-766.

Akira Matsuda, et al., Radical Deoxygenation of *Tert*-Alcohols in 2'-Branched-Chain Sugar Pyrimidine Nucleosides: Synthesis and Antileukemic Activity of 2'-Deoxy-2' (S)-Methylcytidine[1], Chem. Pharm. Bull., vol. 35, No. 9, 1987, pp. 3967-3970.

Eisuke Murakami, et al., "Mechanism of Activation of β-D-2'-Deoxy-2'-Fluoro-2'-C-Methylcytidine and Inhibition of Hepatitis C Virus NS5B RNA Polymerase", Antimicrobial Agents and Chemotherapy, vol. 51, No. 2, 2007, pp. 503-509.

Michael J. Sofia, et al., "Discovery of a β-D-2'-Deoxy-2'-α-fluoro-2'-β-C-methyluridine Nucleotide Prodrug (PSI-7977) for the Treatment of Hepatitis C Virus", Journal of Medicinal Chemistry, vol. 53, No. 2010, pp. 7202-7218.

Michael J. Sofia, et al., "Nucleoside, Nucleotide, and Non-Nucleoside Inhibitors of Hepatitis C Virus NS5B RNA-Dependent RNA-Polymerase", Journal of Medicinal Chemistry, vol. 55, 2012, pp. 2481-2531.

Bodanszky, *Peptide Chemistry*, 2nd rev. ed., Springer-Verlag, Berlin, Germany (1993).

Krieger et al, "Enhancement of Heptatitis C Virus RNA Replication by Cell Culture-Adaptive Mutations", *Journal of Virology* (2001) 75:4614-4624.

Li et al, "Indentification of 1-isopropylsulfonyl-2-amine benzimidazoles as a new class of inhibitors of hepatitis B virus", *European Journal of Medicinal Chemistry* (2007) 42(11-12):1358-1364.

Lohmann et al, "Viral and cellular determinants of hepatitis C virus RNA replication in cell culture", *Journal of Virology* (2003) 77:3007-3019.

Lohmann et al, "Identification of 1-isopropylsulfonyl-2-amine benzimidazoles as a new class of inhibitors of hepatitis B virus", *Science* (1999) 285:110-113.

Yi et al, "Adaptive mutations producing efficient replication of geneotype 1a hepatitis C virus RNA in normal Huh7 cells", *Journal of Virology* (2004) 78:7904-7915.

Japanese Office Action, Patent Application JP-2012-537376, Jan. 29, 2015.

* cited by examiner

BENZIMIDAZOLE-IMIDAZOLE DERIVATIVES

This application is a divisional of U.S. application Ser. No. 13/508,186 filed Nov. 3, 2010, which is a national stage application of PCT/EP2010/066668, filed Nov. 3, 2010, which claims priority benefit of Application No. EP 10154583.8 filed Feb. 24, 2010, which claims priority benefit of Application No. EP 09175015.8 filed Nov. 4, 2009. The complete disclosures of the aforementioned related patent applications are hereby incorporated herein by reference for all purposes.

TECHNICAL FIELD

This invention relates to benzimidazole-imidazole derivatives, which are inhibitors of the hepatitis C virus (HCV), their synthesis and their use in the treatment or prophylaxis of HCV.

BACKGROUND ART

HCV is a single stranded, positive-sense RNA virus belonging to the Flaviviridae family of viruses in the hepacivirus genus. The viral genome translates into a single open reading frame that encodes for multiple structural and non structural proteins.

The NS5A protein of HCV is located downstream of the NS4B protein and upstream of the NS5B protein. Upon posttranslational cleavage by the viral serine protease NS3/4A, the NS5A matures into a zinc containing, three-domain phosphoprotein that either exists as a hypophosphorylated (56-kDa, p56) or hyperphosphorylated species (58-kDa, p58). NS5A of HCV is implicated in multiple aspects of the viral lifecycle including viral replication and infectious particle assembly as well as modulation of the environment of its host cell. Although no enzymatic function has been ascribed to the protein it is reported to interact with numerous viral and cellular factors.

A number of patents and patent applications disclose compounds with HCV inhibitory activity, in particular targeting NS5A. WO2006/133326 discloses stilbene derivatives while WO 2008/021927, WO 2008/021928, WO2009102325 and WO2009/102318 disclose biphenyl derivatives having NS5A HCV inhibitory activity. US2009/0202483 discloses bridged biphenyl derivatives. WO 2008/048589 discloses 4-(phenylethynyl)-1H-pyrazole derivatives and their antiviral use. WO 2008/070447 discloses a broad range of HCV inhibiting compounds including a benzimidazole moiety. WO2010/099527. WO2010/065668, WO2010/065674 and WO2010/065681 disclose benzimidazole-imidazole derivatives as HCV NS5A inhibitors. For instance, compounds having the following structure and Chemical Abstracts Number are disclosed in Table 1 of WO2010/065674:

TABLE A

| Structure of WO2010/065674 | Chemical Abstracts Number (CAS), CAS name and compound reference number in WO 2010/065674 |
|---|---|
| 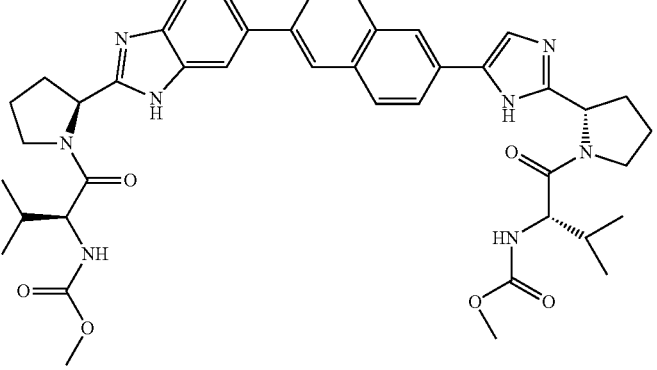 | CAS 1242087-93-9 - Compound 174 N-[(1S)-1-[[(2S)-2-[5-[6-[2-[(2S)-1-[(2S)-2-[(methoxycarbonyl)amino]-3-methyl-1-oxobutyl]-2-pyrrolidinyl]-1H-benzimidazol-6-yl]-2-naphthalenyl]-1H-imidazol-2-yl]-1-pyrrolidinyl]carbonyl]-2-methylpropyl]-carbamic acid, methyl ester |
| 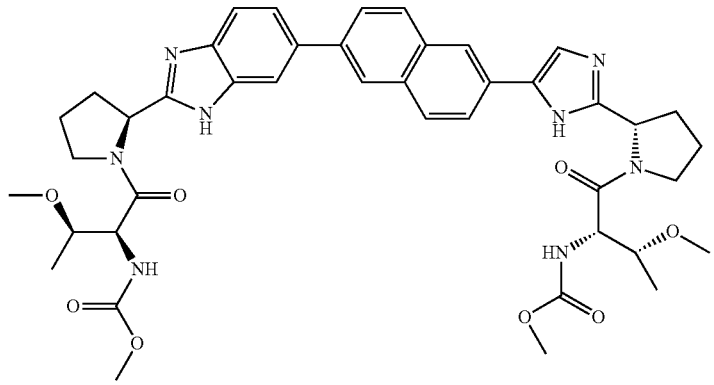 | CAS 1242087-95-1 - compound 176 N-[(1S,2R)-2-methoxy-1-[[(2S)-2-[5-[6-[2-[(2S)-1-[(2S,3R)-3-methoxy-2-[(methoxycarbonyl)amino]-1-oxobutyl]-2-pyrrolidinyl]-1H-benzimidazol-6-yl]-2-naphthalenyl]-1H-imidazol-2-yl]-1-pyrrolidinyl]carbonyl]propyl]-carbamic acid, methyl ester |

TABLE A-continued

| Structure of WO2010/065674 | Chemical Abstracts Number (CAS), CAS name and compound reference number in WO 2010/065674 |
|---|---|
| 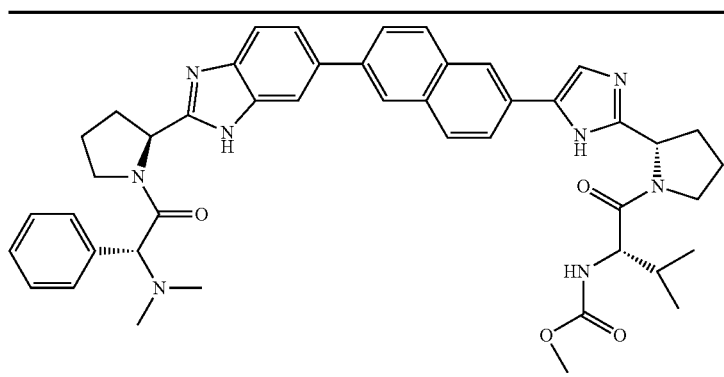 | CAS 1228552-40-6 - compound 177<br>N-[(1S)-1-[[(2S)-2-[5-[6-[2-[(2S)-1-[(2R)-2-(dimethylamino)-2-phenylacetyl]-2-pyrrolidinyl]-1H-benzimidazol-6-yl]-2-naphthalenyl]-1H-imidazol-2-yl]-1-pyrrolidinyl]carbonyl]-2-methylpropyl]-carbamic acid, methyl ester |
| 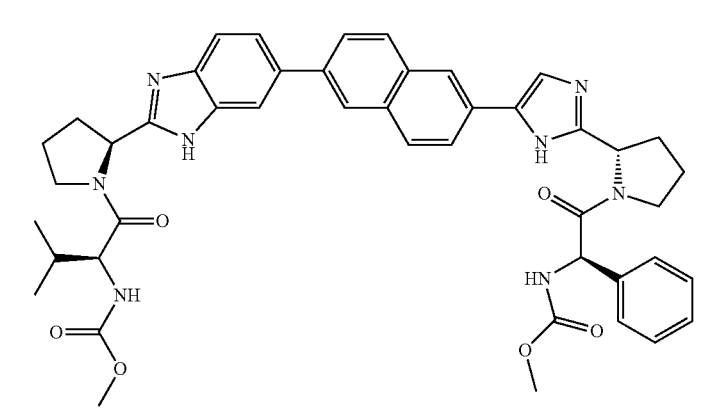 [SMILES: COC(=O)N[C@H](C(=O)N1CCC[C@H]1c1nc2ccc(-c3ccc4cc(-c5cnc([C@@H]6CCCN6C(=O)[C@H](NC(=O)OC)c6ccccc6)[nH]5)ccc4c3)cc2[nH]1)C(C)C] | Compound 179 |
| 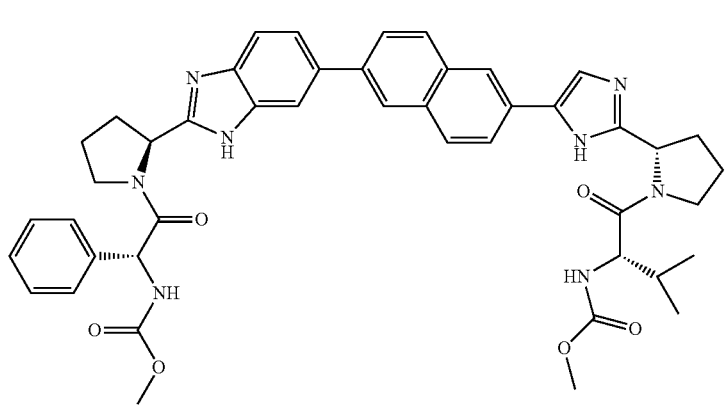 [SMILES: COC(=O)N[C@H](C(=O)N1CCC[C@H]1c1ncc(-c2ccc3cc(-c4ccc5nc([C@@H]6CCCN6C(=O)[C@H](NC(=O)OC)c6ccccc6)[nH]c5c4)ccc3c2)[nH]1)C(C)C] | Compound 181 |
| 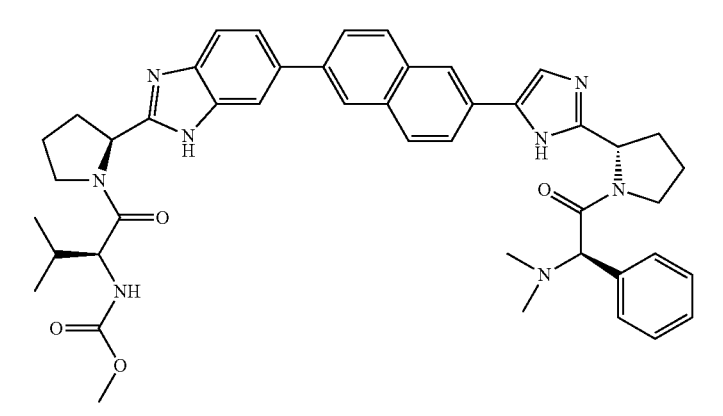 [SMILES: COC(=O)N[C@H](C(=O)N1CCC[C@H]1c1nc2ccc(-c3ccc4cc(-c5cnc([C@@H]6CCCN6C(=O)[C@@H](c6ccccc6)N(C)C)[nH]5)ccc4c3)cc2[nH]1)C(C)C] | CAS 1228552-49-5 - compound 182<br>N-[(1S)-1-[[(2S)-2-[6-[6-[2-[(2S)-1-[(2R)-2-(dimethylamino)-2-phenylacetyl]-2-pyrrolidinyl]-1H-imidazol-5-yl]-2-naphthalenyl]-1H-benzimidazol-2-yl]-1-pyrrolidinyl]carbonyl]-2-methylpropyl]-carbamic acid, methyl ester |

Following the initial acute infection, a majority of infected individuals develop chronic hepatitis because HCV replicates preferentially in hepatocytes but is not directly cytopathic. In particular, the lack of a vigorous T-lymphocyte response and the high propensity of the virus to mutate appear to promote a high rate of chronic infection. Chronic hepatitis can progress to liver fibrosis, leading to cirrhosis, end-stage liver disease, and HCC (hepatocellular carcinoma), making it the leading cause of liver transplantations.

There are six major HCV genotypes and more than 50 subtypes, which are differently distributed geographically. HCV genotype 1 is the predominant genotype in Europe and in the US. The extensive genetic heterogeneity of HCV has important diagnostic and clinical implications, perhaps explaining difficulties in vaccine development and the lack of response to current therapy.

Transmission of HCV can occur through contact with contaminated blood or blood products, for example following blood transfusion or intravenous drug use. The introduction of diagnostic tests used in blood screening has led to a downward trend in post-transfusion HCV incidence. However, given the slow progression to the end-stage liver disease, the existing infections will continue to present a serious medical and economic burden for decades.

Current HCV therapies are based on (pegylated) interferon-alpha (IFN-α) in combination with ribavirin. This combination therapy yields a sustained virologic response in 40% of patients infected by genotype 1 HCV and about 80% of those infected by genotypes 2 and 3. Beside the limited efficacy on HCV genotype 1, this combination therapy has significant side effects including influenza-like symptoms, hematologic abnormalities, and neuropsychiatric symptoms. Hence, in order to overcome the disadvantages of current HCV therapy such as side effects, limited efficacy, the emerging of resistance, and compliance failures, as well as to improve the sustained viral load response, there is a need for more effective, convenient and better-tolerated treatments.

The present invention concerns a group of benzimidazole-imidazole derivatives capable of inhibiting the HCV replication cycle.

Compounds of the present invention are also attractive due to the fact that they show a greater selectivity to inhibit the HCV replication cycle when compared to their capacity to inhibit the HIV replication. HIV infected patients often suffer from co-infections such as HCV. Treatment of such patients with an HCV inhibitor that also inhibits HIV may lead to the undesired emergence of resistant HIV strains.

DESCRIPTION OF THE INVENTION

In one aspect, the present invention provides compounds, which can be represented by the formula I:

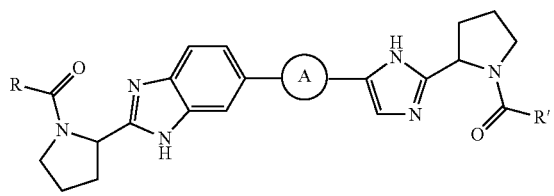

(I)

or stereoisomeric forms thereof, wherein:
A is phenylene or naphthylene, each of which may be optionally substituted with 1, 2 or 3 substituents selected from halo or $C_{1-3}$alkyl;
R and R' are, each independently, —$CR_1R_2R_3$, aryl, heteroaryl or hetero$C_{4-6}$cycloalkyl, whereby aryl and heteroaryl may optionally be substituted with 1 or 2 substituents selected from halo and methyl; and wherein
$R_1$ is hydrogen;
  $C_{1-4}$alkyl optionally substituted with methoxy, hydroxy or dimethylamino;
  phenyl optionally substituted with 1, 2 or 3 substituents independently selected from halo, $C_{1-4}$alkoxy and trifluoromethoxy;
  1,3-benzodioxolanyl;
  benzyl optionally substituted with 1, 2 or 3 substituents independently selected from halo or methoxy;
  $C_{3-6}$cycloalkyl;
  heteroaryl;
  hetero$C_{4-6}$cycloalkyl; or
  heteroarylmethyl;
$R_2$ is hydrogen, hydroxyl, amino, mono- or di-$C_{1-4}$alkylamino, $C_{1-4}$alkylcarbonylamino, $C_{1-4}$alkyloxycarbonylamino, $C_{1-4}$alkylaminocarbonylamino, piperidin-1-yl or imidazol-1-yl;
$R_3$ is hydrogen,
or $R_1$ and $R_3$ together form an oxo or a cyclopropyl group;
or pharmaceutically acceptable salts and/or solvates thereof.

In another aspect, the present invention provides compounds which can be represented by the following compounds of formula (I-PR):

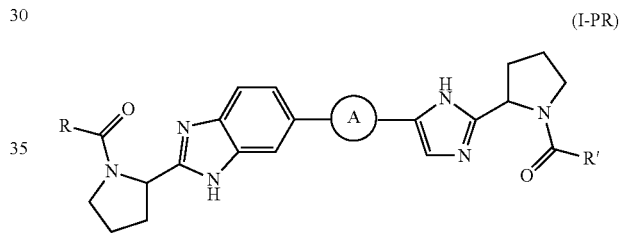

(I-PR)

or stereoisomeric forms thereof, wherein:
A is phenylene or naphthylene, each of which may be optionally substituted with 1, 2 or 3 substituents selected from halo or $C_{1-3}$alkyl;
R and R' are, each independently, —$CR_1R_2R_3$, aryl, heteroaryl or hetero$C_{4-6}$cycloalkyl, whereby aryl and heteroaryl may optionally be substituted with 1 or 2 substituents selected from halo and methyl; and wherein
$R_1$ is hydrogen;
  $C_{1-4}$alkyl optionally substituted with methoxy or dimethylamino;
  phenyl optionally substituted with 1, 2 or 3 substituents independently selected from halo, $C_{1-4}$alkoxy and trifluoromethoxy;
  1,3-benzodioxolanyl;
  benzyl optionally substituted with 1, 2 or 3 substituents independently selected from halo or methoxy;
  $C_{3-6}$cycloalkyl;
  heteroaryl;
  hetero$C_{4-6}$cycloalkyl; or
  heteroarylmethyl;
$R_2$ is hydrogen, hydroxyl, amino, mono- or di-$C_{1-4}$alkylamino, $C_{1-4}$alkylcarbonylamino, $C_{1-4}$alkyloxycarbonylamino, $C_{1-4}$alkylaminocarbonylamino, piperidin-1-yl or imidazol-1-yl;
$R_3$ is hydrogen,
or $R_1$ and $R_3$ together form an oxo or a cyclopropyl group;
or pharmaceutically acceptable salts and/or solvates thereof.

In another aspect, the present invention provides compounds, which can be represented by the formula (I-COR):

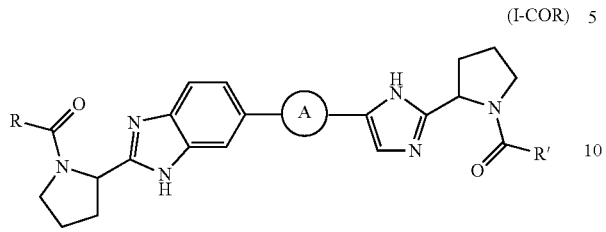

(I-COR)

and the stereoisomeric forms thereof, wherein:
A is phenylene or naphthylene, each of which may be optionally substituted with 1, 2 or 3 substituents selected from halo or $C_{1-3}$alkyl;
R and R' are, each independently, —$CR_1R_2R_3$, aryl, heteroaryl or hetero$C_{4-6}$cycloalkyl, whereby aryl and heteroaryl may optionally be substituted with 1 or 2 substituents selected from halo and methyl; and wherein
  $R_1$ is hydrogen;
    $C_{1-4}$alkyl optionally substituted with methoxy, hydroxy or dimethylamino;
    phenyl optionally substituted with 1, 2 or 3 substituents independently selected from halo, $C_{1-4}$alkoxy and trifluoromethoxy;
    1,3-benzodioxolanyl;
    benzyl optionally substituted with 1, 2 or 3 substituents independently selected from halo or methoxy;
    $C_{3-6}$cycloalkyl;
    heteroaryl;
    hetero$C_{1-4}$cycloalkyl; or
    heteroarylmethyl;
  $R_2$ is hydrogen, hydroxyl, amino, mono- or di-$C_{1-4}$alkylamino, $C_{1-4}$alkylcarbonylamino, $C_{1-4}$alkyloxycarbonylamino, $C_{1-4}$alkylaminocarbonylamino, piperidin-1-yl or imidazol-1-yl;
  $R_3$ is hydrogen,
  or $R_1$ and $R_3$ together form a cyclopropyl group;
  or $R_2$ and $R_3$ form oxo;
  and the pharmaceutically acceptable salts and the solvates thereof.

In another aspect, the present invention provides compounds, which can be represented by the formula (I-PR-COR):

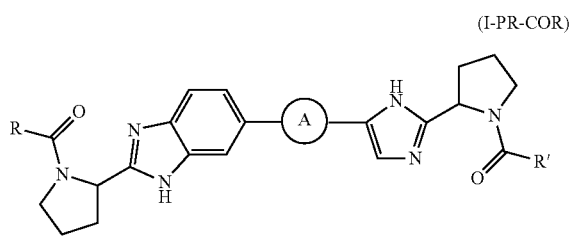

(I-PR-COR)

or stereoisomeric forms thereof, wherein:
A is phenylene or naphthylene, each of which may be optionally substituted with 1, 2 or 3 substituents selected from halo or $C_{1-3}$alkyl;
R and R' are, each independently, —$CR_1R_2R_3$, aryl, heteroaryl or hetero$C_{4-6}$cycloalkyl, whereby aryl and heteroaryl may optionally be substituted with 1 or 2 substituents selected from halo and methyl; and wherein
  $R_1$ is hydrogen;
    $C_{1-4}$alkyl optionally substituted with methoxy or dimethylamino;
    phenyl optionally substituted with 1, 2 or 3 substituents independently selected from halo, $C_{1-4}$alkoxy and trifluoromethoxy;
    1,3-benzodioxolanyl;
    benzyl optionally substituted with 1, 2 or 3 substituents independently selected from halo or methoxy;
    $C_{3-6}$cycloalkyl;
    heteroaryl;
    hetero$C_{4-6}$cycloalkyl; or
    heteroarylmethyl;
  $R_2$ is hydrogen, hydroxyl, amino, mono- or di-$C_{1-4}$alkylamino, $C_{1-4}$alkylcarbonylamino, $C_{1-4}$alkyloxycarbonylamino, $C_{1-4}$alkylaminocarbonylamino, piperidin-1-yl or imidazol-1-yl;
  $R_3$ is hydrogen,
  or $R_1$ and $R_3$ together form a cyclopropyl group;
  or $R_2$ and $R_3$ form oxo;
  and the pharmaceutically acceptable salts and the solvates thereof.

In another aspect, the present invention provides compounds which can be represented by the following compounds of formula (I-PR):

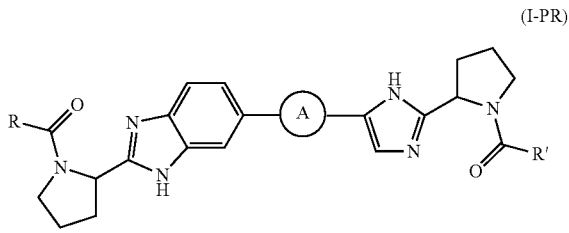

(I-PR)

or stereoisomeric forms thereof, wherein:
A is phenylene or naphthylene, each of which may be optionally substituted with 1, 2 or 3 substituents selected from halo or $C_{1-3}$alkyl;
R and R' are, each independently, —$CR_1R_2R_3$, aryl, heteroaryl or hetero$C_{4-6}$cycloalkyl, whereby aryl and heteroaryl may optionally be substituted with 1 or 2 substituents selected from halo and methyl; and wherein
  $R_1$ is hydrogen;
    $C_{1-4}$alkyl optionally substituted with methoxy or dimethylamino;
    phenyl optionally substituted with 1, 2 or 3 substituents independently selected from halo, $C_{1-4}$alkoxy and trifluoromethoxy;
    1,3-benzodioxolanyl;
    benzyl optionally substituted with 1, 2 or 3 substituents independently selected from halo or methoxy;
    $C_{3-6}$cycloalkyl;
    heteroaryl;
    hetero $C_{4-6}$cycloalkyl; or
    heteroarylmethyl;
  $R_2$ is hydrogen, hydroxyl, amino, mono- or di-$C_{1-4}$alkylamino, $C_{1-4}$alkylcarbonylamino, $C_{1-4}$alkyloxycarbonylamino, $C_{1-4}$alkylaminocarbonylamino, piperidin-1-yl or imidazol-1-yl;

$R_3$ is hydrogen, or $R_1$ and $R_3$ together form an oxo or a cyclopropyl group;

or pharmaceutically acceptable salts and/or solvates thereof;

provided the compound is other than any one of the 6 compounds listed in Table A.

Whenever used herein, the term "compounds of formula I", "the present compounds", "compounds of the present invention" or subgroups of the compounds of formula (I) such as those defined herein by the different embodiments as well as "the compounds of formula (I-PR)", "the compounds of formula (I-COR)", "the compounds of formula (I PR-COR)" or similar terms, it is meant to include the compounds of formula I, or such subgroup thereof, including the possible stereoisomeric forms, and the pharmaceutically acceptable salts and solvates thereof, unless specified differently.

In a further aspect, the invention concerns the use of compounds of formula I, or subgroups thereof, as specified herein, for inhibiting the replication cycle of HCV. Alternatively, there is provided the use of said compounds for the manufacture of a medicament for inhibiting the replication cycle of HCV.

Embodiments of the present invention concern compounds of formula (I), or any subgroup thereof as defined herein by the different embodiments, wherein one or more of the definitions for A, R, R', $R_1$, $R_2$ and $R_3$ as specified herein, apply.

An embodiment of the present invention concerns those compounds of formula I, or any subgroup thereof, wherein R and R' are independently —$CR_1R_2R_3$ or an optionally substituted 5-membered heteroaryl; in particular, wherein R and R' are independently —$CR_1R_2R_3$; more in particular, wherein R and R' are —$CR_1R_2R_3$ and are the same; alternatively, R and R' are —$CR_1R_2R_3$ and are different.

Another embodiment of the present invention concerns those compounds of formula I, or any subgroup thereof, wherein $R_2$ is hydroxyl, amino, mono- or di-$C_{1-4}$alkylamino, $C_{1-4}$alkylcarbonylamino or $C_{1-4}$alkyloxycarbonylamino; in particular, $R_2$ is $C_{1-4}$ alkyl-carbonylamino or $C_{1-4}$alkyloxycarbonylamino; or, $R_2$ is $C_{1-4}$ alkyloxycarbonylamino. More in particular, $R_2$ is methoxycarbonylamino.

Another embodiment of the present invention concerns those compounds of formula I, or any subgroup thereof, wherein $R_1$ is selected from $C_{1-4}$alkyl; phenyl optionally substituted with 1 or 2 substituents independently selected from halo, methyl, methoxy; 1,3-benzodioxolanyl; and heteroaryl. In particular, $R_1$ is selected from branched $C_{3-4}$alkyl; phenyl optionally substituted with halo or methyl; and heteroaryl. More in particular, $R_1$ is selected from branched $C_{3-4}$alkyl; phenyl optionally substituted with halo. Or, $R_1$ is branched $C_{3-4}$alkyl. Alternatively, in another particular embodiment, $R_1$ is selected from $C_{1-4}$alkyl optionally substituted with methoxy.

Another embodiment of the present invention concerns those compounds of formula I, or any subgroup thereof, wherein $R_1$ is selected from $C_{1-4}$alkyl; phenyl optionally substituted with 1 or 2 substituents independently selected from halo, methoxy; 1,3-benzodioxolanyl; and heteroaryl. In particular, $R_1$ is selected from branched $C_{3-4}$alkyl; phenyl optionally substituted with halo; and heteroaryl.

Another embodiment of the present invention concerns those compounds of formula I, or any subgroup thereof, wherein R=(C=O)— and R'—C(=O)— are independently —(C=O)—$CR_1R_2R_3$ selected from

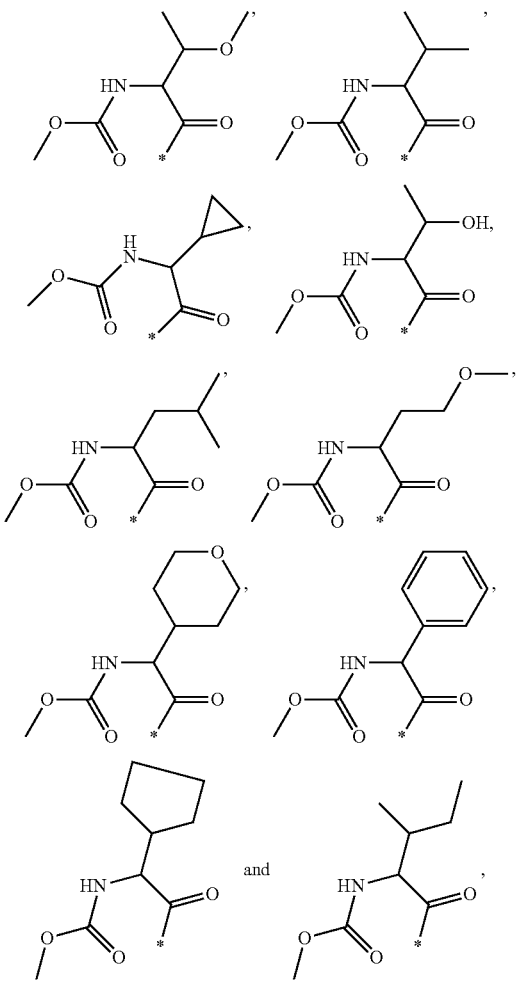

wherein * denotes point of attachment to the pyrrolidine nitrogen. In particular, R—(C=O)— and R'—C(=O)— are independently —(C=O)—$CR_1R_2R_3$ selected from

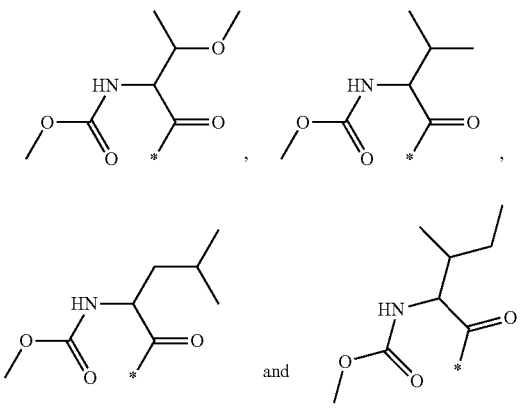

Another embodiment of the present invention concerns those compounds of formula I, or any subgroup thereof, wherein A is phenylene, in particular wherein A is 1,4-phenylene of structure wherein the dashed lines indicate the points of attachment to the remainder of the molecule.

Another embodiment of the present invention concerns those compounds of formula I, or any subgroup thereof, wherein A is naphthylene, in particular wherein A is 2,6-naphthylene of structure wherein the dashed lines indicate the points of attachment to the remainder of the molecule.

Another embodiment of the present invention concerns those compounds of formula (I), or any subgroup thereof, wherein A is naphthylene which may be optionally substituted with 1, 2 or 3 substituents selected from halo or $C_{1-3}$alkyl; $R^1$ is as defined in the compounds of formula (I) but different from unsubstituted 2-propyl, and when $R^1$ in R is 1-methoxy-ethyl, then $R^1$ in R' is different from 1-methoxyethyl. In particular, the present invention concerns those compounds of formula (I-PR) wherein A is naphthylene which may be optionally substituted with 1, 2 or 3 substituents selected from halo or $C_{1-3}$alkyl, more in particular A is naphthylene, even more in particular A is 2,6-naphthylene;

R and R' are, each independently, —$CR_1R_2R_3$, aryl, heteroaryl or hetero$C_{4-6}$cycloalkyl, whereby aryl and heteroaryl may optionally be substituted with 1 or 2 substituents selected from halo and methyl; and wherein $R_1$ is hydrogen;
$C_{1-4}$alkyl optionally substituted with methoxy or dimethylamino, but different from unsubstituted 2-propyl;
phenyl optionally substituted with 1, 2 or 3 substituents independently selected from halo, $C_{1-4}$alkoxy and trifluoromethoxy;
1,3-benzodioxolanyl;
benzyl optionally substituted with 1, 2 or 3 substituents independently selected from halo or methoxy;
$C_{3-6}$cycloalkyl;
heteroaryl;
hetero$C_{4-6}$cycloalkyl; or
heteroarylmethyl;
$R_2$ is hydrogen, hydroxyl, amino, mono- or di-$C_{1-4}$alkylamino, $C_{1-4}$alkylcarbonylamino, $C_{1-4}$alkyloxycarbonylamino, $C_{1-4}$alkylaminocarbonylamino, piperidin-1-yl or imidazol-1-yl;
$R_3$ is hydrogen,
or $R_1$ and $R_3$ together form an oxo or a cyclopropyl group;
or pharmaceutically acceptable salts and/or solvates thereof; provided
when $R^1$ in R is 1-methoxyethyl, then $R^1$ in R' is different from 1-methoxyethyl.

Another embodiment concerns compounds of formula (I), or any subgroup thereof, wherein
A is naphthylene;
R and R' are, each independently, —$CR_1R_2R_3$ wherein each $R_1$ independently is $C_{1-4}$alkyl optionally substituted with methoxy or hydroxy; cyclopentyl; or phenyl;

each $R_2$ independently is amino, mono- or di-$C_{1-4}$alkylamino, $C_{1-4}$alkylcarbonylamino, $C_{1-4}$alkyloxycarbonylamino, or $C_{1-4}$alkylaminocarbonylamino; and
each $R_3$ is hydrogen,
provided that:
$R_1$ is other than 2 propyl when $R_2$ is methoxycarbonylamino; and
$R_1$ in R' is other than 1-methoxyethyl when $R_2$ in R' is methoxycarbonylamino;
and the pharmaceutically acceptable salts and the solvates thereof.

Another embodiment concerns compounds of Formula (I) or any subgroup thereof such as compounds of formula (I-PR), wherein A is 2,6-naphthylene of structure and wherein the compounds in this embodiment are different from any one of the 6 compounds listed in Table A.

Another embodiment concerns compounds of formula (I) or any subgroup thereof wherein R and R' are different from one another.

Another embodiment concerns compounds of Formula (I) wherein each $R_2$ independently is $C_{1-4}$alkylcarbonylamino or $C_{1-4}$alkyloxycarbonylamino.

Another embodiment concerns compounds of formula (I) or any subgroup thereof wherein each $R_2$ independently is methoxycarbonylamino.

Another embodiment concerns compounds of formula (I) or any subgroup thereof wherein each $R_1$ independently is selected from branched $C_{3-4}$alkyl, methoxy$C_{2-3}$alkyl, cyclopentyl or phenyl.

Another embodiment concerns compounds of formula (I) or any subgroup thereof wherein $R_1$ in R is 1-methylpropyl, 2-methylpropyl, 2-methoxyethyl, cyclopentyl or phenyl; $R_1$ in R' is 1-methylethyl, 1-methylpropyl, 2-methylpropyl, 1-methoxyethyl, cyclopentyl or phenyl.

Another embodiment concerns compounds of formula (I) or any subgroup thereof wherein R and R' independently are —$CR_1R_2R_3$ both the carbon atoms bearing the $R_1$, $R_2$ and $R_3$ substituent have the S-configuration.

Another embodiment concerns compounds of formula (I), or any subgroup thereof such as the compounds of formula (I-PR), wherein the compound is of formula Ia Ia Another embodiment concerns compounds of formula (I) or any subgroup thereof wherein the compound is one of the following compounds of Table 1a: compound 9, compound 11, compound 13, compound 14, compound 16, compound 17 or compound 18, or a pharmaceutically acceptable salt thereof.

In a further aspect, the present invention provides compounds of formula I, and their pharmaceutically acceptable salts and solvates thereof, for use in the treatment or prophylaxis (or the manufacture of a medicament for the treatment or prophylaxis) of HCV infection. Representative HCV genotypes in the context of treatment or prophylaxis in accordance with the present invention include genotype 1b (prevalent in Europe) or 1a (prevalent in North America). The present invention also provides a method for the treatment or prophylaxis of HCV infection, in particular infection with HCV of the genotype 1a or 1b.

Pure stereoisomeric forms of the compounds and intermediates as mentioned herein are defined as isomers substantially free of other enantiomeric or diastereomeric forms of the same basic molecular structure of said compounds or intermediates. In particular, the term "stereoisomerically pure" concerns compounds or intermediates having a stereoisomeric excess of at least 80% (i.e. minimum 90% of one isomer and maximum 10% of the other possible isomers) up to a stereoisomeric excess of 100% (i.e. 100% of one isomer and none of the other), more in particular, compounds or intermediates having a stereoisomeric excess of 90% up to 100%, even more in particular having a stereoisomeric excess of 94% up to 100% and most in particular having a stereoisomeric excess of 97% up to 100%. The terms "enantiomerically pure" and "diastereomerically pure" should be understood in a similar way, but then having regard to the enantiomeric excess, and the diastereomeric excess, respectively, of the mixture in question.

Pure stereoisomeric forms or stereoisomers of the compounds and intermediates of this invention may be obtained by the application of art-known procedures. For instance, enantiomers may be separated from each other by the selective crystallization of their diastereomeric salts with optically active acids or bases. Examples thereof are tartaric acid, dibenzoyltartaric acid, ditoluoyltartaric acid and camphorsulfonic acid.

Alternatively, enantiomers may be separated by chromatographic techniques using chiral stationary phases. Said pure stereochemically isomeric forms may also be derived from the corresponding pure stereoisomeric forms of the appropriate starting materials, provided that the reaction occurs stereospecifically. Preferably, if a specific stereoisomer is desired, said compound is synthesized by stereospecific methods of preparation. These methods will advantageously employ enantiomerically pure starting materials.

The diastereomeric racemates of the compounds of formula I can be obtained separately by conventional methods. Appropriate physical separation methods that may advantageously be employed are, for example, selective crystallization and chromatography, e.g. column chromatography or supercritical fluid chromatography.

The compounds of formula I have several centers of chirality. Of interest are the stereogenic centers of the pyrrolidine ring at the 2-carbon atom. The configuration at this position may be that corresponding to L-proline, i.e.

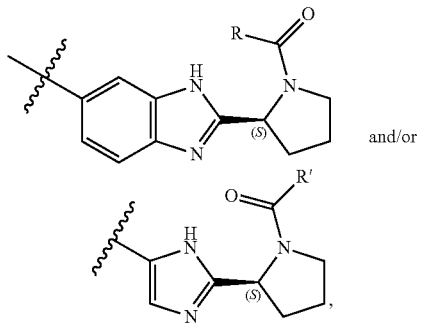

and/or or that corresponding to D-proline, i.e.

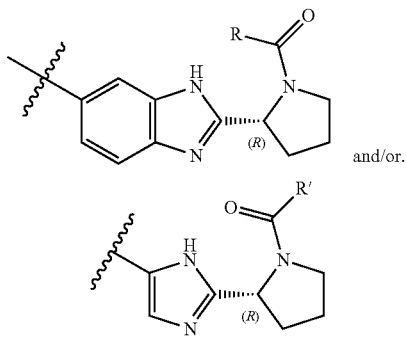

and/or.

Also of interest are stereogenic centers occurring in —$CR_1R_2R_3$ moieties of compounds of formula I. Embodiments of the present invention therefore concerns those compounds of formula I, or any subgroup thereof, wherein the carbon atom C in —$CR_1R_2R_3$ appears in its S-configuration, in particular when $R_1$ is $C_{1-4}$alkyl optionally substituted with methoxy, hydroxy or dimethylamino; benzyl optionally substituted with 1, 2 or 3 substituents independently selected from halo or methoxy; $C_{3-6}$cycloalkyl; heteroC$_{4-6}$cycloalkyl; or heteroarylmethyl. Particular examples of —(C=O)—$CR_1R_2R_3$ moieties of compounds of formula I with specified stereochemistry are

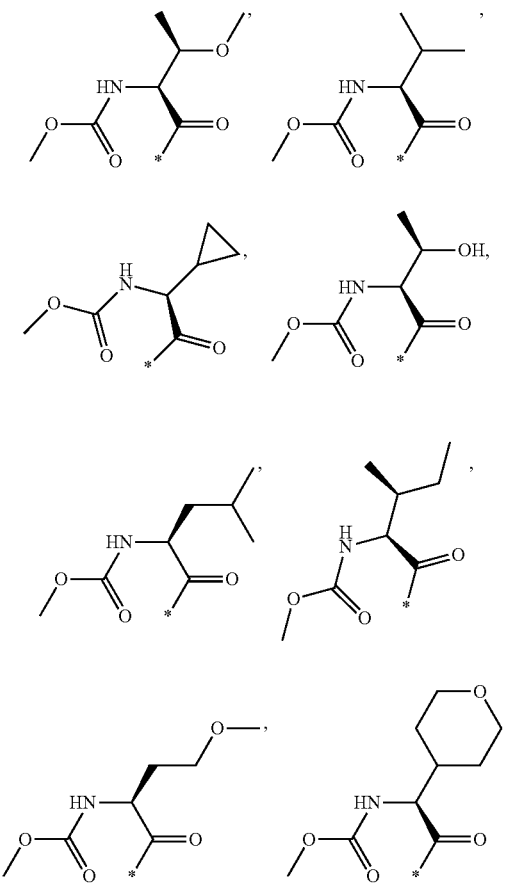

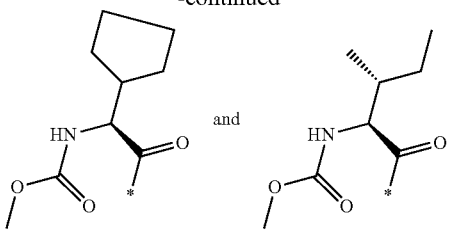

and wherein * denotes point of attachement to the remainder of the molecule.

The pharmaceutically acceptable addition salts comprise the therapeutically active non-toxic acid and base addition salt forms of the compounds of formula (I) or any subgroup thereof. Of interest are the free, i.e. non-salt forms of the compounds of formula I, or of any subgroup thereof.

The pharmaceutically acceptable acid addition salts can conveniently be obtained by treating the base form with such appropriate acid. Appropriate acids comprise, for example, inorganic acids such as hydrohalic acids, e.g. hydrochloric or hydrobromic acid, sulfuric, nitric, phosphoric and the like acids; or organic acids such as, for example, acetic, propionic, hydroxyacetic, lactic, pyruvic, oxalic (i.e. ethanedioic), malonic, succinic (i.e. butanedioic acid), maleic, fumaric, malic (i.e. hydroxyl-butanedioic acid), tartaric, citric, methanesulfonic, ethanesulfonic, benzenesulfonic, p-toluenesulfonic, cyclamic, salicylic, p-aminosalicylic, pamoic and the like acids. Conversely said salt forms can be converted by treatment with an appropriate base into the free base form.

The compounds of formula (I) containing an acidic proton may also be converted into their base addition salts, in particular metal or amine addition salt forms, by treatment with appropriate organic and inorganic bases. Appropriate base salt forms comprise, for example, the ammonium salts, the alkali and earth alkaline metal salts, e.g. the lithium, sodium, potassium, magnesium, calcium salts and the like, salts with organic bases, e.g. the benzathine, N-methyl-D-glucamine, hydrabamine salts, and salts with amino acids such as, for example, arginine, lysine and the like.

The term "solvates" covers any pharmaceutically acceptable solvate that the compounds of formula I as well as any pharmaceutically acceptable salt thereof, are able to form. Such solvates are for example hydrates, alcoholates, e.g. ethanolates, propanolates, and the like.

Some of the compounds of formula I may also exist in tautomeric forms. For example, tautomeric forms of amide (—C(=O)—NH—) groups are iminoalcohols (—C(OH) =N—). Tautomeric forms, although not explicitly indicated in the structural formulae represented herein, are intended to be included within the scope of the present invention.

As used herein, "$C_{1-4}$alkyl" as a group or part of a group defines saturated straight or branched chain hydrocarbon groups having from 1 to 4 carbon atoms such as for example methyl, ethyl, 1-propyl, 2-propyl, 1-butyl, 2-butyl, 2-methyl-1-propyl, 2-methyl-2-propyl. For the purpose of the present invention, of interest amongst $C_{1-4}$alkyl is $C_{3-4}$alkyl, i.e. straight or branched chain hydrocarbon groups having 3 or 4 carbon atoms such as 1-propyl, 2-propyl, 1-butyl, 2-butyl, 2-methyl-1-propyl, 2-methyl-2-propyl. Of particular interest may be branched $C_{3-4}$alkyl such as 2-propyl, 2-butyl, 2-methyl-1-propyl, 2-methyl-2-propyl.

The term "$C_{3-6}$cycloalkyl" is generic to cyclopropyl, cyclobutyl, cyclopentyl and cyclohexyl. Similarly, "$C_{4-6}$cycloalkyl" is generic to cyclobutyl, cyclopentyl and cyclohexyl "$C_1$-$C_4$alkoxy" as a group or part of a group means a group of formula —O—$C_{1-4}$alkyl wherein $C_{1-4}$alkyl is as defined above. Examples of $C_{1-4}$alkoxy are methoxy, ethoxy, n-propoxy, or isopropoxy.

The term "halo" is generic to fluoro, chloro, bromo and iodo.

As used herein, the term "(=O)" or "oxo" forms a carbonyl moiety when attached to a carbon atom. It should be noted that an atom can only be substituted with an oxo group when the valency of that atom so permits.

As used herein, "aryl" is generic to phenyl and naphthyl.

As used herein, the term "heteroaryl" means an aromatic carbohydrate ring structure having 5 to 10 ring atoms of which at least one ring atom is a heteroatom selected from N, O and S, in particular from N and O.

As used herein, the term "hetero$C_{4-6}$cycloalkyl" means saturated cyclic hydrocarbon group as defined for "$C_{4-6}$cycloalkyl" wherein at least one carbon atom is replaced by a heteroatom selected from N, O and S, in particular from N and O. Examples of hetero$C_{4-6}$cycloalkyl include tetrahydro-2H-pyranyl, piperidinyl, tetrahydrofuranyl and pyrrolidinyl.

Where the position of a group on a molecular moiety is not specified (for example a substituent on phenyl) or is represented by a floating bond, such group may be positioned on any atom of such a moiety, as long as the resulting structure is chemically stable. When any variable is present more than once in the molecule, each definition is independent.

The compounds of the present invention can be synthesized using the following synthesis procedures. The acronyms as used herein have the following meaning:

"CDI" is meant to be N,N'-carbonyl-diimidazole.

"dppf" is meant to be 1,1'-Bis(diphenylphosphino)ferrocene

"4-DMAP" is meant to be 4-Dimethylaminopyridine

"DMSO" is meant to be Dimethyl Sulfoxide

"HMPT" is meant to be Hexamethylphosphorous Triamide

"DIPEA" is meant to be N,N-diisopropyl ethylamine

"DMF" is meant to be dimethylformamide

"THF" is meant to be tetrahydrofuran

"TEMPO" is meant to be 2,2,6,6-tetramethyl-1-piperidinyloxy

DBU is meant to be 1,8-diazabicyclo[5.4.0]undec-7-ene

HATU is meant to be O-(7-azabenzotriazol-1-yl)-N,N,N',N'-tetramethyluronium hexafluorophosphate TBTU is meant to be 2-(1H-benzotriazol-1-yl)-N,N,N',N'-tetramethyluronium tetrafluoroborate Scheme 1

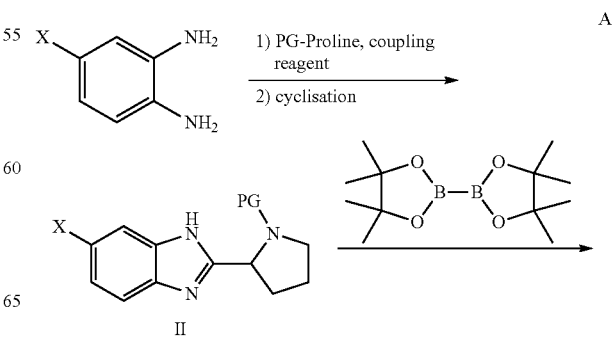

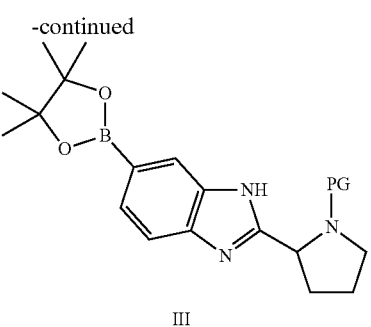

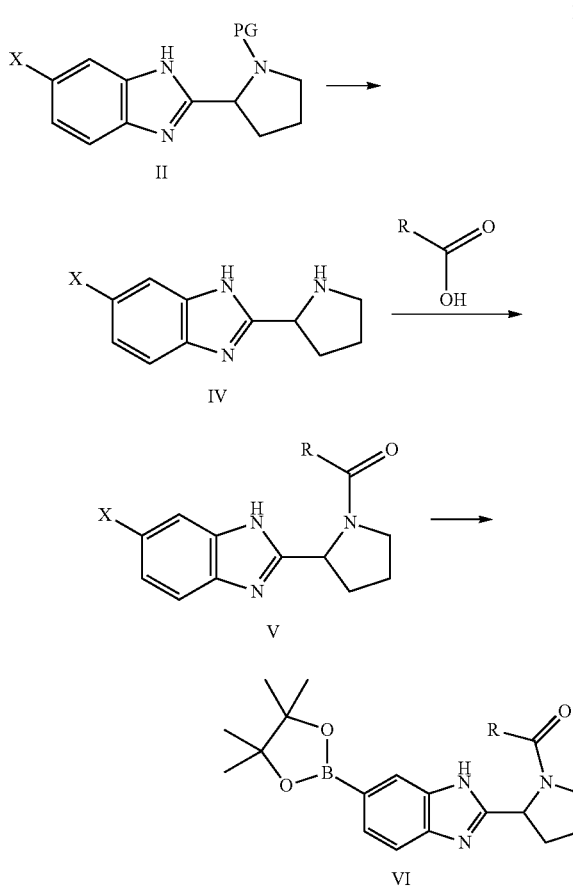

In scheme 1, the synthesis of compound II to VI, is described. In a first step, an amide bond is formed using PG-proline and a 4-halobenzene-1,2-diamine wherein X is Cl, Br or I, in the presence of a suitable coupling reagent for amino-group acylation, such as, for example, CDI. As used herein, PG is a protecting group on the pyrrolidine nitrogen, such as, for example, a carbamate protecting group like benzyloxycarbonyl, or tert-butoxycarbonyl, or, alternatively, PG may be R—C(=O)— wherein R has the meaning as defined for the compounds of formula I. The thus obtained intermediate is further cyclized, resulting in the benzimidazole derivative of formula II. Such cyclization can be carried out by treatment with an acid, such as, for example, acetic acid in a temperature range from 0 to 150° C., more specifically between 80° C. and 120° C. The intermediate of formula II can be converted to a boronic ester of formula III under Pd catalyzed conditions, for example in the presence of Pd(dppf)Cl$_2$, bis(pinacolato)diboron and a base, for example potassium acetate.

Compound IV (Scheme 1B) can be obtained after selective removal of the protecting group PG of the pyrrolidine nitrogen of intermediate II, under suitable conditions, such as, for example, using HCl in isopropanol when PG is tert-butoxycarbonyl. The resulting intermediate IV may then be converted to an intermediate of formula V by acylation with the appropriate acid of formula R—C(=O)—OH wherein R has the meaning as defined for the compounds of formula I.

Said acylation may be performed by reacting the starting materials in the presence of a coupling agent or by converting the carboxyl functionality into an active form such as an active ester, mixed anhydride or a carboxyl acid chloride or bromide. General descriptions of such coupling reactions and the reagents used therein can be found in general textbooks on peptide chemistry, for example, M. Bodanszky, "Peptide Chemistry", 2nd rev. ed., Springer-Verlag, Berlin, Germany, (1993).

Examples of coupling reactions for amino-group acylation or amide bond formation include the azide method, mixed carbonic-carboxylic acid anhydride (isobutyl chloroformate) method, the carbodiimide (dicyclohexylcarbodiimide, diisopropyl-carbodiimide, or water-soluble carbodiimide such as N-ethyl-N'-[3-(dimethylamino)-propyl] carbodiimide) method, the active ester method (e.g. p-nitrophenyl, p-chloro-phenyl, trichlorophenyl, pentachloro-phenyl, pentafluorophenyl, N-hydroxysuccinic imido and the like esters), the Woodward reagent K-method, the 1,1-carbonyl-diimidazole method, the phosphorus reagents or oxidation-reduction methods. Some of these methods can be enhanced by adding suitable catalysts, e.g. in the carbodiimide method by adding 1-hydroxybenzotriazole, or 4-DMAP. Further coupling agents are (benzotriazol-1-yloxy)-tris-(dimethylamino) phosphonium hexafluorophosphate, either by itself or in the presence of 1-hydroxybenzotriazole or 4-DMAP; or 2-(1H-benzotriazol-1-yl)-N,N,N',N'-tetramethyluronium tetrafluoroborate (TBTU), or O-(7-azabenzotriazol-1-yl)-N,N,N',N'-tetramethyluronium hexafluorophosphate (HATU). These coupling reactions can be performed in either solution (liquid phase) or solid phase. For the purpose of the present invention, a preferred method for acylation is performed employing HATU.

The coupling reactions preferably are conducted in an inert solvent, such as halogenated hydrocarbons, e.g. dichloromethane, chloroform, dipolar aprotic solvents such as acetonitrile, dimethylformamide, dimethylacetamide, DMSO, HMPT, ethers such as tetrahydrofuran (THF).

In many instances the coupling reactions are done in the presence of a suitable base such as a tertiary amine, e.g. triethylamine, diisopropylethylamine (DIPEA), N-methylmorpholine, N-methylpyrrolidine, 4-DMAP or 1,8-diazabicyclo[5.4.0]undec-7-ene (DBU). The reaction temperature may range between 0° C. and 50° C. and the reaction time may range between 15 min and 24 h. Intermediate V can then be converted to a boronic ester VI under Pd catalyzed conditions in the presence of bis(pinacolato)diboron like in the conversion from intermediate II to intermediate III.

Scheme 2

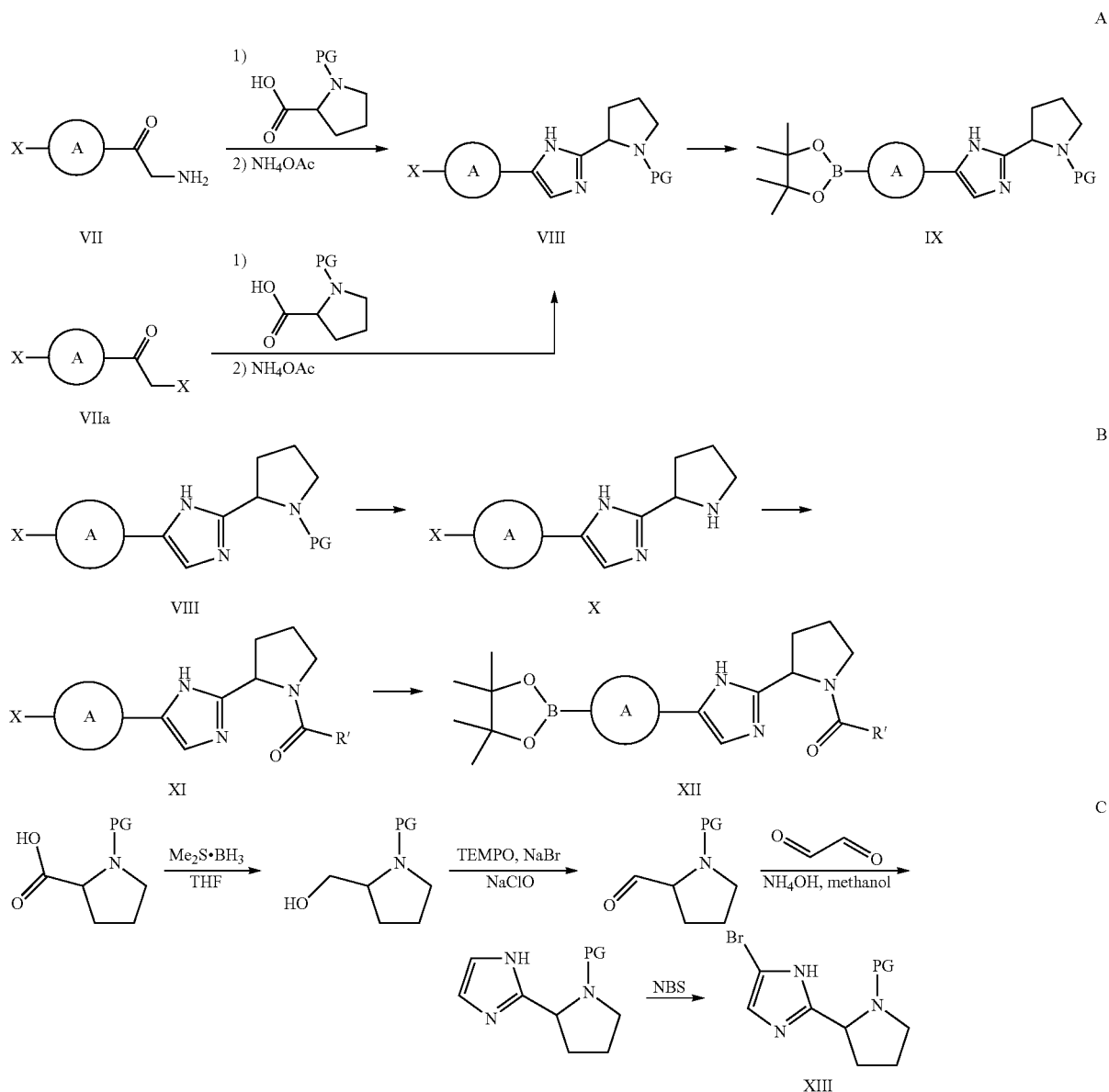

Further building blocks used in the synthesis of compounds of formula I are described in scheme 2. α-Amino ketone VII (Scheme 2A), wherein A has the same meaning as for compounds of formula I and X is a halogen, is coupled with a suitably protected proline whereby PG is a protection group on the pyrrolidine nitrogen, preferable tert-butoxycarbonyl or benzyloxycarbonyl, in the presence of coupling reagent for amino-group acylation as described above for the conversion of intermediate IV to intermediate V, preferable with HATU in the presence of DIPEA. The thus formed intermediate is cyclized to imidazole intermediates of general formula VIII by treatment with ammoniumacetate, preferable in a temperature range between 0° C. and 150° C., more specifically between 80° C. and 150° C. Alternatively, intermediate VIII can be obtained by coupling α-halo ketone VIIa whereby each X independently is a halo atom, with a suitably protected proline whereby PG is a protection group on the pyrrolidine nitrogen, preferable tert-butoxycarbonyl or benzyloxycarbonyl, in the presence of a suitable base, for example DIPEA, followed by cyclization to an imidazole intermediate VIII as described above, preferable in toluene or xylene. This compound can be further transformed to and intermediate of formula IX, in a similar way to the transformation of intermediate II to intermediate III. Alternatively intermediate VIII can be deprotected, for example by treatment with HCl in isopropanol in case PG equals tert-butoxycarbonyl, to intermediate X (scheme 2B) and further transformed to intermediate XI, using similar conditions as those used in the transformation of intermediate IV to intermediate V. Boronic ester XII results from intermediate XI by using similar conditions to those used in the conversion of intermediate II to intermediate III.

Imidazole XIII can be synthesized in 4 steps starting from PG-Proline (Scheme 2C) whereby PG is a protecting group on the pyrrolidine nitrogen, preferable tert-butoxycarbonyl, as described in scheme 2C. Imidazole XIII' can be synthesized using

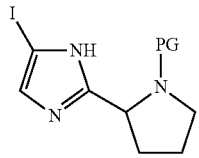

XIII' the same procedure except for the last steps wherein iodine instead of bromine is introduced on the imidazole, which can be achieved by diiodination with $I_2$/NaOH followed by removal of one iodide with $Na_2SO_3$.

Scheme 3

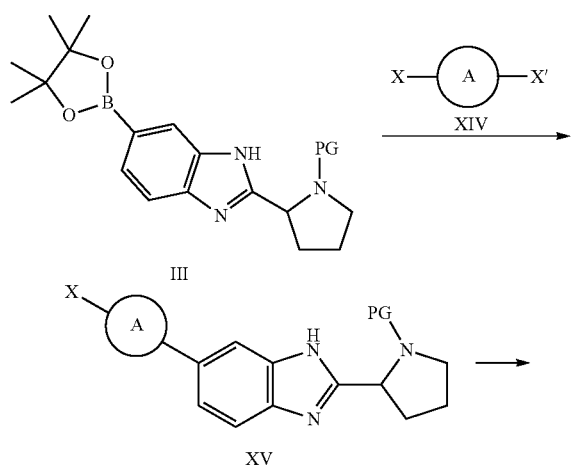

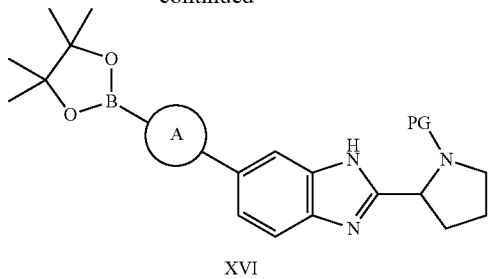

XVI

Other possible intermediates are described in scheme 3. Here a dihalogenide XIV of formula

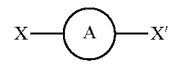

is used, wherein A has the meaning as defined for the compounds of formula I, and X and X' are halogens; independently selected from iodo, chloro and bromo. Alternatively, X and/or X' may be triflate used in combination with a halogen. Intermediate III is coupled with intermediate XIV, under Suzuki-Miyaura conditions, using one or more equivalents of intermediate XIV. The resulting intermediate XV is further transformed to XVI under conditions similar to those described to convert intermediate II to intermediate III. In case PG equals R—C(=O) wherein R has the meaning as defined for the compounds of formula I, intermediate III is the same as intermediate VI.

Scheme 4

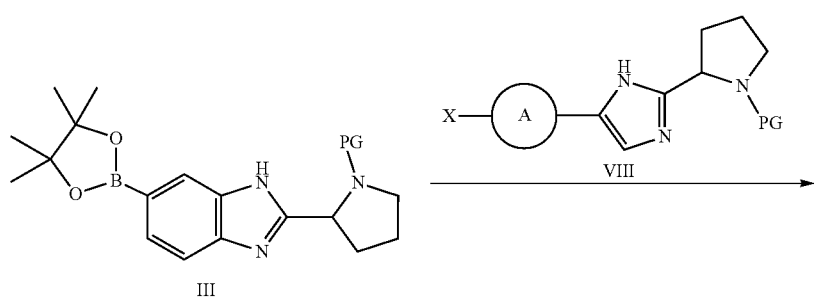

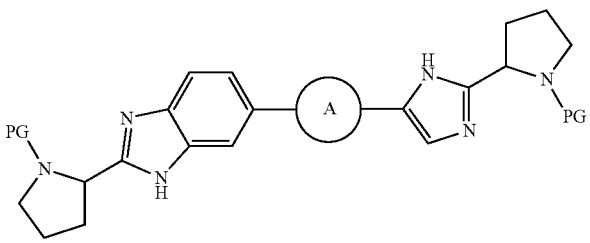

XVII

As illustrated in Scheme 4, the coupling of boronic ester III and halogenide or triflate VIII, wherein X is a halogen or a triflate, under Suzuki-Miyaura conditions results in the formation of intermediate XVII. Similar couplings of appropriate intermediates described in Scheme 1 to 3 using Suzuki-Miyaura conditions may also result in the formation of intermediates XVII. For example, bromide II and boronic ester IX can be coupled resulting in intermediate XVII, as described for intermediates III and VIII.

Alternatively, compounds of formula I may be obtained as illustrated in scheme 5. A boronic ester of formula XVI is coupled with bromide of formula XIII or Iodide of formula XIII', resulting in intermediate XVII. After deprotection of the pyrrolidine nitrogen under suitable conditions, like for example use of HCl in isopropanol in case PG equals tert-butoxycarbonyl, intermediate XVIII 15 formed. Coupling with acids of the general formula R—C(=O)—OH or R'—C(=O)—OH wherein R and R' have the meanings as defined for the compounds of formula I, under conditions as described for the conversion of intermediate IV to intermediate V, results in the formation of a compound of formula I, where R—C(=O)— and R'—C(=O)— are identical.

intermediate XVII equals R—C(=O)— or R'—C(=O)—, and the other is a protecting group like for example tert-butoxycarbonyl, a selective deprotection is possible like shown in the conversion of intermediate XIX (scheme 6) to intermediate XX, or intermediate XXI to intermediate XXII. Intermediates XX and XXII can then be converted to a compound of formula I as described for the conversion of intermediates XVIII to compounds of formula I as illustrated in scheme 5.

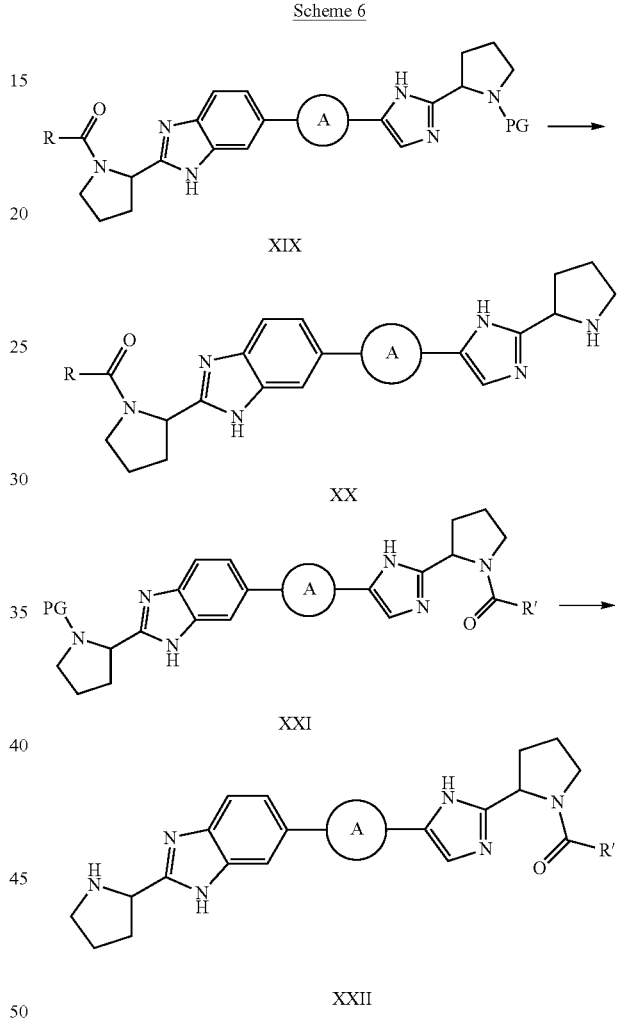

Scheme 6

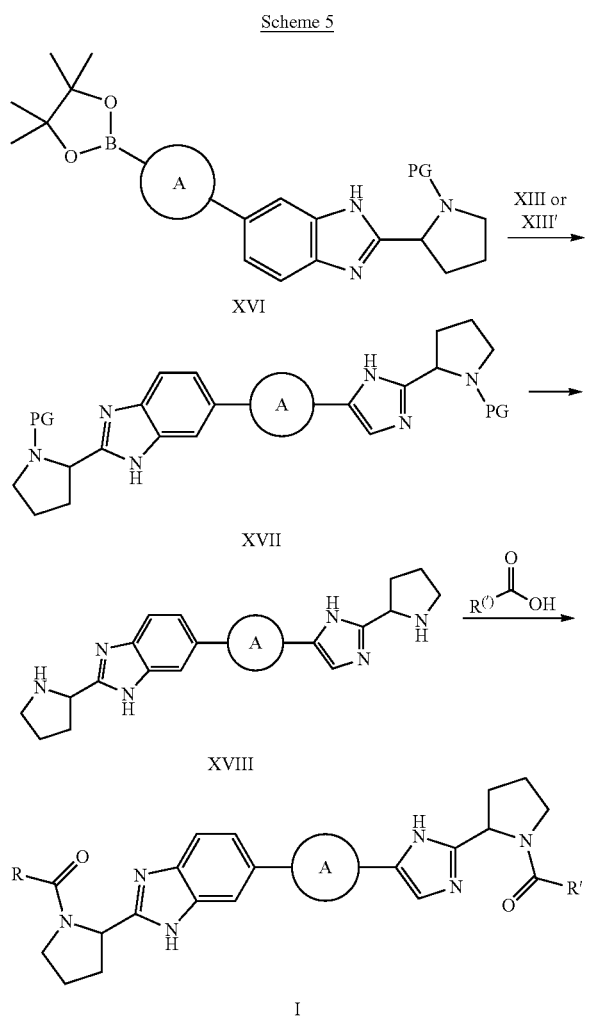

Scheme 5

For the methods illustrated in scheme 4 and 5, where PG is R—C(=O)— or R'—C(=O)—, intermediate XVII is actually a compound of formula I. In case only one PG in The methods illustrated in scheme 4 and first step of scheme 5 may also be used to obtain intermediate compound XXV (Scheme 7) wherein the pyrrolidine groups are orthogonally protected by different protecting groups PG and PG' thereby allowing selective deprotection, resulting in either compound XXVI or XXVII and subsequent acylation with appropriate R'—C(=O)— or R—C(=O)— groups, resulting in compound XXI or XIX' respectively (see scheme 7). In a following step, the second protecting group is removed selectively and the pyrrolidine nitrogen acylated to obtain a compound of formula I. For example, for the purpose of the present invention, such orthogonal protection can be achieved using the t-Boc group on one pyrrolidine in combination with the benzyloxycarbonyl (Cbz) on the other pyrrolidine.

Scheme 7

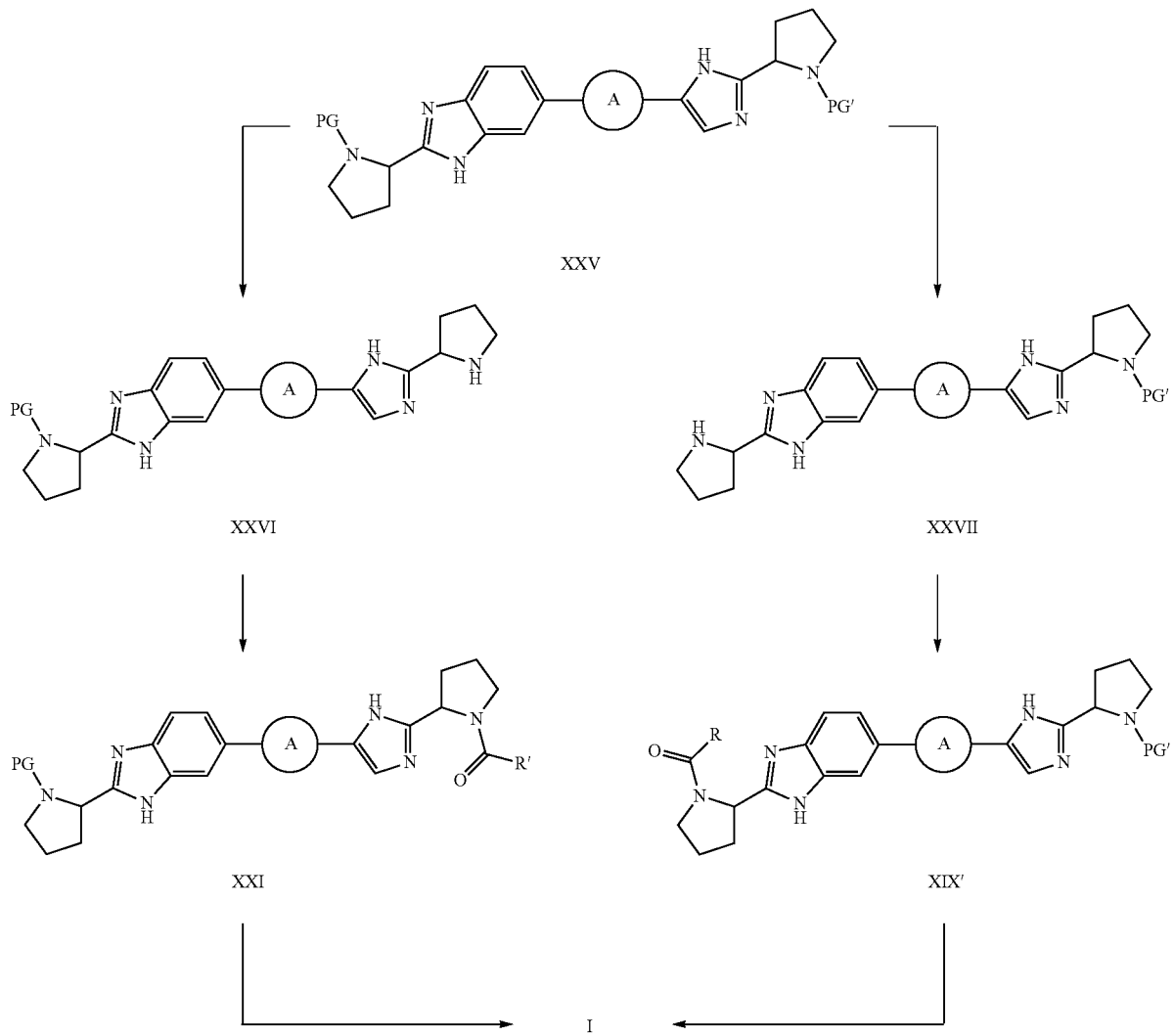

The synthesis procedures as depicted above in schemes 1 to 7 may be performed using racemic proline derivatives, L-proline derivatives or D-proline derivatives. Thereby, compounds of formula I with alternative stereochemistry may be obtained.

In a further aspect, the present invention concerns a pharmaceutical composition comprising a therapeutically or prophylactically effective amount of a compound of formula I as specified herein, and a pharmaceutically acceptable carrier. A prophylactically effective amount in this context is an amount sufficient to prevent HCV infection in subjects being at risk of being infected. A therapeutically effective amount in this context is an amount sufficient to stabilize HCV infection, to reduce HCV infection, or to eradicate HCV infection, in infected subjects. In still a further aspect, this invention relates to a process of preparing a pharmaceutical composition as specified herein, which comprises intimately mixing a pharmaceutically acceptable carrier with a therapeutically or prophylactically effective amount of a compound of formula I, as specified herein.

Therefore, the compounds of the present invention or any subgroup thereof may be formulated into various pharmaceutical forms for administration purposes. As appropriate compositions there may be cited all compositions usually employed for systemically administering drugs. To prepare the pharmaceutical compositions of this invention, an effective amount of the particular compound, optionally in addition salt form, as the active ingredient is combined in intimate admixture with a pharmaceutically acceptable carrier, which carrier may take a wide variety of forms depending on the form of preparation desired for administration. These pharmaceutical compositions are desirable in unitary dosage form suitable, particularly, for administration orally, rectally, percutaneously, or by parenteral injection. For example, in preparing the compositions in oral dosage form, any of the usual pharmaceutical media may be employed such as, for example, water, glycols, oils, alcohols and the like in the case of oral liquid preparations such as suspensions, syrups, elixirs, emulsions and solutions; or solid carriers such as starches, sugars, kaolin, lubricants, binders, disintegrating agents and the like in the case of powders, pills, capsules, and tablets. Because of their ease in administration, tablets and capsules represent the most advantageous oral dosage unit forms, in which case solid pharmaceutical carriers are employed. For parenteral compositions, the carrier will usually comprise sterile water, at least in large part, though other ingredients, for example, to aid solubility, may be included. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed. Also included are solid form preparations intended to be converted, shortly before use, to liquid form preparations. In the compositions suitable for percutaneous administration, the carrier optionally comprises a penetration enhancing agent and/or a suitable wetting agent, optionally combined with suitable additives of any nature in minor proportions, which additives do not introduce a significant deleterious effect on the skin. The compounds of the present invention may also be administered via oral inhalation or insufflation in the form of a solution, a suspension or a dry powder using any art-known delivery system.

It is especially advantageous to formulate the aforementioned pharmaceutical compositions in unit dosage form for ease of administration and uniformity of dosage. Unit dosage form as used herein refers to physically discrete units suitable as unitary dosages, each unit containing a predetermined quantity of active ingredient calculated to produce the desired therapeutic effect in association with the required pharmaceutical carrier. Examples of such unit dosage forms are tablets (including scored or coated tablets), capsules, pills, suppositories, powder packets, wafers, injectable solutions or suspensions and the like, and segregated multiples thereof.

The compounds of formula I are active as inhibitors of the HCV replication cycle and can be used in the treatment and prophylaxis of HCV infection or diseases associated with HCV. The latter include progressive liver fibrosis, inflammation and necrosis leading to cirrhosis, end-stage liver disease, and hepatocellular carcinoma A number of the compounds of this invention moreover are believed to be active against mutated strains of HCV.

The in vitro antiviral activity against HCV of the compounds of formula I can be tested in a cellular HCV replicon system based on Lohmann et al. (1999) Science 285:110-113, with the further modifications described by Krieger et al. (2001) Journal of Virology 75: 4614-4624 and Lohmann et al. (2003) Journal of Virology 77: 3007-3019 for genotype 1b and by Yi et al. (2004) Journal of Virology 78: 7904-7915 for genotype 1a (incorporated herein by reference), which is further exemplified in the examples section. This model, while not a complete infection model for HCV, is widely accepted as the most robust and efficient model of autonomous HCV RNA replication currently available. It will be appreciated that it is important to distinguish between compounds that specifically interfere with HCV functions from those that exert cytotoxic or cytostatic effects in the HCV replicon model, and as a consequence cause a decrease in HCV RNA or linked reporter enzyme concentration. Assays are known in the field for the evaluation of cellular cytotoxicity based for example on the activity of mitochondrial enzymes using fluorogenic redox dyes such as resazurin. Furthermore, cellular counter screens exist for the evaluation of non-selective inhibition of linked reporter gene activity, such as firefly luciferase. Appropriate cell types can be equipped by stable transfection with a luciferase reporter gene whose expression is dependent on a constitutively active gene promoter, and such cells can be used as a counter-screen to eliminate non-selective inhibitors.

Due to their antiviral properties, particularly their anti-HCV properties, the compounds of formula I or any subgroup thereof, are useful in the inhibition of the HCV replication cycle, in particular in the treatment of warm-blooded animals, in particular humans, infected with HCV, and for the prophylaxis of HCV infections. The present invention furthermore relates to a method of treating a warm-blooded animal, in particular human, infected by HCV, or being at risk of infection by HCV, said method comprising the administration of a therapeutically effective amount of a compound of formula I.

The compounds of formula I, as specified herein, may therefore be used as a medicine, in particular as medicine to treat or prevent HCV infection. Said use as a medicine or method of treatment comprises the systemic administration to HCV infected subjects or to subjects susceptible to HCV infection of an amount effective to combat the conditions associated with HCV infection or an amount effective to prevent HCV infection.

The present invention also relates to the use of the present compounds in the manufacture of a medicament for the treatment or the prevention of HCV infection.

In general it is contemplated that an antiviral effective daily amount would be from about 0.01 to about 50 mg/kg, or about 0.01 to about 30 mg/kg body weight. It may be appropriate to administer the required dose as two, three, four or more sub-doses at appropriate intervals throughout the day. Said sub-doses may be formulated as unit dosage forms, for example, containing about 1 to about 500 mg, or about 1 to about 300 mg, or about 1 to about 100 mg, or about 2 to about 50 mg of active ingredient per unit dosage form.

The present invention also concerns combinations of a compound of formula (I) or any subgroup thereof, as specified herein with other anti-HCV agents. The term "combination" may relate to a product or kit containing (a) a compound of formula I, as specified above, and (b) at least one other compound capable of treating HCV infection (herein designated as anti-HCV agent), as a combined preparation for simultaneous, separate or sequential use in treatment of HCV infections. In an embodiment, the invention concerns combination of a compound of formula (I) or any subgroup thereof with at least one anti-HCV agent. In a particular embodiment, the invention concerns combination of a compound of formula (I) or any subgroup thereof with at least two anti-HCV agents. In a particular embodiment, the invention concerns combination of a compound of formula (I) or any subgroup thereof with at least three anti-HCV agents. In a particular embodiment, the invention concerns combination of a compound of formula (I) or any subgroup thereof with at least four anti-HCV agents.

The combination of previously known anti-HCV agents, such as interferon-α (IFN-α), pegylated interferon-α, ribavirin or a combination thereof, and, a compound of formula (I) or any subgroup thereof can be used as a medicine in a combination therapy.

Agents that may be combined with the compounds of the present invention include, for example, nucleoside and non-nucleoside inhibitors of the HCV polymerase, protease inhibitors, helicase inhibitors, NS4B inhibitors and agents that functionally inhibit the internal ribosomal entry site (IRES) and other agents that inhibit HCV cell attachment or virus entry, HCV RNA translation, HCV RNA transcription, replication or HCV maturation, assembly or virus release. Specific compounds in these classes include HCV protease inhibitors such as telaprevir (VX-950), boceprevir (SCH-503034), narlaprevir (SCH-900518), ITMN-191 (R-7227), TMC435350 (TMC435), MK-7009, BI-201335, BI-2061 (ciluprevir), BMS-650032, ACH-1625, ACH-1095, GS 9256, VX-985, IDX-375 (HCV NS4A protease co-factor inhibitor), VX-500, VX-813, PHX-1766, PHX2054, IDX-136, IDX-316, ABT-450, EP-013420 (and congeners) and VBY-376; the nucleoside HCV polymerase inhibitors useful in the invention include R7128, PSI-7851, PSI 7977, IDX-189, IDX-184, IDX-102, R1479, UNX-08189, PSI-6130, PSI-938 and PSI-879 and various other nucleoside and nucleotide analogs and HCV inhibitors including those derived as 2'-C-methyl modified nucleosides, 4'-aza modified nucleosides, and 7'-deaza modified nucleosides, e.g. 4-amino-1-[5-azido-4-hydroxy-5-hydroxymethyl-3-methyl-tetrahydrofuran-2-yl]pyrimidin-2(1H)-one and the bis-2-methylpropanoate ester thereof. Non-nucleoside HCV polymerase inhibitors useful in the invention include HCV-796, HCV-371, VCH-759, VCH-916, VCH-222, ANA-598, MK-3281, ABT-333, ABT-072, PF-00868554, BI-207127, GS-9190, A-837093, JKT-109, GL-59728, GL-60667, ABT-072, AZD-2795 and 13-cyclohexyl-3-methoxy-17,23-dimethyl-7H-10,6-(methanoiminothioiminoethanooxyethanoimino-methano)indolo[2,1-a][2]benzazepine-14,24-dione 16,16-dioxide.

Other anti-HCV agents encompass agents selected from HCV polymerase inhibitors, R-7128, MK-0608, ABT-333, VCH759, PF-868554, GS9190, NM283, VCH-222, VCH-916, BI207217, ABT-072, IDX-102, PSI-7851, PSI-938, valopicitabine, PSI-6130, XTL-2125, NM-107, R7128 (R4048), GSK625433, R803, R-1626, BILB-1941, HCV-796, JTK-109 and JTK-003, ANA-598, IDX-184, MK-3281, MK-1220, benzimidazole derivatives, benzo-1,2,4-thiadiazine derivatives, phenyl-alanine derivatives, A-831 and A-689; HCV proteases (NS2-NS3 and NS3-NS4A) inhibitors, the compounds of WO02/18369 (see, e.g., page 273, lines 9-22 and page 274, line 4 to page 276, line 11), BI-1335, TMC435, MK7009, ITMN-191, MK-7009, BI-201335, SCH900518, VX-813, ABT-450, VBY376, PHX-1766, ACH-1625, BILN-2061, VX-950, BILN-2065, BMS-605339, VX-500, SCH 503034; inhibitors of other targets in the HCV life cycle, including helicase, and metalloprotease inhibitors, ISIS-14803; immunomodulatory agents such as, α-, β-, and γ-interferons such as rIFN-α 2b, rIFN-α 2ba, consensus IFN-α (infergen), feron, reaferon, intermax α, rIFN-β, infergen+actimmune, IFN-omega with DUROS, albuferon, locteron, Rebif, Oral IFN-α, IFN-α 2b XL, AVI-005, pegylated-infergen, pegylated derivatized interferon-α compounds such as pegylated rIFN-α 2b, pegylated rIFN-α 2a, pegylated IFN-β, compounds that stimulate the synthesis of interferon in cells, interleukins, Toll like receptor (TLR) agonists, compounds that enhance the development of type 1 helper T cell response, and thymosin; other antiviral agents such as ribavirin, ribavirin analogs such as rebetol, copegus and viramidine (taribavirin), amantadine, and telbivudine, inhibitors of internal ribosome entry, alpha-glucosidase 1 inhibitors such as MX-3253 (celgosivir) and UT-231B, hepatoprotectants such as IDN-6556, ME-3738, LB-84451 and MitoQ, broad-spectrum viral inhibitors, such as IMPDH inhibitors (e.g., compounds of U.S. Pat. No. 5,807,876, U.S. Pat. No. 6,498,178, U.S. Pat. No. 6,344,465, U.S. Pat. No. 6,054,472, WO97/40028, WO98/40381, WO00/56331, mycophenolic acid and derivatives thereof, and including, but not limited to VX-497, VX-148, and/or VX-944); and other drugs for treating HCV such as zadaxin, nitazoxanide, BIVN-401 (virostat), PYN-17 (altirex), KPE02003002, actilon (CPG-10101), KRN-7000, civacir, GI-5005, ANA-975, XTL-6865, ANA-971, NOV-205, tarvacin, EHC-18, NIM811, DEBIO-025, VGX-410C, EMZ-702, AVI 4065, Bavituximab, and Oglufanide; or combinations of any of the above.

It may be beneficial to develop certain of the above mentioned anti-HCV agents in their prodrug form, in particular the nucleoside analogue HCV polymerase inhibitor. Examples of such prodrug forms could be phosphates, phosphoramidates, or ester forms including mono-esters and di-esters. Such prodrugs require transformation in vivo to the free nucleoside, for example in the gut wall or liver, before intracellular phosphorylation to the active species.

Thus, to combat or treat HCV infections, the compounds of formula (I) or any subgroups thereof may be co-administered in combination with for instance, interferon-α (IFN-α), pegylated interferon-α, ribavirin or a combination thereof, as well as therapeutics based on antibodies targeted against HCV epitopes, small interfering RNA (si RNA), ribozymes, DNAzymes, antisense RNA, small molecule antagonists of for instance NS3 protease, NS3 helicase and NS5B polymerase.

The combinations of the present invention may be used as medicaments. Accordingly, the present invention relates to the use of a compound of formula (I) or any subgroup thereof as defined above for the manufacture of a medicament useful for inhibiting HCV activity in a mammal infected with HCV viruses, wherein said medicament is used in a combination therapy, said combination therapy in particular comprising a compound of formula (I) and at least one other anti-HCV agent, e.g. IFN-α, pegylated IFN-α, ribavirin or a combination thereof.

In a preferred embodiment, the combination of compounds of formula (I), or any subgroup thereof, with another agent that alters HCV viral replication may act synergistically. Interactions of compounds may be analyzed by a variety of mechanistic and empirical methods.

One approach of analyzing such combinations is by three-dimensional graphs and synergistic volume calculations produced by MacSynergy™ II based on the Bliss Independency model (Dr. Mark Pritchard, University of Alabama, Tuscaloosa, Ala.). As such, compounds of the present invention in combination with another agent that alters HCV viral replication are said to act synergistically or have a synergistic effect when values expressed in $nM^2\%$ (volume of synergy) are between 25 and 50 $nM^2\%$ (minor but significant amount of synergy), between 50 and 100 $nM^2\%$ (moderate synergy) or over 100 $nM^2\%$ (strong synergy).

The following examples are meant to illustrate the invention and should not be construed as a limitation of its scope.

EXAMPLES

Example 1

Synthesis of Compounds of Formula XVIIIa (A = 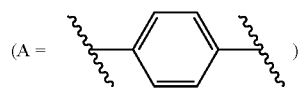 )

1.1 Preparation of Intermediate IIa (PG=Boc; X=Br)

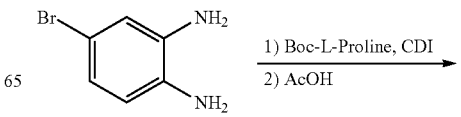

-continued

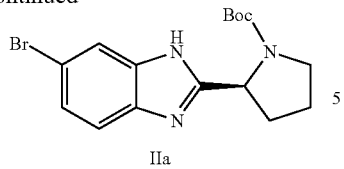

IIa

To a solution of Boc-L-Proline (2669 mg, 12.4 mmol) in pyridine/DMF (30 mL, 1/1) was added di(1H-imidazol-1-yl)ketone (2205 mg, 13.6 mmol). The mixture was stirred at 45° C. for 2 hours. 4-bromobenzene-1,2-diamine (2319 mg, 12.4 mmol) was added and the mixture was stirred at ambient temperature overnight. The solvent was removed and the residue heated in acetic acid (15 mL) at 100° C. for 30 minutes. After concentration of the residue, the mixture was partitioned between ethyl acetate and a saturated sodium bicarbonate solution. The organic phase was separated and washed with water, after drying over $Na_2SO_4$, the mixture was filtrated and the filtrate was concentrated in vacuum. The obtained residue was purified by flash chromatography using $CH_2Cl_2$/EtOAc 90/10 to 50/50, resulting in compound IIa (3.146 g, 69%).

1.1a Preparation of Intermediate IIb (PG=Cbz; X=Br)

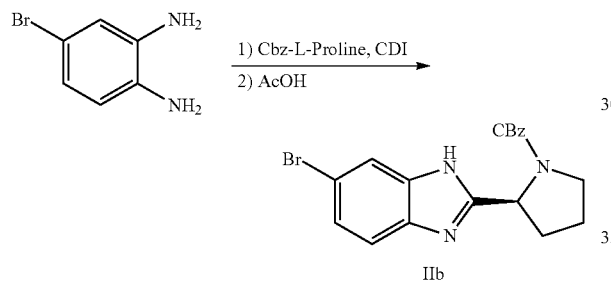

To a stirred solution of N-benzyloxycarbonyl-L-Proline (39.9 g, 160.4 mmol) in dry THF (300 mL) was added CDI (28.6 g, 176.4 mmol). The reaction mixture was stirred at 45° C. for 2 hours. 4-bromo-1,2-diaminobenzene (30 g, 160.4 mmol) was added and the reaction was further stirred for 16 hours at room temperature. The solvent was removed under reduced pressure, the residue was dissolved in acetic acid (100 mL) and stirred in a preheated mantle at 100° C. for 40 minutes. The solvent was then removed under reduced pressure. The obtained residue was dissolved in dichloromethane (500 mL) and water (300 mL). The organic layer was separated from the water layer, washed with 0.5 N HCl (300 mL) followed by saturated $NaHCO_3$-solution (300 mL). After drying with $MgSO_4$ and concentration in vacuum, the product was purified by column chromatography (gradient elution with dichloromethane to 10% EtOAc in dichloromethane) resulting in compound IIb (17.1 g, 25%).

1.2 Preparation of Intermediate IIIa (PG=Boc)

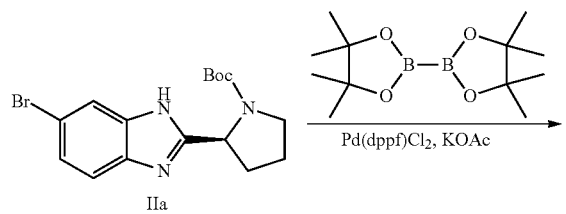

-continued

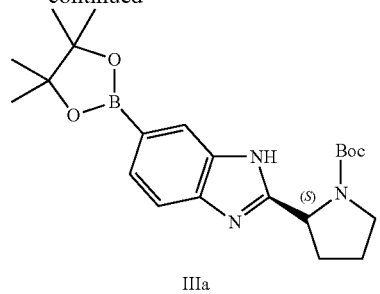

IIIa

To a mixture of IIIa (200 g, 546 mmol), potassium acetate (160.8 g, 1.64 mol) and 4,4,4',4',5,5,5',5'-octamethyl-2,2'-bis(1,3,2-dioxaborolane) (416 g, 1.64 mol) in DMF (3 L) was added $Pd(dppf)Cl_2$ (20 g) under nitrogen gas. The reaction mixture was stirred at 85° C. for 15 hours. The mixture was diluted with ethyl acetate, washed with water and brine, dried over magnesium sulfate, the solids removed by filtration, and the solvents of the filtrate were removed under reduced pressure. The residue was purified by silica column chromatography (petroleum ether:ethyl acetate 10:1 to 2:1) to afford 125 g of IIIa as a white solid (contains 15% of boronic acid).

1.3 Preparation of Intermediate VIIIa (PG = Boc, X = Br; A = <image with para-phenylene> )

Step 1

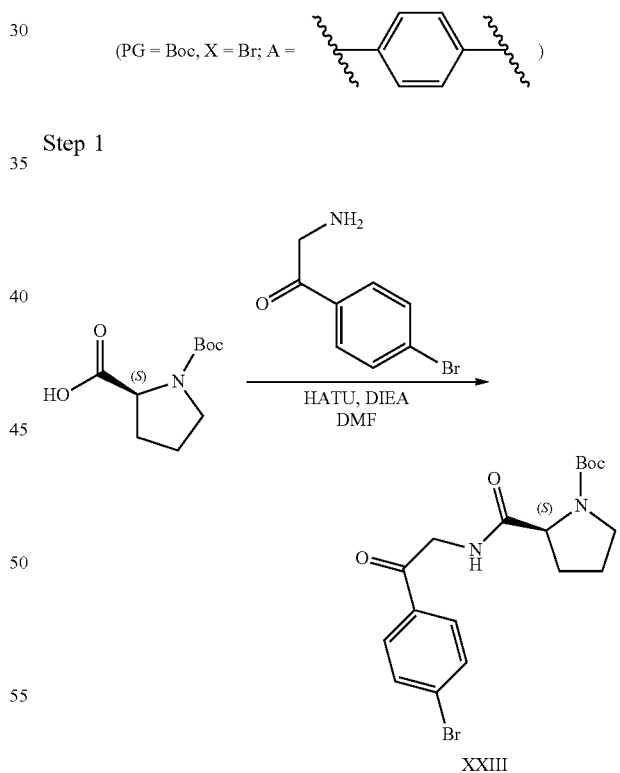

N,N-Diisopropylethylamine (80.0 g, 0.62 mol) was added dropwise, over 30 minutes, to a mixture of aminomethyl-(4-bromo-phenyl)-ketone (50 g, 0.2 mol), 2-(1H-7-azabenzotriazol-1-yl)-1,1,3,3-tetramethyl uronium hexafluorophosphate methanaminium (HATU; 53 g, 0.21 mol), N-Boc-L-Proline (43.0 g, 0.2 mol) in DMF (600 mL). The reaction mixture was stirred at 5° C. for 1 hour. Most of the volatile components were removed in vacuum, and the resulting residue was partitioned between ethyl acetate (600 mL) and water (300 mL). The organic layer was washed with saturated aqueous NaHCO₃ (500 mL) and brine (500 mL), dried over MgSO₄, the solids were removed via filtration and the solvents of the filtrate were removed under reduced pressure. The crude product was purified by column chromatography (silica gel, petroleum ether/ethyl acetate 3:1 to 1:1) to obtain a pale yellow solid, 60 g (62%) of intermediate XXIII.

¹H NMR: (CDCl₃ 400 MHz): δ 7.85 (d, J=8.4 Hz, 2H), 7.66 (d, J=8.4 Hz, 2H), 4.67-4.80 (m, 2H), 4.33-4.41 (m, 1H), 3.42-3.53 (m, 2H), 2.19-2.31 (m, 2H), 1.90-2.00 (m, 2H), 1.50 (s, 9H)

Step 2

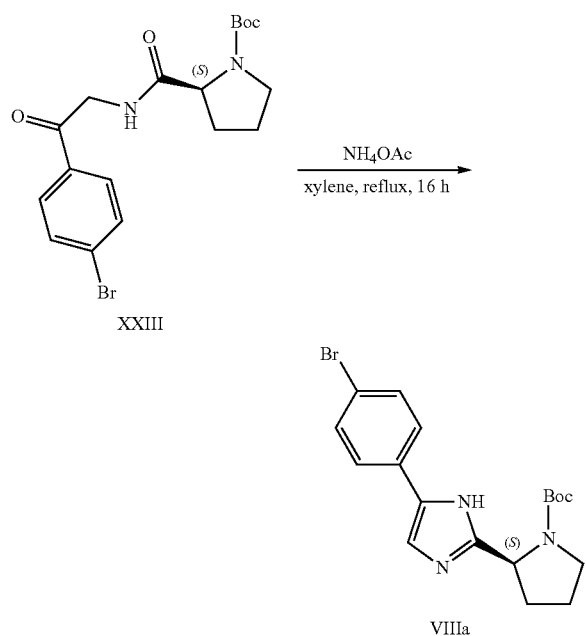

A mixture of intermediate XXIII (60 g, 0.14 mol) and ammonium acetate (89 g, 1.4 mol) in xylene (800 mL) was heated at reflux for 16 hours. The reaction mixture was partitioned between ethyl acetate (700 mL) and saturated NaHCO₃ solution (500 mL). The layers were separated and the aqueous layer was extracted with additional ethyl acetate (2×300 mL). The organic layers were combined, washed with brine (500 mL), dried over MgSO₄, the solids removed via filtration and the solvents of the filtrate were evaporated under reduced pressure. The resulting material was recrystallized from ethyl acetate/petroleum ether to afford a yellow solid, VIIIa, 25 g (43%).

¹H NMR: (CD₃OD 400 MHz): δ 7.62 (d, J=8.4 Hz, 2H), 7.51 (d, J=8.4 Hz, 2H), 7.31-7.36 (m, 1H), 4.93-4.98 (m, 1H), 3.66-3.70 (m, 1H), 3.48-3.54 (m, 1H), 2.29-2.41 (m, 1H), 1.93-2.17 (m. 3H), 1.48 (s, 3H), 1.27 (s, 6H).

1.4 Preparation of Intermediate XVIIa (PG = Boc, A =  ))

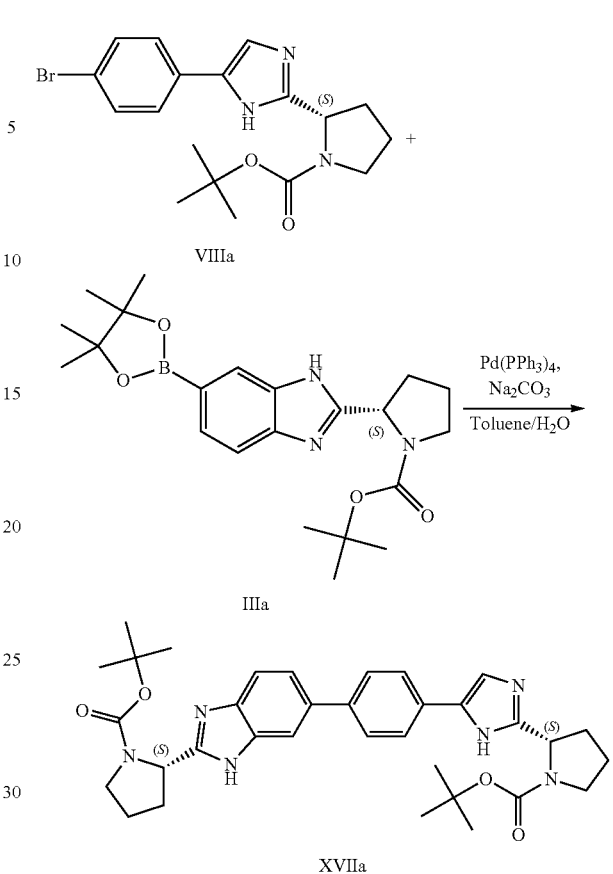

To VIIIa (1138 mg, 2.90 mmol) and tetrakis(triphenylphosphine)palladium (140 mg, 0.121 mmol) in toluene under a nitrogen atmosphere, 2 M Na₂CO₃ (2.5 mL, 5.0 mmol) and compound IIIa (1.0 g, 2.42 mmol) in methanol were added. The vigorously stirred mixture was warmed to 80° C. under a nitrogen atmosphere and stirred at this temperature overnight.

After cooling to room temperature, CH₂Cl₂ (15 mL) was added followed by water (10 mL). The organic layer was separated and the water layer extracted with CH₂Cl₂. The combined organic layers were dried over Na₂SO₄ and after filtration, concentrated to dryness under reduced pressure to afford a brown residue. This residue was purified by column chromatography with CH₂Cl₂ to CH₂Cl₂/methanol 90/10 as eluent, resulting in compound XVIIa (878 mg, 61%).

1.5 Preparation of Intermediate XVIIIa (A = 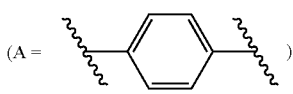 )

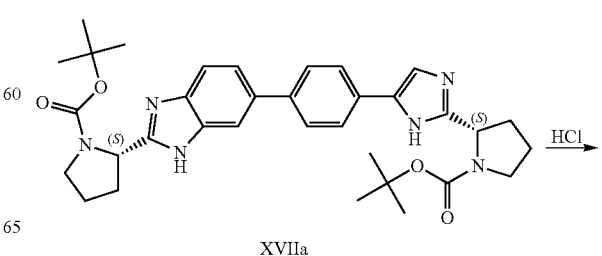

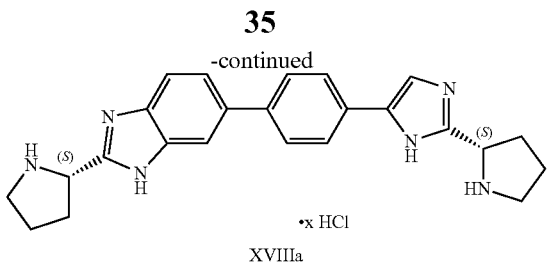

·x HCl

XVIIIa

To a solution of XVIIa (878 mg, 1.47 mmol) in isopropanol (5 mL) was added HCl (5-6 M in isopropanol, 15 mL). The mixture was stirred at room temperature overnight. The solvent was evaporated, the obtained solid XVIIIa was dried in vacuum and used as such in the next step.

Example 2

Synthesis of Compounds of Formula XVIIIb

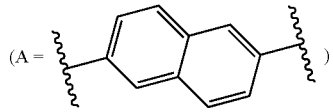

2.1 Preparation of L-boc-prolinol

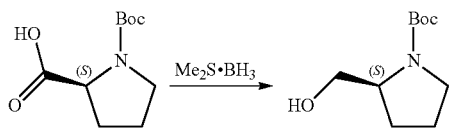

Borane-methyl sulfide complex (180 mL, 1.80 mol) was added dropwise to a solution of N-Boc-L-Proline (300 g, 1.39 mol) in anhydrous THF (3.0 L) which was cooled to 0° C. When gas evolution ceased, the ice bath was removed and the solution was stirred at 10° C. for 18 hours. Thin layer chromatography (TLC) showed that no starting material remained and that the desired product was formed. The solution was cooled to 0° C. and methanol (2.4 L) was slowly added. The solvents were removed under reduced pressure. The residue was reconstituted in dichloromethane (1 L), washed with NaHCO$_3$ (500 mL, saturated, aqueous) and brine (500 mL), dried over MgSO$_4$, the solids were removed via filtration, and the solvents of the filtrate were removed under reduced pressure to afford a white solid, 260 g (93%), used in the next step without further purification.

2.2 Preparation of L-boc-prolinal

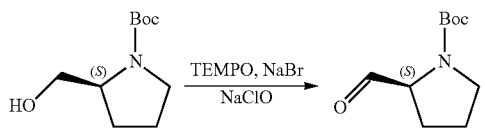

To a solution of L-boc-prolinol (100 g, 500 mmol) in CH$_2$Cl$_2$ (1.5 L) at 0° C. were added successively, under vigorous stirring, 2,2,6,6-tetramethylpiperidine-1-oxyl (TEMPO; 1.56 g, 10 mmol) and NaBr (5.14 g, 50 mmol). To the resulting mixture was added dropwise a solution of NaHCO$_3$ (6.3 g, 75 mmol) and 6% NaClO in active chlorine (750 mL, 750 mmol) at 0° C. over a period of 1 hour. TLC showed no starting material remained and that the desired product was formed. The mixture was rapidly extracted with dichloromethane (2×1.5 L). The organic layers were combined, washed with NaHSO$_4$ (10%, 1 L) and KI (4%, 200 mL), then with Na$_2$S$_2$O$_3$ (10%, 1 L) and brine (1.5 L), dried over MgSO$_4$, the solids were removed via filtration, and the solvents evaporated to afford a yellow oil, L-boc-prolinal, (89 g, 92%), used in the next step without further purification.

2.3 Preparation of Intermediate XXIV

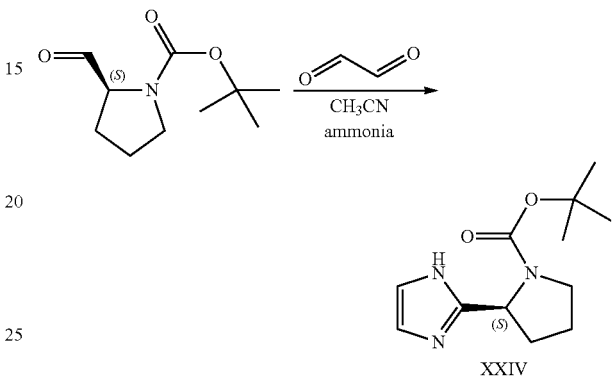

Aqueous ammonia (25~28%, 200 mL) was added dropwise to a solution of L-boc-prolinal (89 g, 0.44 mol) and glyoxal (183 mL of 40% in water) in methanol (1 L). The reaction mixture was sealed and reacted at 10° C. After 16 hours, additional glyoxal (20 mL) and aqueous ammonia (20 mL) were added and reacted for an additional 6 hours. The solvents were removed under reduced pressure, and the crude was reconstituted in ethyl acetate (1.0 L), washed with water and brine, dried over MgSO$_4$, the solids were removed via filtration and the solvents were removed under reduced pressure. The crude was purified by column chromatography (silica gel, dichloromethane to methanol/dichloromethane 1:70) to obtain 73 g (70%) intermediate XXIV as a white solid.

$^1$H NMR: (CD$_3$OD 400 MHz) δ 6.95 (s, 2H), 4.82-4.94 (m, 1H), 3.60-3.70 (m, 1H), 3.41-3.50 (m, 1H), 2.20-2.39 (m, 1H), 1.91-2.03 (m, 3H), 1.47 (s, 3H), 1.25 (s, 6H)

2.4 Preparation of Intermediate XIIIa (PG=Boc)

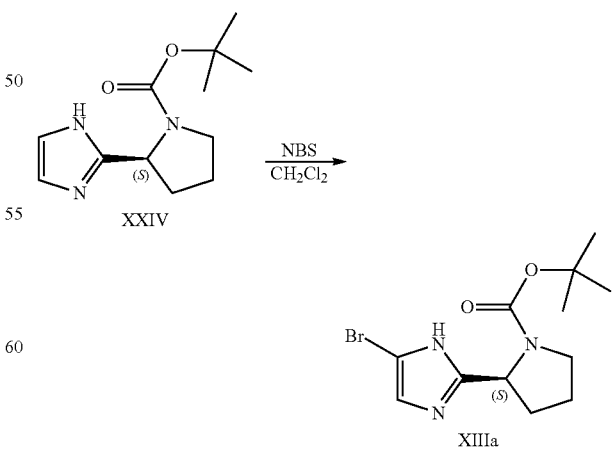

N-Bromosuccinimide (47.2 g, 0.26 mol) was added portion wise over 1 hour to a cooled (ice-ethanol bath, −10° C.) solution of XXIV (63.0 g, 0.26 mol) in CH$_2$Cl$_2$ (1.5 L) and stirred at similar temperature for 2 hours. The reaction mixture was concentrated in vacuum and the residue was purification by preparatory HPLC to provide 25.3 g (30%) of XIIIa as a pale yellow solid.

$^1$H NMR: CD$_3$OD 400 Mhz

δ 6.99-7.03 (s, 1H), 4.77-4.90 (m, 1H), 3.61-3.68 (m, 1H), 3.42-3.50 (m, 1H), 2.20-2.39 (m, 1H), 1.89-2.05 (m, 3H), 1.47 (s, 3H), 1.27 (s, 6H).

2.4a Preparation of Intermediate XIII'a (PG=Boc)

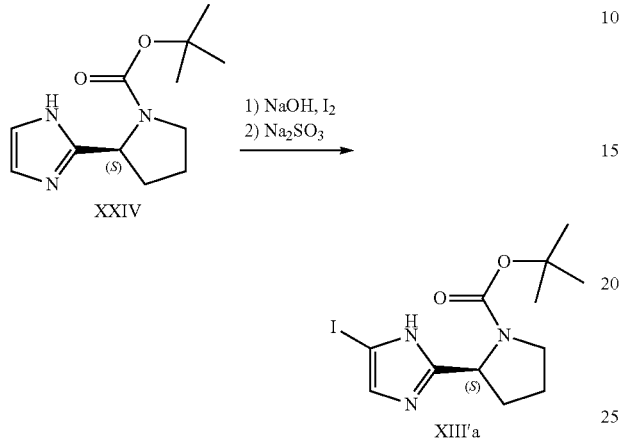

To a solution of iodine (43.3 g, 170.5 mmol, 2 eq) in chloroform (210 mL) in a round bottomed flask (1 L) a suspension of XXIV (20 g, 84.3 mmol) in an aqueous NaOH solution (2M, 210 mL) was added. The mixture was stirred at room temperature for 15 hours. To the resulting reaction mixture was added a saturated aqueous Na$_2$S$_2$O$_3$ solution (100 mL) and the organic layer was separated. The aqueous layer was extracted with chloroform (4×150 mL). The organic layers were combined, washed with water and dried on magnesium sulphate. The solids were filtered and the solution was evaporated to dryness to afford diiodide (38.61 g, 89%).

The above obtained intermediate diiodide (2.24 g, 4.58 mmol) and sodium sulfite (4.82 g, 38 mmol) were placed in a round bottomed flask (100 mL) and suspended in 30% EtOH/water (80 mL). The resulting mixture was refluxed for 40 hours. The solvent was removed and after addition of H$_2$O (20 mL), the mixture was stirred at room temperature overnight. The solids were filtered, washed with water and dried in a vacuum oven to afford compound XIII'a (1.024 g, 61%).

$^1$H NMR (400 MHz, DMSO-d$_6$) δ ppm 1.16 and 1.38 (2× br. s., 9H), 1.68-2.02 (m, 3H), 2.02-2.27 (m, 1H), 3.18-3.38 (m, 1H), 3.38-3.59 (m, 1H), 4.53-4.88 (m, 1H), 6.81 (m, ~0.1H), 7.05-7.28 (m, ~0.9H), 11.90-12.20 (m, ~0.9H), 12.22-12.40 (m, −0.1H)

2.5 Preparation of Intermediate XVb

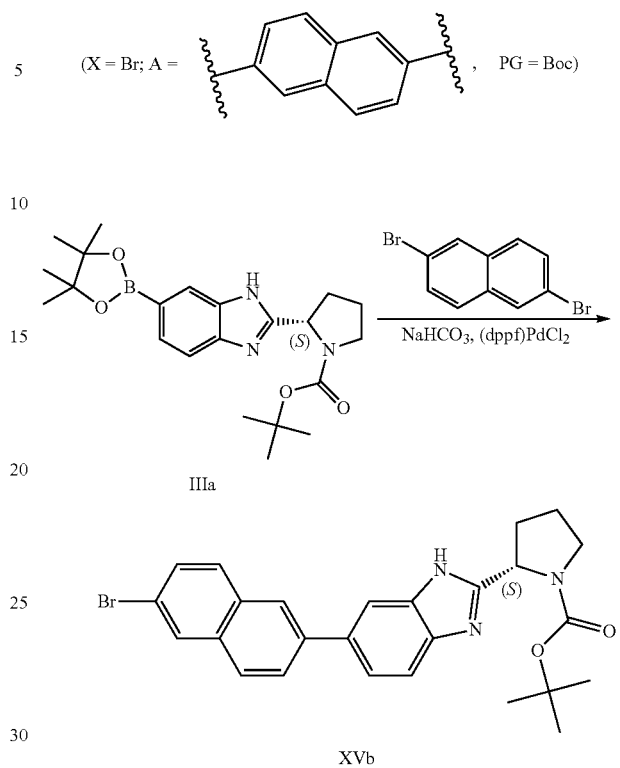

2,6-Dibromonaphthalene (6.92 g, 24.2 mmol), boronic ester IIIa (2 g, 4.84 mmol), NaHCO$_3$ (813 mg, 9.68 mmol), (dppf)PdCl$_2$ (710 mg, 0.968 mmol) were dissolved in toluene (75 mL). Water (1 mL) was added and the mixture was heated for 7 hours at reflux. The solids were removed by filtration over dicalite and the filtrate was evaporated to dryness on silica. The residue was purified by column chromatography by gradient elution with heptane to ethylacetate. The appropriate fractions were pooled and the solvent was removed under reduced pressure. The residue (1.89 g, 79%) was used as such in the next step.

2.6 Preparation of Intermediate XVIb

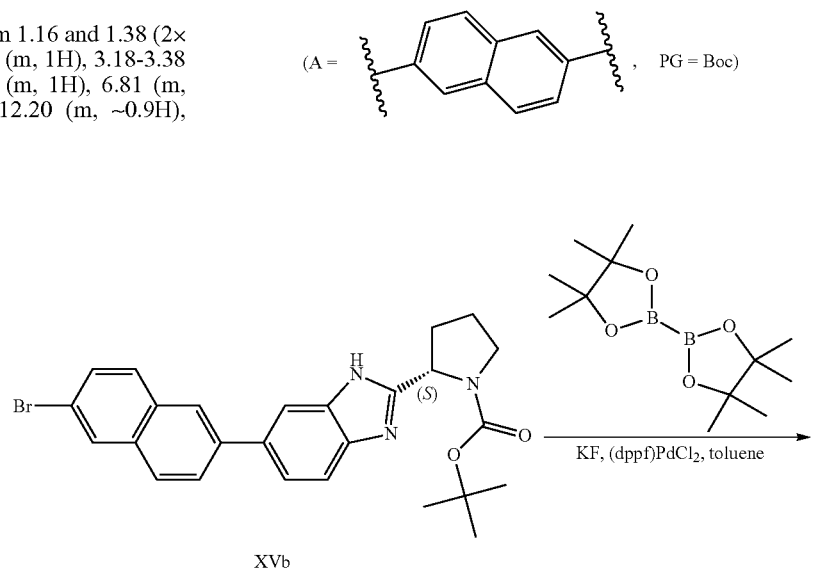

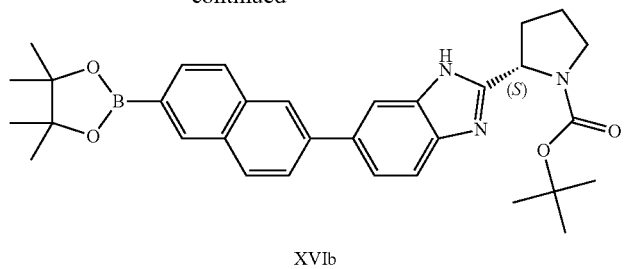

XVIb

Bromide XVb (1890 mg, 3.83 mmol), 4,4,4',4',5,5,5',5'-octamethyl-2,2'-bis(1,3,2-dioxaborolane) (2437 mg, 9.59 mmol), KF (390 mg; 6.71 mmol) and (dppf)PdCl$_2$ (281 mg, 0.384 mmol) were dissolved in toluene (50 mL) and heated 3 days at reflux.

The solids were removed by filtration over dicalite and the filtrate was evaporated to dryness on silica. The residue was purified by column chromatography using a heptane to ethylacetate gradient. The fractions containing the product were pooled and the solvent was removed under reduced pressure. The residue (1.22 g, 59%) was used as such in the next reaction 2.6a Alternative Preparation of Intermediate XVIb

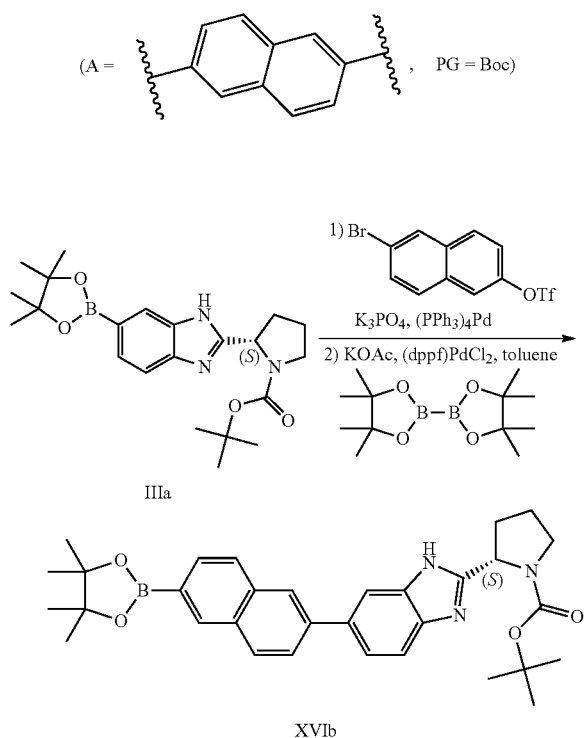

Under nitrogen, IIIa (25 g, 60.5 mmol), 6-bromonaphthalen-2-yl trifluoromethane-sulfonate (20 g, 56.7 mmol), K$_3$PO$_4$ (36.65 g, 173 mmol) and (PPh$_3$)$_4$Pd (717 mg, 0.62 mmol) were stirred in THF (60 mL) and water (15 mL) with the heating mantle at 85° C. (reflux) for 2 hours. CH$_2$Cl$_2$ (50 mL) was added and the water layer was separated. The organic layer was dried on MgSO$_4$ and after filtration, the filtrate was concentrated resulting in a sticky solid. The residue was purified by column chromatography (petroleum ether/Ethyl acetate 15/1 to 1/1) to afford XVb (20 g; 40.6 mmol). Compound XVb (1 g, 2.0 mmol), potassium acetate (0.5 g, 5.0 mmol), 4,4,4',4',5,5,5',5'-octamethyl-2,2'-bis(1,3,2-dioxaborolane) (1.29 g, 5.0 mmol), and Pd(dppf)Cl$_2$ (0.1 g) were stirred in DMF (15 mL) under argon. The mixture was heated at 60° C. for 5 hours. After cooling, CH$_2$Cl$_2$ (50 mL) was added and the mixture was washed with saturated NaHCO$_3$. The water layer was separated and extracted with CH$_2$Cl$_2$. The organic layers were combined and dried on MgSO$_4$. After filtration the solvent was removed and the product was purified by column chromatography (gradient elution with petroleum ether/ethyl acetate 10/1 to 1/1) to give of XVIb (0.7 g, 1.3 mmol, 65%) as light yellow solid.

2.6b Preparation of Intermediate VIIIb

Step 1

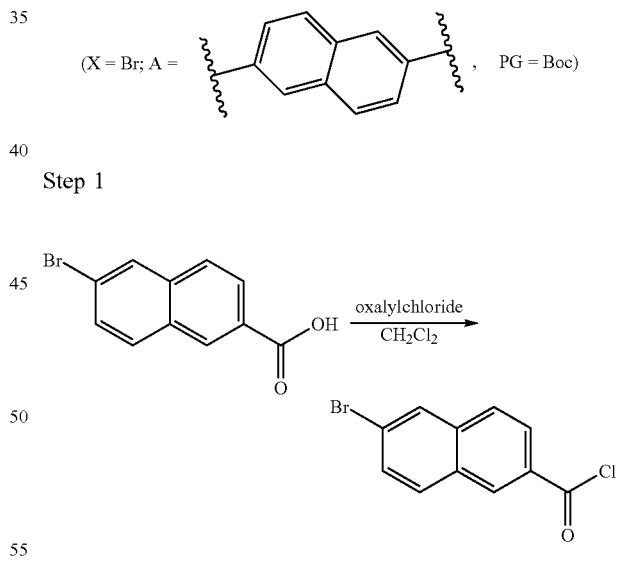

6-bromo-2-naphthoic acid (72.3 g, 282 mmol, 1.0 equiv.) was suspended in dichloromethane (600 mL) and DMF (catalytic, 5 drops) was added. Oxalylchloride (71.6 g, 564 mmol, 2.0 equiv.) was added portion wise during 1 hour. The reaction mixture was stirred overnight with a CaCl$_2$ drying tube mouthed on the flask. Complete dissolution occurred. The reaction mixture was concentrated, dichloromethane (100 mL) was added and the solvent was evaporated again, yielding 6-bromo-2-naphthoyl chloride (76.1 g, 100%) as an oil which was used as such in next step.

Step 2

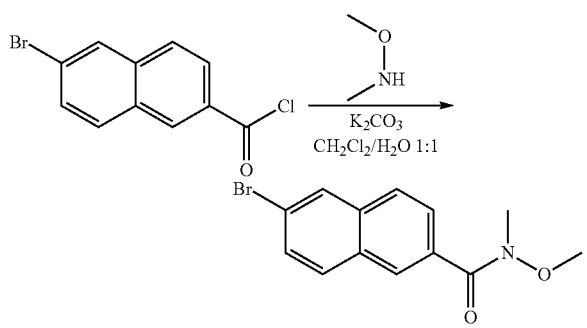

N,O-Dimethylhydroxylamine Hydrochloride (41.3 g, 423 mmol, 1.5 equiv.) was dissolved in distilled water (200 mL) and potassium carbonate (117 g, 3.0 equiv.) was added portion wise ($CO_2$ evolution). Water (300 mL) and dichloromethane (200 mL) was added and a solution of 6-bromo-2-naphthoyl chloride (76.1 g, 282 mmol, 1.00-equiv.) in dichloromethane (300 mL) was added portion wise to this mixture while stirring. The reaction mixture was stirred 1 hour. The organic layer was separated, dried over sodium sulphate, filtrated, concentrated and dried in vacuum overnight, yielding 6-bromo-N-methoxy-N-methyl-2-naphthamide (82.9 g, 100%) as a brown solid.

Step 3

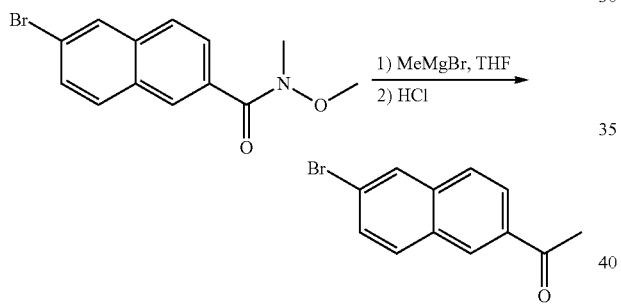

6-bromo-N-methoxy-N-methyl-2-naphthamide (82.9 g, 282 mmol, 1 equiv.) was dissolved in tetrahydrofurane (600 mL) in a 4-neck flask under nitrogen. The reaction mixture was cooled in an ice bath and methyl magnesium bromide (3.2 M in methyl-tetrahydrofurane, 197 mL, 2.2 equiv.) was added drop wise during 1 hour, while maintaining the temperature of the reaction mixture between 10-15° C. The reaction mixture was stirred 30 minutes further in an ice bath. Aqueous hydrochloric acid (2 M, 100 mL) was then carefully added drop wise while cooling on an ice bath. The organic solvent was evaporated and the precipitated product extracted with dichloromethane (500 mL). The solution was dried over sodium sulphate, filtered and concentrated. The solid residue was dried in vacuum at 40° C. yielding 1-(6-bromonaphthalen-2-yl)-ethanone (70.6 g, 99%).

Alternative for Preparation of
1-(6-bromonaphthalen-2-yl)ethanone

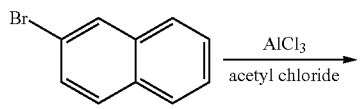

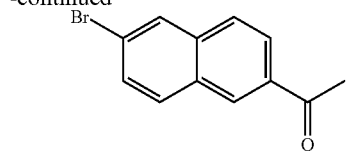

A mixture of 2-bromonaphthalene (41.4 g, 200 mmol), acetyl chloride (11.3 mL, 160 mmol), nitrobenzene (250 mL) and $AlCl_3$ (28 g, 210 mmol) was stirred for 4 hours at 100° C. (oil bath temperature). The resulting reaction mixture was cooled, poured onto ice/water (100 mL) and filtered. The filtrate was washed with water (100 mL). The solvent (nitrobenzene) was removed by distillation. The resulting residue was crystallized from hexane to afford 18 g of desired product (36% yield).

1-(6-bromonaphthalen-2-yl)ethanone: $^1$H NMR (400 MHz, ACETONITRILE-$d_3$) δ ppm 2.66 (s, 3H) 7.66 (dd, J=8.8, 2.0 Hz, 1H) 7.86 (d, J=8.8 Hz, 1H) 7.94 (d, J=8.8 Hz, 1H) 8.02 (dd, J=8.8, 1.8 Hz, 1H) 8.13 (d, J=2.0 Hz, 1H) 8.53 (d, J=1.8 Hz, 1H).

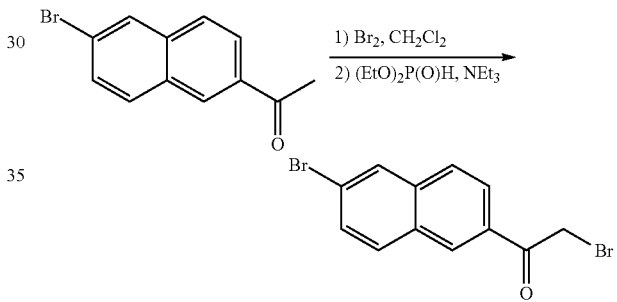

Step 4

1-(6-bromonaphthalen-2-yl)ethanone (55.6 g, 223 mmol, 1.0 equiv.) was dissolved in dichloromethane (1.3 L). Dibromine (78.3 g, 490 mmol, 2.2 equiv.) was added drop wise during 30 minutes. The reaction mixture was stirred 1 hour and concentrated to afford 2,2-dibromo-1-(6-bromonaphthalen-2-yl)ethanone as a solid which was used as such in next step.

2,2-dibromo-1-(6-bromonaphthalen-2-yl)ethanone (90.0 g, 221 mmol, 1.00) was dissolved in tetrahydrofurane (800 mL), triethylamine (27.67 mL, 199 mmol, 0.9 equiv.) was added followed by diethyl phosphite (45.8 g, 332 mmol, 1.50 equiv.). The reaction mixture was stirred overnight. The reaction mixture was filtrated and the solvent was removed in vacuum. The obtained residue was dissolved in ethyl acetate (1.2 L) and washed with water. The organic layer was separated, dried over sodium sulphate, filtrated and concentrated to yield crude 2-bromo-1-(6-bromonaphthalen-2-yl)ethanone (70.3 g). Recrystallization from acetonitrile gave 30 g (first batch) and 6.5 g (second batch) of 2-bromo-1-(6-bromonaphthalen-2-yl)ethanone (50%)

Step 5

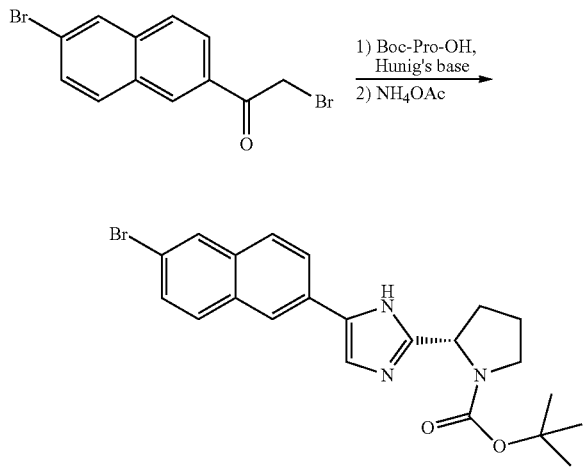

2-bromo-1-(6-bromonaphthalen-2-yl)ethanone (4.9 g, 14.9 mmol, 1 equiv.) was suspended in acetonitrile (150 mL) at 20°. (L)-Boc-Proline (3.22 g, 14.9 mmol, 1 equiv.) was added followed by N-ethyl-N-isopropylpropan-2-amine (2.83 mL, 16.4 mmol, 1.10 equiv.) The reaction mixture was stirred at 20° C. for 30 minutes. The reaction mixture was concentrated. The residue was dissolved in dichloromethane and washed successively with aqueous hydrochloric acid (1%, 100 mL) and aqueous NaHCO₃ solution. After drying over sodium sulphate, filtration and concentration, the residual oil (6.52 g, 94%) was used as such in the next step.

Ammonium acetate (16.3 g, 212 mmol, 15 equiv.) was added to the compound obtained above (6.52 g, 14.1 mmol, 1.00 equiv.) dissolved in toluene (150 mL) and the mixture was refluxed overnight. The reaction mixture was concentrated and the residue was crystallized from acetonitrile (100 mL). The crystals were filtered off and dried in vacuum at 40° C. to afford VIIIb (3.2 g, 51%).

2.6c Preparation of Intermediate IXb

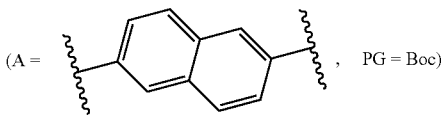

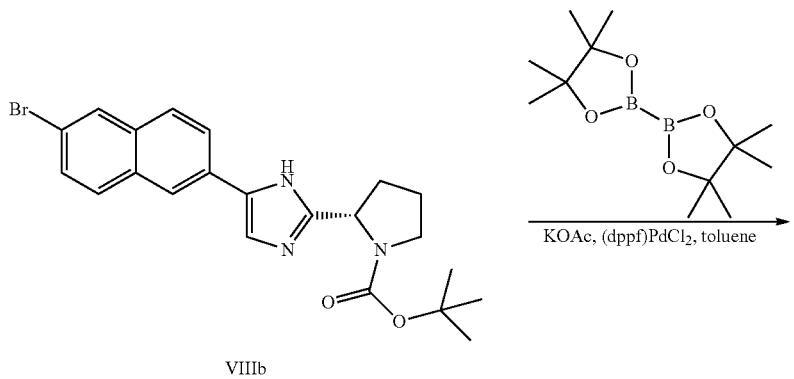

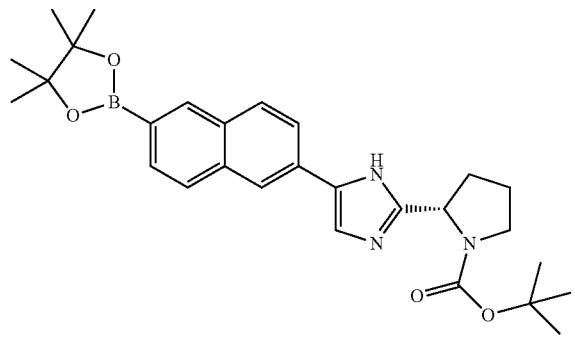

VIIIb (3.076 g, 6.95 mmol), bispinacolatodiboron (2.648 g, 10.43 mmol), potassium-acetate (1.365 g, 13.91 mmol) and PdCl$_2$(dppf) (254 mg, 0.348 mmol) are dissolved in toluene (30 mL) and heated for 17 hours at 85° C. under argon. The reaction mixture was cooled to room temperature, dichloromethane (50 mL) was added and the mixture was washed with saturated NaHCO$_3$ solution. The organic phase was dried over MgSO$_4$, filtrated, concentrated in vacuum and purified by silicagel column chromatography (gradient elution from 20 to 50% EtOAc in heptane) to yield IXb (2.63 g, 77%). The product can be precipitated from hexane/i-Pr$_2$O (3/2)

2.6d Preparation of Intermediate VIIIc

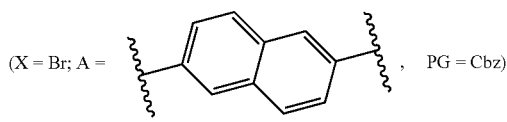

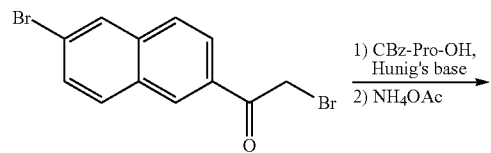

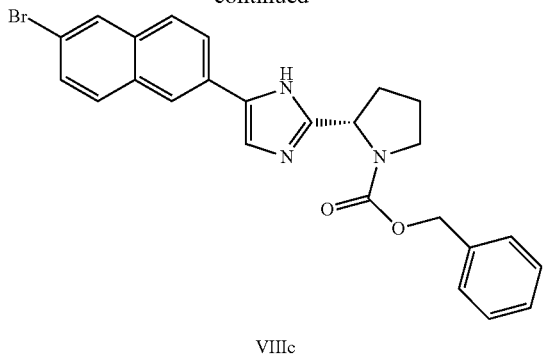

VIIIc

To a solution of 2-bromo-1-(6-bromonaphthalen-2-yl)ethanone (57.7 g, 175.9 mmol, 80% pure) in acetonitrile (1 L), L-Cbz-Proline (43.8 g, 175.9 mmol) was added, followed by diisopropylethylamine (33.4 mL, 193.5 mmol) and the reaction was stirred 40 minutes at room temperature. The solvent then was removed under reduced pressure and the obtained residue was redissolved in dichloromethane (500 mL), washed with 1% HCl (500 mL) and aqueous saturated NaHCO$_3$ (500 ml). The organic phase was dried with MgSO$_4$, filtrated and the solvent was removed under reduced pressure resulting in a brown oily residue (80 g) which was used as such in next step. Part of the above residue (69.8 g, 140.6 mmol) and ammoniumacetate (162.6 g, 2.11 mol) were stirred in toluene and refluxed overnight. The reaction mixture was cooled to room temperature and the solvent was removed under reduced pressure. The obtained residue was stirred in a mixture of dichloromethane and water (1/1, 1500 mL) to precipitate compound VIIIc. After filtering and rinsing with water, compound VIIIc (61.3 g, 92%) was obtained as a white powder.

$^1$H NMR (400 MHz, DMSO-d$_6$) δ ppm 1.84-2.38 (m, 4H), 3.42-3.56 (m, 1H), 3.58-3.73 (m, 1H), 4.84-5.20 (m, 3H), 6.97-7.46 (m, 5H), 7.54-7.60 (m, 1H), 7.63-7.71 (m, 1H), 7.83-7.91 (m, 2H), 7.95-8.05 (m, 1H), 8.10-8.16 (m, 1H), 8.22-8.37 (m, 1H), 11.92-12.44 (m, 1H)

2.7 Preparation of Intermediate XVIIb

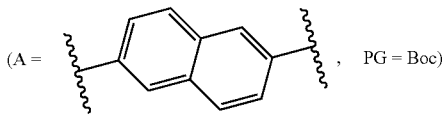

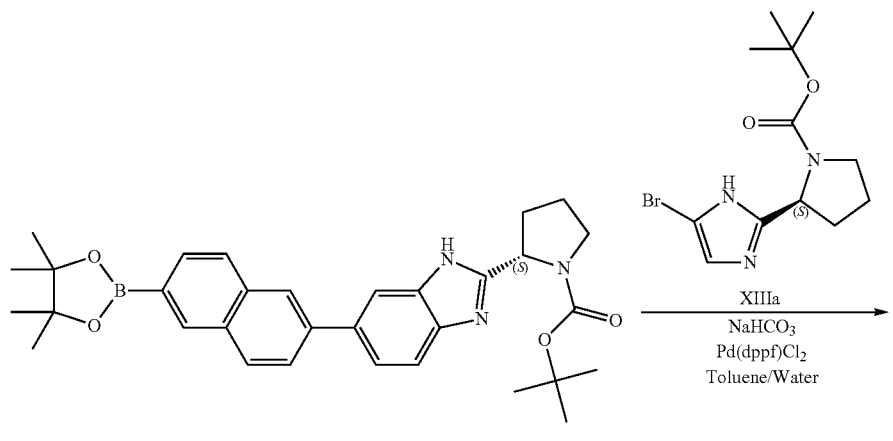

XVIb

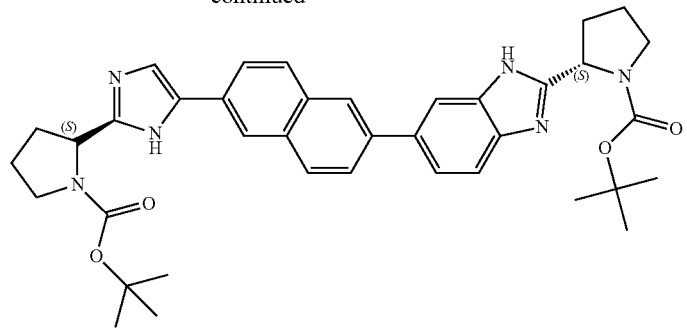

XVIIb

To boronic ester XVIb (1.22 g, 2.26 mmol), bromide XIIIa (1072 mg, 3.39 mmol), sodium bicarbonate (380 mg, 4.52 mmol), Pd(dppf)Cl$_2$ (166 mg, 0.226 mmol) in toluene (50 mL), was added water (1 mL). The resulting mixture was heated at reflux overnight. The reaction mixture was filtered, evaporated to dryness and purified by column chromatography by gradient elution with heptane to ethyl acetate. The collected fractions containing the product were pooled and the volatiles were removed under reduced pressure. The residue (960 mg, 65%) was used as such in the next reaction.

2.7a Alternative Preparation of Intermediate XVIIb

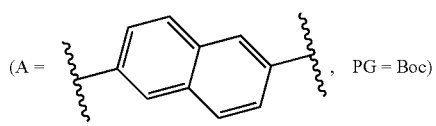 [SMILES: *c1ccc2cc(*)ccc2c1]

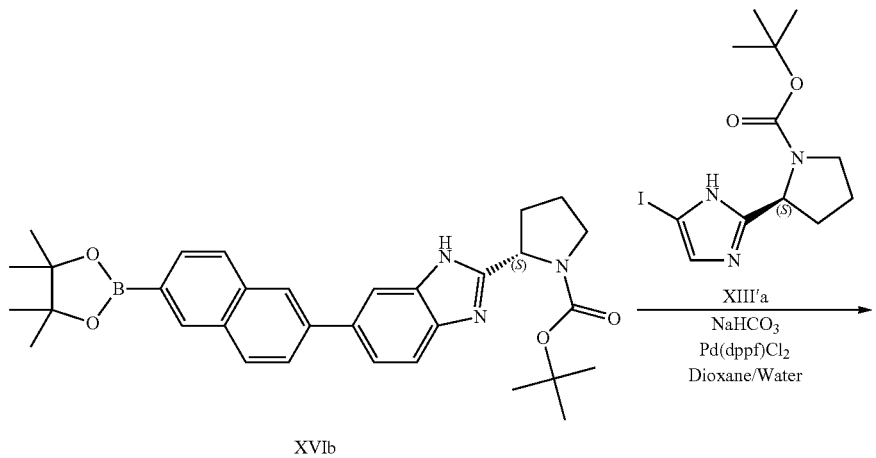

XVIb

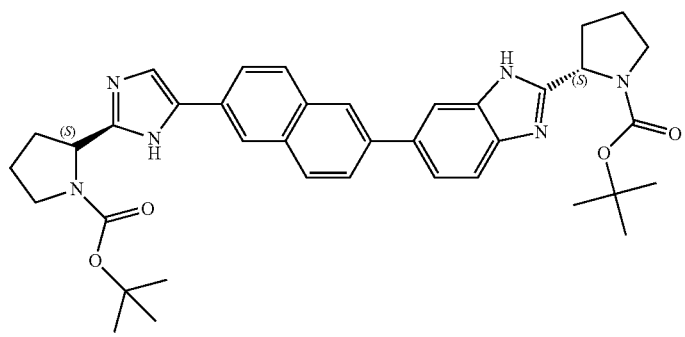

XVIIb

XVIb (10 g, 18.5 mmol), XIII'a (8.76 g, 24 mmol), NaHCO$_3$ (9.32 g, 111 mmol) and Pd(dppf)Cl$_2$ (1 g) were stirred in dioxane/water (140 mL, 6/1) under argon. The mixture was heated to 85° C. for 15 hours. Brine (100 mL) was added and the mixture was extracted with CH$_2$Cl$_2$, after drying on MgSO$_4$, filtration and evaporation of the solvent, the residue was purified by column chromotography by gradient elution with CH$_2$Cl$_2$ to EtOAc to afford XVIIb (7 g, 58%).

2.7b Alternative Preparation of Intermediate XVIIb

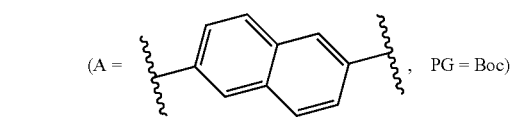 [SMILES: *c1ccc2cc(*)ccc2c1]

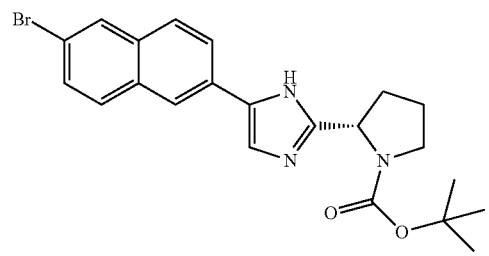

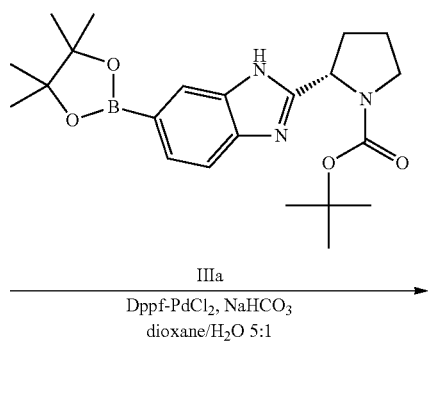

matography (gradient elution with 0-6% MeOH in CH$_2$Cl$_2$) to afford XVIIb (19.52 g, 65%) as an off-white powder.

2.8 Preparation of Intermediate XVIIIb

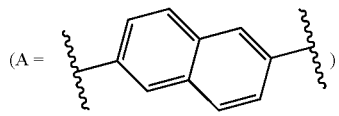

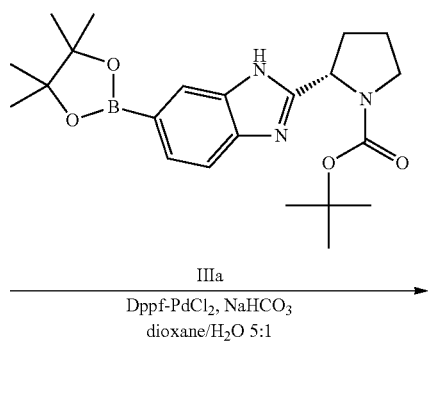

To a stirred, deoxygenated solution of VIIIb (20.0 g, 45.2 mmol, 1.00 equiv.), IIIa (20.6 g, 49.7 mmol, 1.1 equiv.) and sodium bicarbonate (11.4 g, 136 mmol, 3.0 equiv.) in 1,4-dioxane/water (500 mL, 5:1) under nitrogen, was added 1,1'-Bis(diphenyl-phosphino)ferrocene-palladium(II)dichloride dichloromethane complex (2.50 g, 4.52 mmol, 0.1 equiv.). The mixture was heated at 80° C. under argon for 15 hours and cooled to room temperature. The reaction mixture was diluted with dichloromethane (500 mL) and washed with brine (2×150 mL) dried on magnesium sulphate; filtered and evaporated to dryness to afford a dark brown foam (43 g). The foam was purified using silicagel column chro- -continued

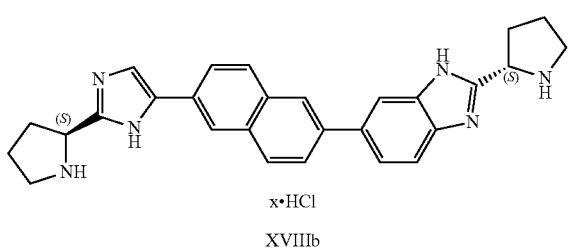

To a solution of XVIIb (960 mg, 1.48 mmol) in CH$_2$Cl$_2$ (25 mL) was added HCl (5-6 M in isopropanol, 5 mL). The mixture was stirred at room temperature overnight. The solvent was evaporated, the obtained solid was dried in vacuum and used as such in the next step.

2.8a Alternative Preparation of Intermediate XVIIIb

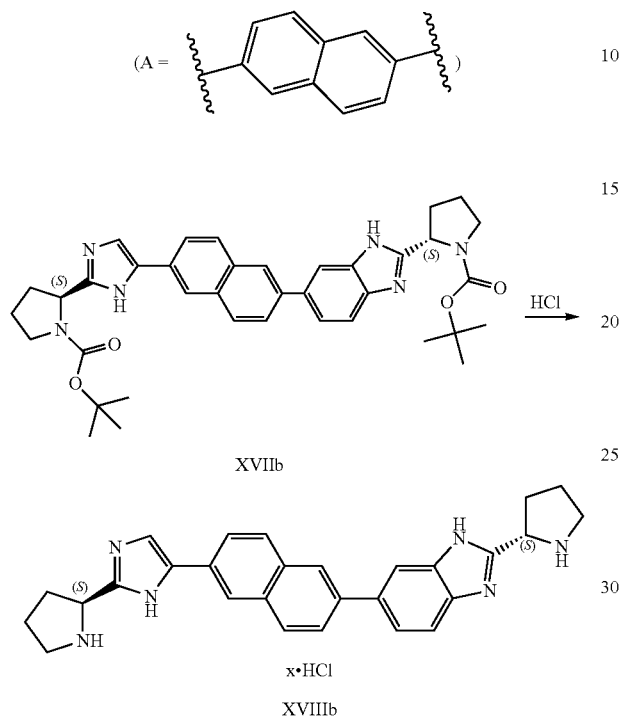

XVIIb (19.52 g, 30.1 mmol, 1.00 equiv.) was dissolved in dichloromethane (200 mL) and HCl in isopropanol (5-6 N, 300 mL) was added. The reaction mixture was stirred for 1 hour at room temperature. tBuOMe (1000 mL) was added to the suspension and the slurry was stirred at roomtemperature for 30 minutes. The filtered solid was rinced with tBuOMe (2×100 mL) and dried under vacuum overnight to afford XVIIIb as a powder (15.2 g).

$^1$H NMR (400 MHz, MeOD-d$_4$) δ ppm 2.15-2.37 (m, 2H), 2.37-2.52 (m, 2H), 2.52-2.69 (m, 2H), 2.69-2.88 (m, 2H), 3.56-3.71 (m, 4H), 5.19-5.41 (m, 2H), 7.90-8.02 (m, 3H), 8.05 (dd, J=8.6, 1.6 Hz, 1H), 8.10-8.25 (m, 4H), 8.30 (d, J=1.4 Hz, 1H), 8.47 (d, J=1.2 Hz, 1H)

Example 2a

Synthesis of Compounds of Formula XXVI and XXVII

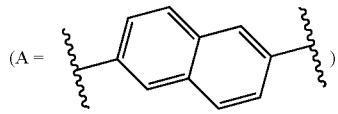 [SMILES: *c1ccc2cc(*)ccc2c1]

2a.1 Preparation of Intermediate XXVb

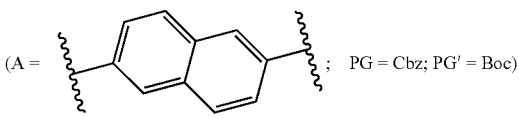 [SMILES: *c1ccc2cc(*)ccc2c1]

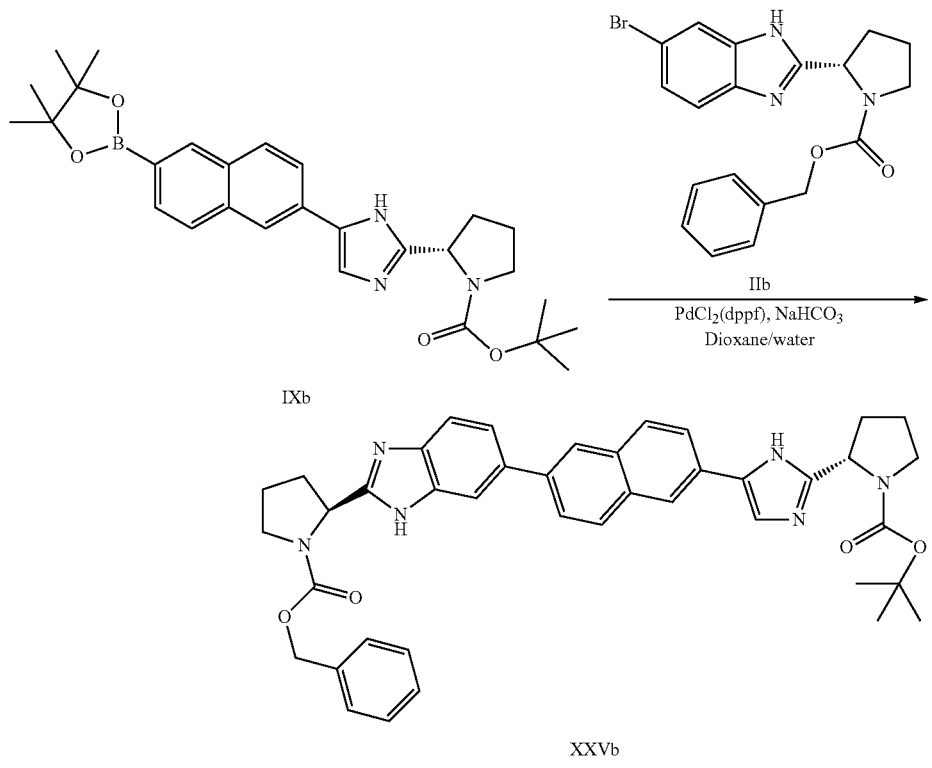

To IXb (2.63 g, 5.37 mmol), IIb (2.80 g, 6.99 mmol), PdCl$_2$(dppf) (298 mg, 0.537 mmol) and sodiumbicarbonate (1.354 g, 16.12 mmol), dioxane/water (50 mL, 5/1) was added. The reaction was heated for 13 hours at 80° C. under argon atmosphere. The reaction mixture was cooled to room temperature, diluted with dichloromethane and brine was added, the mixture was filtrated over decalite and the organic phase separated. The organic phase was dried with MgSO$_4$, the solvent was removed under reduced pressure and purified by column chromatography (gradient from 0 to 3% methanol in CH$_2$Cl$_2$) to yield XXVb (2.086 g, 57%)

A stirring solution of VIIIc (36.1 g, 75.8 mmol), Ma (28.5 g, 68.89 mmol) and sodiumbicarbonate (17.36 g, 206.7 mmol) in dioxane/water (500 mL, 5/1) was flushed with nitrogen for 10 minutes before addition of PdCl$_2$(dppf) (5.04 g, 6.889 mmol). The mixture was heated for 15 hour under Argon at 80° C. The reaction was cooled to room temperature, diluted with dichloromethane (500 mL) and washed with brine (2×300 mL). The organic phase was dried over MgSO$_4$, filtered and evaporated to yield a black foam. The mixture was stirred in EtOAc (300 mL), the black precipitates were filtered off and the cake was washed with more EtOAc (200 mL). Heptane (1.5 L) was added slowly to the EtOAc-filtrate and the precipitate was filtered. to yield XXVc (28.35 g, 60%)

2a.2 Preparation of Intermediate XXVc 2a.3 Preparation of XXVIIb

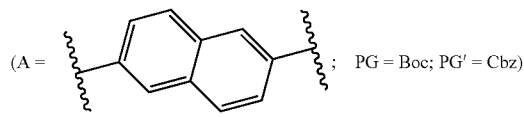 [SMILES: *c1ccc2cc(*)ccc2c1]

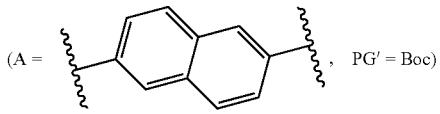 [SMILES: *c1ccc2cc(*)ccc2c1]

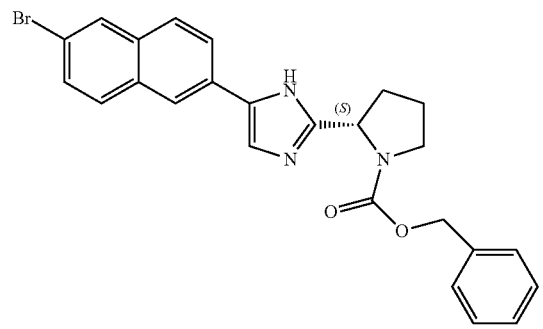

VIIIc

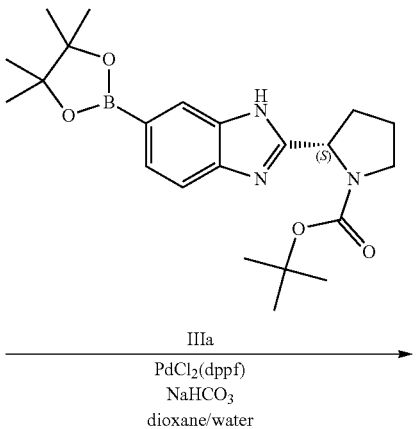

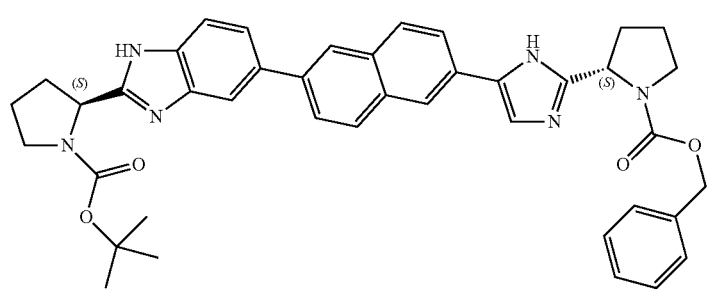

XXVc

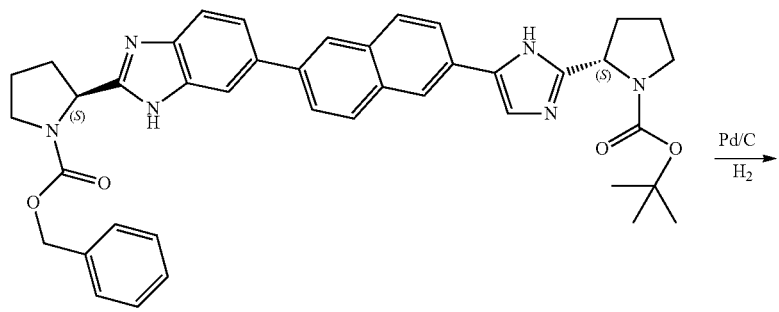

XXVb

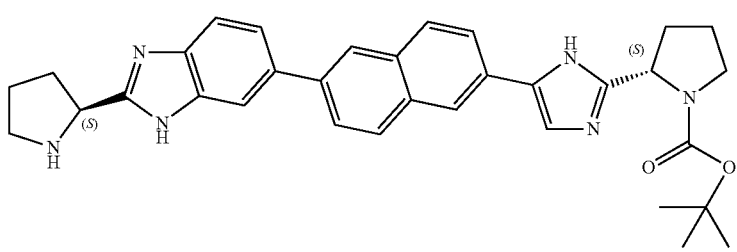

XXVIIb

Potassium carbonate (334 mg, 2.42 mmol) was added to a solution of XXVb (2.086 g, 3.054 mmol), Pd/C (10%, 0.5 g) and some drops of water in methanol (40 mL). The reaction was placed under an hydrogen atmosphere for 2.5 hours. The mixture was filtrated over decalite, the solvent was removed under reduced pressure and the product was purified by silica gel column chromatography (gradient of methanol in CH$_2$Cl$_2$ from 0-3%, then CH$_2$Cl$_2$ methanol/NH$_3$ (7N) from 3-10%) to yield XXVIIb (1.018 g, 61%).

2a.4 Preparation of XXVIb

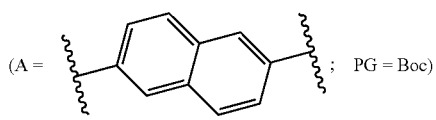 [SMILES: *c1ccc2cc(*)ccc2c1]

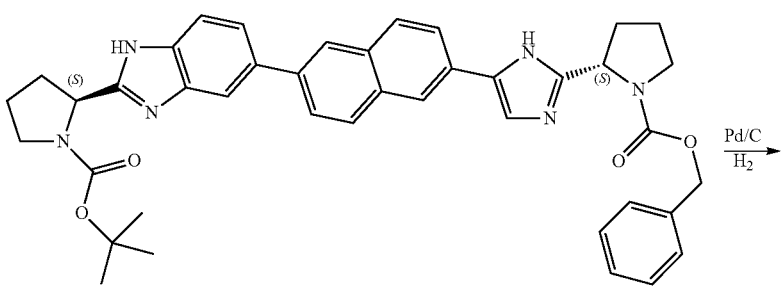

XXVc

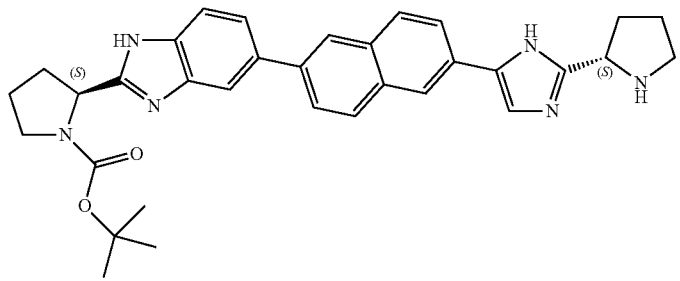

XXVIb

Potassium carbonate (4.8 g, 34.7 mmol, 0.9 equiv.) was added to a mixture of 10% Pd/C (2 g), XXVc (26.35 g, 38.6 mmol, 1.00 equiv.), methanol (800 mL) and water (5 mL) in a round bottomed flask (2 L). The reaction mixture was stirred under a hydrogen atmosphere overnight. Then, additional catalyst (10% Pd/C, 2 g) was added and the reaction mixture was further stirred under a hydrogen atmosphere for 2 hours. Then, additional potassium carbonate (4.8 g, 34.7 mmol, 0.9 equiv.) and catalyst (10% Pd/C)(2 g) were added and the mixture was further stirred under hydrogen overnight. The reaction mixture was filtered over dicalite speed plus (diatomaceous filter aid) and washed with methanol (2×50 mL). The solvent was evaporated to afford a brownish powder which was dissolved in dichloromethane (400 mL) and washed with water (2×200 mL) dried on magnesium sulphate, filtrated and evaporated to dryness. The resulting crude material (23 g) was submitted to silica gel column chromatography (gradient elution with 0-5% methanol in dichloromethane followed by 5-10% methanol (7N NH$_3$) in dichloromethane) to provide XXVIb as a light brown powder (13.85 g, 65%).

Example 2b

Synthesis of N-Methoxycarbonyl amino acids 2b.1 Synthesis of (S)-2-(methoxycarbonylamino)-3-methylbutanoic acid

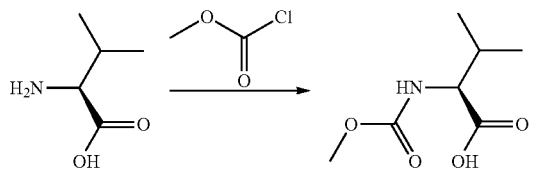

To L-Valine (20 g, 167.3 mmol) in a stirred aqueous NaOH (1M, 167 mL) solution in a round bottom flask (1 L), sodium carbonate (8.866 g, 83.6 mmol) was added. The flask was cooled to 0° C. in an ice-water bath. Methyl chloroformate (17.4 g, 184 mmol) was added drop wise and the reaction mixture was allowed to stir for 15 hours and reach room temperature. The reaction mixture was separated with ether (3×200 mL), and the aqueous layer was contained in a round bottom flask and cooled in a ice-water bath. Concentrated HCl (aq) was added drop wise until pH 2. The mixture was brought to room temperature and extracted with dichloromethane (3×200 mL). The organic layers were pooled, dried (sodium sulfate), and the solids were removed by filtration. The solvents of the filtrate were removed under reduced pressure to afford a white solid. The white solid was further dried in vacuum (25.3 g, 86%).

2b.2 Synthesis of ((S)-2-cyclopropyl-2-(methoxycarbonylamino)acetic acid

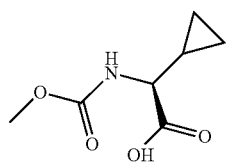

(S)-2-cyclopropyl-2-(methoxycarbonylamino)acetic acid was synthesized similar to N-methoxycarbonyl-L-Valine, using L-cyclopropylglycine instead of L-Valine.

2b.3 Synthesis of ((2S,3S)-2-(methoxycarbonylamino)-3-methylpentanoic acid

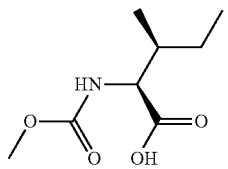

(2S,3S)-2-(methoxycarbonylamino)-3-methylpentanoic acid was synthesized similar to N-methoxycarbonyl-L-Valine, using L-isoleucine instead of L-Valine.

2b.4 2-(methoxycarbonylamino)-2-(tetrahydro-2H-pyran-4-yl)acetic acid

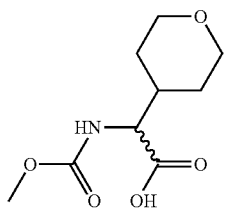

2-(methoxycarbonylamino)-2-(tetrahydro-2H-pyran-4-yl)acetic acid was synthesized similar to N-methoxycarbonyl-L-Valine, using (S)-2-amino-2-(tetrahydro-2H-pyran-4-yl)acetic acid instead of L-Valine.

2b.5 Synthesis of (2S,3R)-3-methoxy-2-(methoxycarbonylamino)butanoic acid

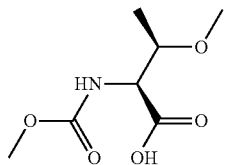

(2S,3R)-3-methoxy-2-(methoxycarbonylamino)butanoic acid was synthesized similar to N-methoxycarbonyl-L-Valine, using O-Methyl-L-Threonine instead of L-Valine. Dichloromethane extraction was carried out 10 times instead of 3 times.

2b.6 Synthesis of (S)-2-(methoxycarbonylamino)-4-methylpentanoic acid

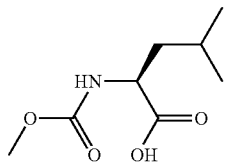

An aqueous NaOH (1M, 2.6 mL) solution is added, while stirring, to L-Leucine (4 g, 30.5 mmol) in a round bottom flask (250 mL). To this solution was added sodium carbonate (1.62 g, 15.2 mmol). The flask is cooled to 0° C. in an ice-water bath. Methyl chloroformate (2.6 mL, 33.5 mmol) is added drop wise and the reaction mixture is allowed to stir for 15 hours and reach room temperature. The reaction mixture is separated with ether (3×50 mL), and the aqueous layer is contained in a round bottom flask and cooled over an ice-water bath. Concentrated HCl (aq) is added drop wise until pH 2. The reaction mixture is brought to room temperature and extracted with 2-Me-THF (3×50 mL). The organic layers are pooled, dried ($MgSO_4$), the solids removed by filtration, and the solvents of the filtrate removed under reduced pressure. The compound was purified by silicagel chromatography with gradient elution from $CH_2Cl_2$ to $CH_2Cl_2$/MeOH/acetic acid 17/2/1. Fractions containing product were combined and the solvent were removed in vacuum, resulting in N-methoxycarbonyl-L-leucine (1.9 g, 32%).

2b.7 Synthesis of (S)-4-methoxy-2-(methoxycarbonylamino)butanoic acid

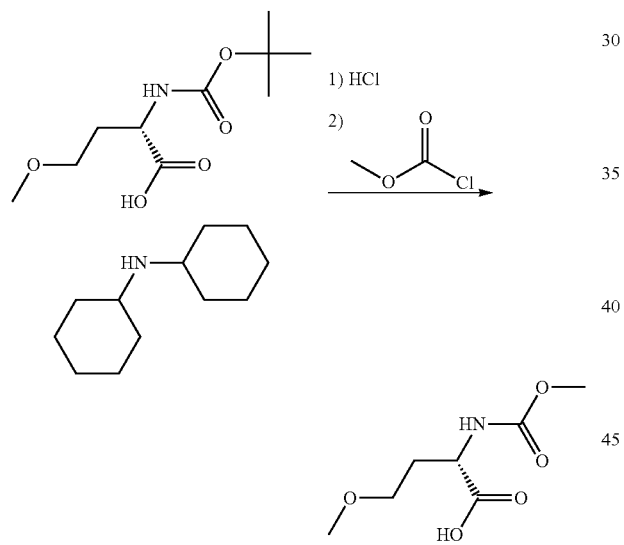

To Boc-O-methyl-L-homoserine-dicyclohexylamine salt (5 g, 12.1 mmol), was added HCl in isopropanol (5-6 N, 50 mL). The mixture was stirred overnight. The volatiles were removed and the residue was dried in vacuum. To the obtained residue, water (10 mL) and NaOH (19 M, 2 mL) were added, while stirring. To this solution was added sodium carbonate (2.89 g, 27.3 mmol). The flask was cooled to 0° C. in an ice-water bath. Methyl chloroformate (2.17 mL, 27.3 mmol) was added drop wise and the reaction mixture was allowed to stir for 15 hours and reach room temperature. The solvent was removed and the residue was purified by HPLC (RP Vydac Denali C18 –10 µm, 250 g, 5 cm). Mobile phase (0.25% $NH_4HCO_3$ solution in water, MeOH+$CH_3CN$), the desired fractions were collected, and the solvent removed, yielding. N-Methoxycarbonyl-O-methyl-L-homoserine (1.77 g, 76%)

2b.8 Synthesis of (2S,3R)-3-hydroxy-2-(methoxycarbonylamino)butanoic acid

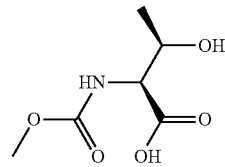

An aqueous NaOH (1 M, 167 mL) solution is added, while stirring, to L-Threonine (20 g, 30.5 mmol) in a round bottom flask (1 L). To this solution was added sodium carbonate (9.8 g, 92.3 mmol). The flask is cooled to 0° C. in an ice-water bath. Methyl chloroformate (14.3 mL, 184.7 mmol) is added drop wise and the reaction mixture is allowed to stir for 15 hours and reach room temperature. The reaction mixture is washed with $CH_2Cl_2$ (3×50 mL), and the aqueous layer is contained in a round bottom flask and cooled over an ice-water bath. Concentrated HCl (aq) is added drop wise until pH 2. The aqueous solution is brought to room temperature and the water is removed in vacuum. The residue was taken up in a 2:1 mixture of MeOH/$CH_2Cl_2$ (150 mL, filtered and washed with 2:1 mixture of MeOH/$CH_2Cl_2$ (50 mL). The filtrate was concentrated and dried in vacuum at 40° C., resulting in white foam (29.1 g, 98%).

2b.9 Synthesis of (S)-2-cyclopentyl-2-(methoxycarbonylamino)acetic acid

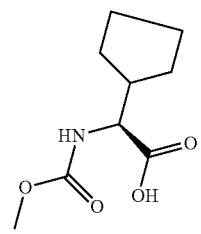

(S)-2-cyclopentyl-2-(methoxycarbonylamino)acetic acid was synthesized similar to N-methoxycarbonyl-L-Valine, using (S)-2-amino-2-cyclopentylacetic acid instead of L-Valine.

2b.10 Synthesis of (2S,3R)-2-(methoxycarbonylamino)-3-methylpentanoic acid

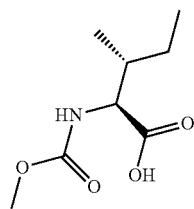

(2S,3R)-2-(methoxycarbonylamino)-3-methylpentanoic acid was synthesized similar to N-methoxycarbonyl-L-Valine, using (2S,3R)-2-amino-3-methylpentanoic acid instead of L-Valine.

2b.11 Synthesis of (R)-2-(methoxycarbonylamino)-2-phenylacetic acid

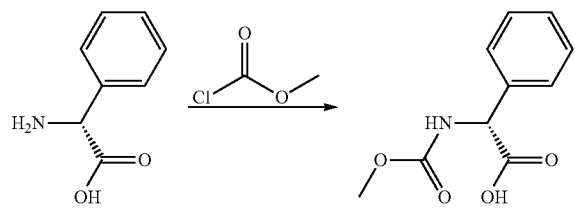

To a solution of (R)-2-amino-2-phenylacetic acid (14 g, 92.6 mmol) in water (250 mL) was added LiOH (14.8 g, 618.7 mmol) at 0° C. and the mixture was stirred for 15 minutes. To this solution, methyl chloroformate (17.9 mL, 231.5 mmol) was added drop wise and the mixture was stirred for 2 hours at 0° C. The mixture was then acidified until pH 1 with concentrated HCl. The mixture was extracted with EtOAc and the organic phase was concentrated in vacuum. The residue was dried overnight in vacuum, resulting in (R)-2-(methoxycarbonylamino)-2-phenylacetic acid (11.8 g; 60.9 mmol).

Example 3

Synthesis of Compounds of Formula I 3.1. Preparation of Compound nr. 1

Dry pyridine (5 mL) was added to compound XVIIIa (267 mg, ~0.49 mmol), and the solvent was removed in vacuum, this was repeated twice more. Then, dry DMF (5 mL) DIPEA (0.845 mL, 4.91 mmol), HATU (466 mg, 1.23 mmol) and N-methoxycarbonyl-L-Valine (215 mg, 1.23 mmol) were added. The mixture was stirred for 2 hours at room temperature. The same equivalents of reagents were added again and the mixture was further stirred for 2 hours. $CH_2Cl_2$ (20 mL) was added and the mixture was washed with 10% citric acid (20 ml) followed by saturated $NaHCO_3$. The organic phase was dried on $MgSO_4$ and the solid were removed by filtration. The solvent was evaporated and purification was performed by silica gel chromatography (0-10% methanol in $CH_2Cl_2$), resulting in compound 1 as a solid (170 mg, 0.226 mmol). Method A: Rt: 4.18 min. m/z=: 713.4 (M+1)+Exact mass: 712.37; $^1$H NMR (400 MHz, DMSO-$d_6$): 12.99-11.63 (2H,s (br)), 7.88-7.44 (8H, m), 7.36-7.26 (2H, m), 5.26-5.16 (1H, m), 5.06-5.14 (1H, m), 4.14-4.04 (2H, m), 3.90-3.77 (4H, m), 3.55 (6H, s), 2.32-1.94 (10H, m), 1.00-0.79 (12H, m).

3.2 Preparation of Compounds 2 to 4

Compound 2 was synthesized following the procedure reported for compound 1 using —N-Methoxycarbonyl-O-Methyl-L-Threonine instead of N-Methoxycarbonyl-L-Valine. Compound 2. $^1$H NMR (400 MHz, DMSO-$d_6$): 12.12-12.26 (1H, m), 11.69-11.83 (1H, s (br)), 7.33-7.86 (8H, m), 7.18-7.31 (2H, m), 5.15-5.25 (1H, m), 5.05-5.13 (1H, m), 4.25-4.38 (2H, m), 3.77-3.95 (4H, m), 3.55 (6H, s), 3.45-3.52 (2H, m), 3.20 (6H, s), 1.79-2.38 (8H, m), 1.14-1.06 (6H, m).

Compound 3 was prepared following the procedure reported for the synthesis of compound 1 using intermediate XVIIIb instead of intermediate XVIIIa.

Compound 3. $^1$H NMR (400 MHz, DMSO-$d_6$) δ ppm 8.34 (2H, s), 8.21 (1H, s), 8.19 (1H, d, J=8.69 Hz), 8.06-8.11 (2H,

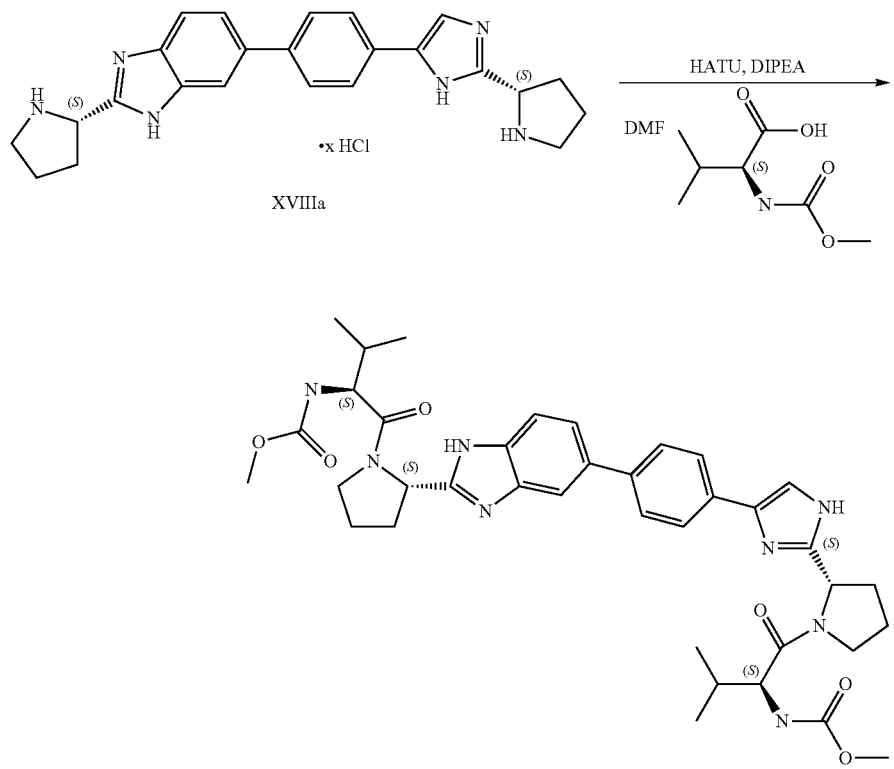

m), 8.00 (1H, dd, J=8.88, 1.61 Hz), 7.88-7.96 (2H, m), 7.86 (1H, d, J=8.48 Hz), 7.32 (1H, d, J=8.48 Hz), 7.34 (1H, d, J=8.53 Hz), 5.27 (1H, dd, J=8.17, 5.33 Hz), 5.17 (1H, t, J=7.00 Hz), 4.15 (2H, t, J=7.95 Hz), 3.84-3.96 (4H, m), 3.56 (6H, s), 2.38-2.47 (2H, m), 1.95-2.30 (8H, m), 0.86 (3H, d, J=6.70 Hz), 0.85 (3H, d, J=6.70 Hz), 0.81 (6H, d, J=6.63 Hz).

$[\alpha]_D^2$=−148.98° (c 0.3336 w/v %, MeOH)

Alternative Preparation of Compound 3 and the Corresponding HCl Salt

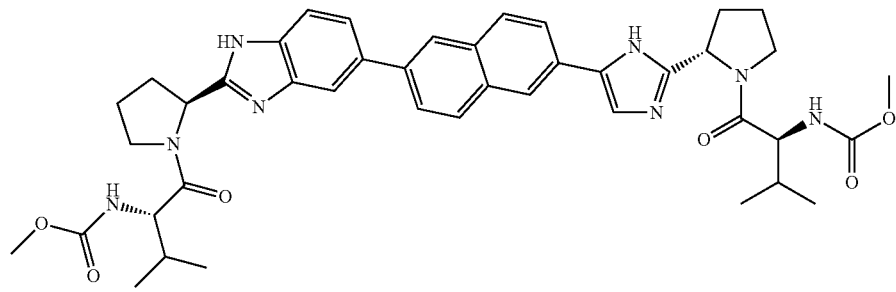

N-methoxycarbonyl-L-Valine (3.09 g, 17.7 mmol, 2.1 equiv) was dissolved in dichloromethane (300 mL). Triethylamine (11.7 mL, 84.1 mmol, 10 equiv) and (1-cyano-2-ethoxy-2-oxoethylidenaminooxy)dimethylamino-morpholino-carbenium hexafluorophosphate were added (7.57 g, 17.7 mmol, 2.1 eq). The reaction mixture was stirred at room temperature for 5 minutes, after which XVIIIb was added (5 g, 8.41 mmol in case x.HCl equals 4 HCl). Stirring was continued for 30 minutes. HCl in iPrOH (6N) was added to the mixture (until pH=2), and the resulting mixture was stirred for 5 minutes. The solution was then washed with saturated aqueous sodium carbonate (2×200 mL) and once with brine (200 mL). The organic layer was separated, dried on magnesium sulphate and filtrated. After removal of the solvent in vacuum, the obtained residue was further dried in vacuum to afford an orange powder (6.84 g)

The powder was purified by silica gel column chromatography using gradient elution with 0 to 10% MeOH (7N NH$_3$) in dichloromethane, resulting in compound 3 (2.81 g) as a foam.

Compound 3 was dissolved in iPrOH (40 mL) and HCl (6N in iPrOH, 10 mL) was added. The volatiles were removed in vacuum. Then, iPrOH (30 mL) was added and the mixture was heated at reflux. The solution was cooled to room temperature and stirred at room temperature for 4 days. tBuOMe (100 mL) was added to the solution, resulting in white precipitation, which was filtered, washed immediately with tBuOMe (3×10 mL) under nitrogen atmosphere and dried under vacuum at 40° C. The residue was mixed with acetonitrile and evaporated to dryness (2×). The residue was stirred in acetonitrile (150 mL) and the mixture was sonicated for 10 minutes. The precipitate was filtered under nitrogen atmosphere, washed twice with acetonitrile (50 mL) and dried in vacuum at 40° C., resulting in a slightly yellow powder (4 g).

HCl salt of compound 3:

$[\alpha]_D^2$=−110.02° (589 nm, 20° C., c 0.429 w/v %, MeOH)

$^1$H NMR (600 MHz, DIMETHYLFORMAMIDE-d$_7$, 280K) δ ppm 0.86 (d, J=6.6 Hz, 6H), 0.95 (d, J=7.0 Hz, 6H), 2.03-2.20 (m, 2H), 2.26-2.37 (m, 3H), 2.39-2.61 (m, 5H), 3.61-3.63 (m, 6H), 3.93-4.01 (m, 2H), 4.23-4.32 (m, 2H), 4.32-4.39 (m, 2H), 5.49 (t, J=7.5 Hz, 1H), 5.52 (dd, J=8.3, 5.3 Hz, 1H), 7.22 (d, J=8.8 Hz, 1H), 7.27 (d, J=8.8 Hz, 1H), 7.98 (d, J=8.6 Hz, 1H), 8.01 (dd, J=8.6, 1.1 Hz, 1H), 8.03 (dd, J=8.8, 1.8 Hz, 1H), 8.09 (d, J=8.8 Hz, 1H), 8.19 (d, J=8.8 Hz, 1H), 8.22 (dd, J=8.4, 1.8 Hz, 1H), 8.25 (s, 1H), 8.32 (s, 1H), 8.41 (s, 1H), 8.88 (s, 1H).

Anal. Calcd for C$_{42}$H$_{50}$N$_8$O$_6$. 2 HCl.4H$_2$O: C, 55.56; H, 6.66; N, 12.34. Found: C, 55.00; H, 6.60; N, 12.30.

Compound 4 was prepared following the procedure reported for the synthesis of compound 2 using intermediate XVIIIb instead of intermediate XVIIIa.

$^1$H NMR (400 MHz, DMSO-d$_6$) δ ppm 8.07-8.30 (m, 2H), 7.88-7.98 (m, 3H), 7.73-7.87 (m, 2H), 7.50-7.67 (m, 3H), 7.21-7.33 (m, 2H), 5.18-5.24 (m, 1H), 5.06-5.16 (m, 1H), 4.31 (m, 2H), 3.80-3.95 (m, 4H), 3.56 (s, 6H), 3.43-3.53 (m, 2H), 3.20 (s, 6H), 1.80-2.35 (m, 8H), 1.05-1.20 (m, 6H), 3.3 Preparation of Compounds 9, 11, 13, 16, 17, 18

3.3.1 Preparation of Compound 9

3.3.1.1 Preparation of Intermediate XIII'b

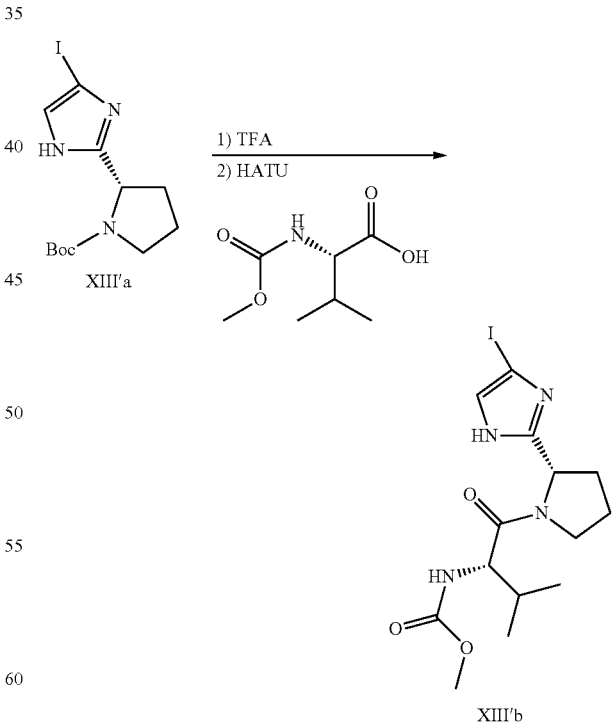

To XIII'a (5.3 g, 14.6 mmol) in CH$_2$Cl$_2$ (10 mL) at 0° C. was added TFA (25 mL). The mixture was warmed to room temperature and stirred for 30 minutes. The volatiles were removed and CH$_2$Cl$_2$ (10 mL) and DIPEA (15 mL) were added to the obtained TFA salt of (S)-4-iodo-2-(pyrrolidin-2-yl)-1H-imidazole. Half of this mixture was used below. In another flask, to (S)-2-(methoxycarbonylamino)-3-methylbutanoic acid (1.77 g, 10.12 mmol) and HATU (3.57 g, 9.40 mmol) was added dry DMF (5 mL). DIPEA (5 mL, 28.7 mmol) was added followed by half of the above prepared mixture of (S)-4-iodo-2-(pyrrolidin-2-yl)-1H-imidazole.

The mixture was stirred overnight. CH$_2$Cl$_2$ was added and the mixture was washed with brine, 10% AcOH and sat. NaHCO$_3$. After drying with MgSO$_4$ and filtration, the solvent was removed. The mixture was purified via column chromatography using gradient elution from CH$_2$Cl$_2$ to CH$_2$Cl$_2$/MeOH 95/5. The fractions containing product were combined and the solvent was removed. The obtained residue was dissolved in CH$_2$Cl$_2$ and washed with 10% citric acid. The water layer was carefully neutralized with saturated NaHCO$_3$ and again extracted with CH$_2$Cl$_2$. The organic layers were dried with Na$_2$SO$_4$ and after filtration, the solvent was removed. The obtained XIII'b (790 mg, 26%) was used as such in the next reaction.

3.3.1.2 Preparation of Intermediate XXIb

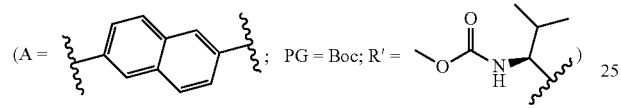

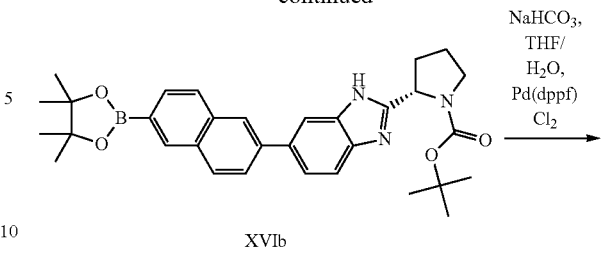

XVIb

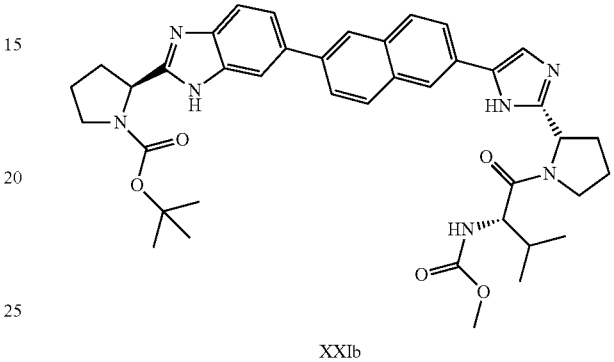

XXIb

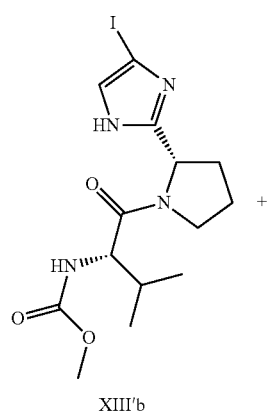

XIII'b

XVIb (867 mg, 1.61 mmol), XIII'b (790 mg, 1.88 mmol), sodium bicarbonate (316 mg, 3.76 mmol) and Pd(dppf)Cl$_2$ (138 mg, 0.188 mmol) were dissolved in THF/H$_2$O (2.5 mL, 4/1) and heated in the microwave for 60 minutes at 100° C. The reaction mixture was filtered over dicalite, the volatiles were removed from the filtrate by rotary evaporation and the residue was purified by silica gel column chromatography (gradient elution from CH$_2$Cl$_2$ to CH$_2$Cl$_2$/MeOH 9/1) The fractions containing XXIb were pooled and the solvent was removed under reduced pressure, yielding XXIb as an off white powder (580 mg, 44%).

Alternatively, compound XXIb, can be obtained starting from compound XXVIb similar as described in the synthesis of compound XXIc from XXVIb, with the exception that for the synthesis of XXIb (S)-2-(methoxycarbonylamino)-3-methylbutanoic acid is used instead of (2S,3S)-2-(methoxycarbonylamino)-3-methylpentanoic acid, that is used in the synthesis of XXIc.

3.3.1.3 Preparation of Compound 9

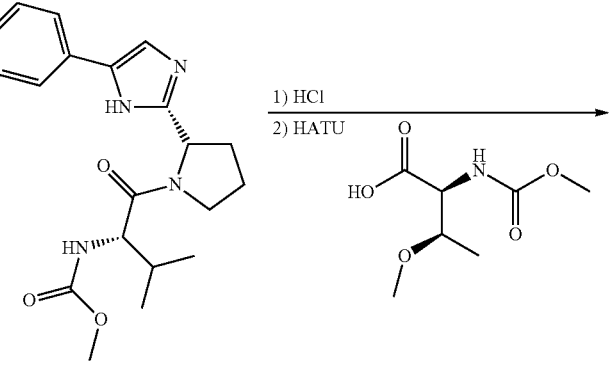

XXIb

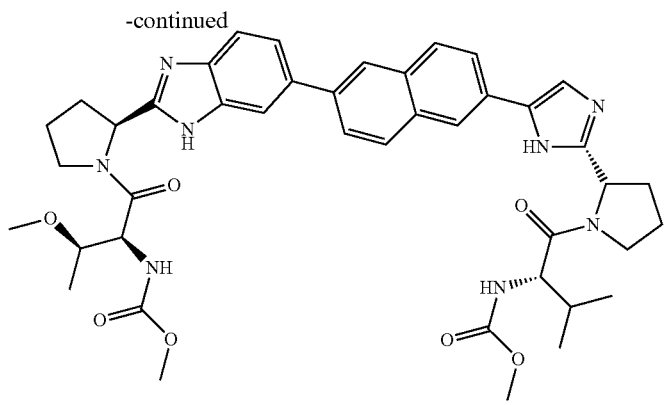

9

To XXIb (580 mg, 0.822 mmol) in CH$_2$Cl$_2$ (10 mL), HCl in iPrOH was added (5-6 N, 3 mL). The mixture was stirred at room temperature for 2 hours. The volatiles were removed and Hunigs' base (0.53 mL, 4 eq) in DMF (5 mL) was added. This mixture was added to a premixed (10 minutes) solution of HATU (469 mg, 1.23 mmol, 1.5 eq), (2S,3R)-3-methoxy-2-(methoxycarbonylamino)butanoic acid (318 mg, 1.64 mmol, 2 eq) and Hunigs' base (0.15 mL, 1.1 eq) in DMF (5 mL). The reaction mixture was stirred for 30 minutes. 15 drops of conc. HCl were added and after 15 minutes the volatiles were removed by rotary evaporation. The residue was purified by silica gel column chromatography by gradient elution from CH$_2$Cl$_2$ to 9/1 CH$_2$Cl$_2$/MeOH (7 N NH$_3$). The fractions containing the product were pooled and the solvent was removed under reduced pressure yielding product 9 as a white powder (121 mg, 18%). $[\alpha]_D^{20}$=−137.04° (c 0.3736 w/v %, MeOH).

$^1$H NMR (600 MHz, CD$_3$OD-d$_4$) δ ppm 8.04-8.25 (2H, m) 7.37-7.97 (8H, m), 5.33 (1H, dd, J=4.7; 7.9 Hz), 5.21 (1H, dd, J=5.6; 7.9 Hz) 4.48 (1H, d, J=4.7; Hz) 4.25 (1H, d, J=7.6 Hz), 3.86-4.04 (4H, m) 3.68-3.73 (1H, m) 3.63-3.68 (6H, m) 3.27 (3H, s) 1.99-2.49 (9H, m) 1.14-1.19 (3H, m) 0.95-0.99 (3H, m) 0.90-0.93 (3H, m)

3.3.1.4 Preparation of Compound 13

Compound 13 can be synthesized similar as described in the conversion of XXIb to compound 9, using (2S,3S)-2-(methoxycarbonylamino)-3-methylpentanoic acid instead of (2S,3R)-3-methoxy-2-(methoxycarbonylamino)butanoic acid. $[\alpha]_D^{20}$=−147.6° (c 0.3618 w/v %, MeOH).

$^1$H NMR (400 MHz, DMSO-d$_6$) δ ppm 11.71-12.51 (2H, m) 7.51-8.31 (10H, m) 7.22-7.39 (2H, m) 5.06-5.45 (2H, m) 4.02-4.19 (2H, m) 3.75-3.95 (4H, m) 3.52-3.57 (6H, m) 1.81-2.30 (9H, m) 1.65-1.79 (1H, m) 1.39-1.53 (1H, m) 1.02-1.14 (1H, m) 0.74-0.98 (12H, m)

3.3.2 Preparation of Compound 11

3.3.2.1 Preparation of Intermediate XIXb

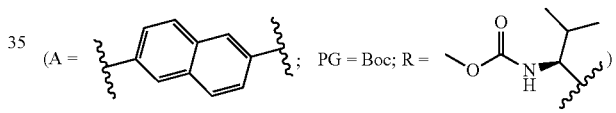

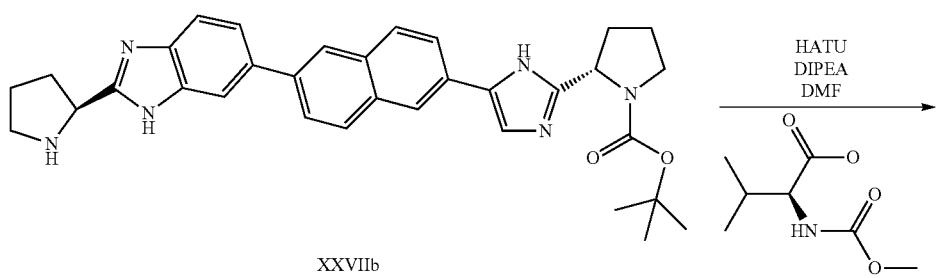

XXVIIb

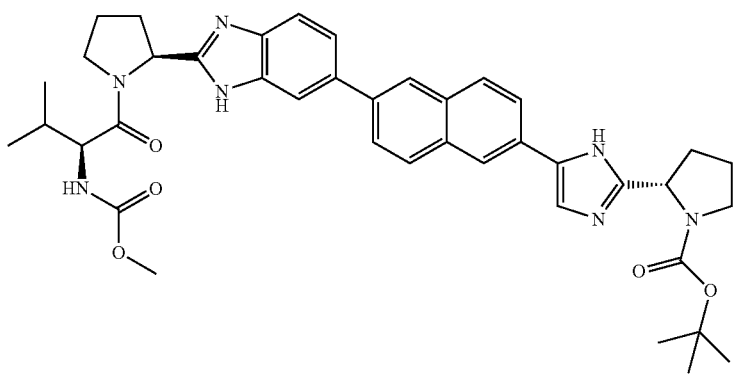

XIXb

HATU (776 mg, 2.04 mmol), DIPEA (0.48 mL, 2.78 mmol) and (S)-2-(methoxycarbonylamino)-3-methylbutanoic acid (357 mg, 2.04 mmol) are dissolved in dry DMF (10 mL) and stirred for 5 minutes at room temperature. XXVIIb (1.018 g, 1.855 mmol) was added and the reaction was stirred 1 hour at room temperature. Dichloromethane (100 mL) was added and the mixture was washed with saturated NaHCO$_3$-solution (3×100 mL). The organic phase was dried over MgSO$_4$, filtrated and the solvent evaporated. The residue was used as such in the next reaction.

3.3.2.2 Preparation of Intermediate XXb

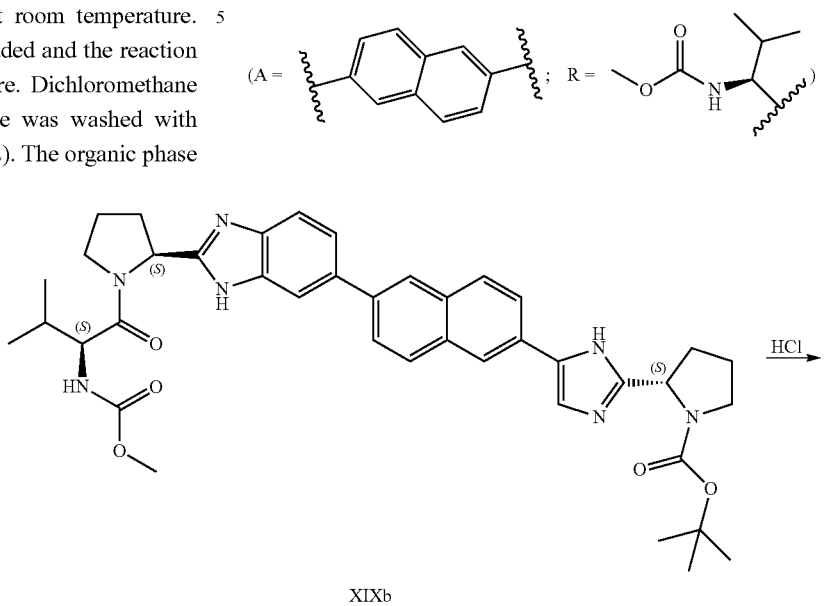

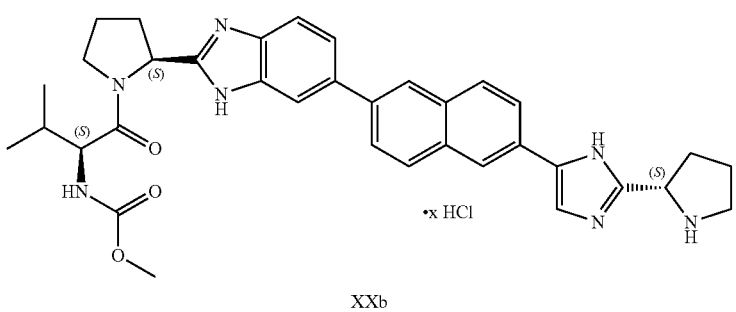

XIXb (1.309 g, 1.855 mmol) was dissolved in CH$_2$Cl$_2$ (10 mL) and HCl in iPrOH (5-6 N, 15 mL) was added. The mixture was stirred for 35 minutes at room temperature. tBuOMe (50 mL) was added and the slurry was stirred at room temperature for 30 minutes. The filtered solid was rinced with tBuOMe (50 mL) and dried in vacuum oven at 40° C. to yield XXb (1.137 g).

3.3.2.3 Preparation of Compound 11

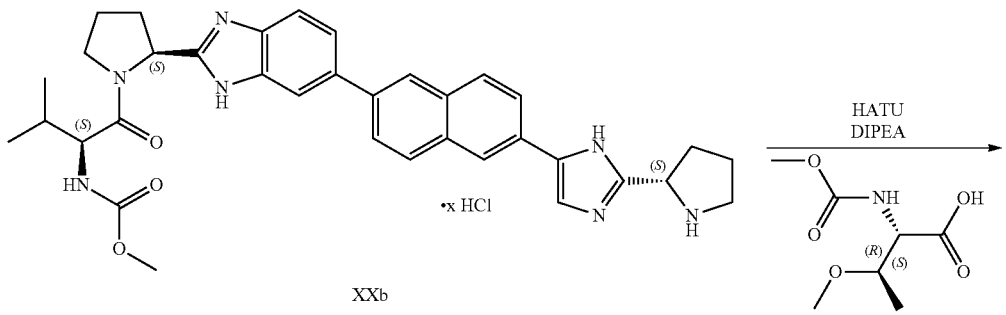

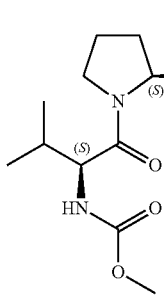

11

HATU (858 mg, 2.26 mmol), DIPEA (0.808 mL, 4.69 mmol) and (2S, 3R)-3-methoxy-2-methoxycarbonylamino)butanoic acid (432 mg, 2.26 mmol) are dissolved in dry DMF (10 mL) and stirred 5 minutes at room temperature. XXb (1.137 g, 1.59 mmol) was added and the reaction was stirred 2 hours at room temperature, after which more DIPEA (1.5 eq) was added and the mixture was stirred for 1 hour more. Dichloromethane (100 mL) was added and the mixture was washed with saturated NaHCO3-solution (3×100 mL), organic phase was dried over MgSO4, filtrated, the solvent evaporated and purified on column using a gradient from 0 to 5% methanol in dichloromethane to yield 11 (585 mg, 47%). $[\alpha]_D^{20}$=−134.69° (c 0.3638 w/v %, MeOH)

$^1$H NMR (400 MHz, DMSO-d$_6$, NH exchanged with D$_2$O) δ ppm: 0.78-0.91 (m, 6H) 1.05-1.19 (m, 3H), 1.86-2.30 (m, 9H), 3.21 (s, 3H), 3.46-3.62 (m, 7H), 3.78-3.96 (m, 4H), 4.02-4.16 (m, 1H), 4.26-4.40 (m, 1H) 5.05-5.16 (m, 1H) 5.18-5.26 (m, 1H), 7.53-8.33 (m., 10H)

3.3.3 Preparation of Compound 16 and 17

3.3.3.1 Preparation of Intermediate XXIc

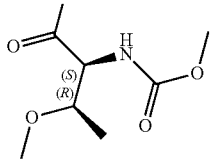

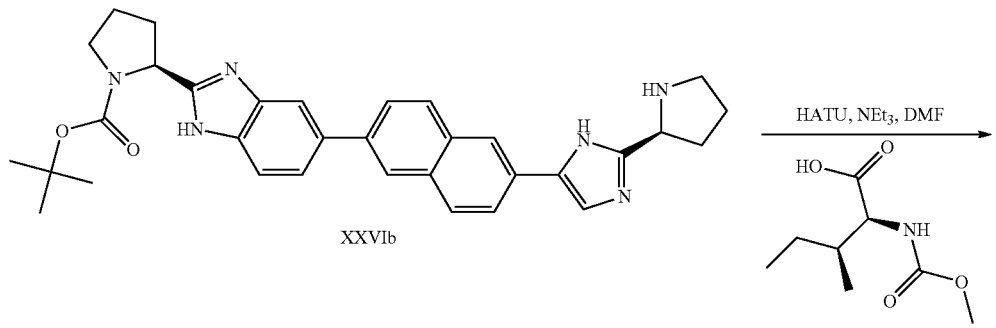

XXVIb

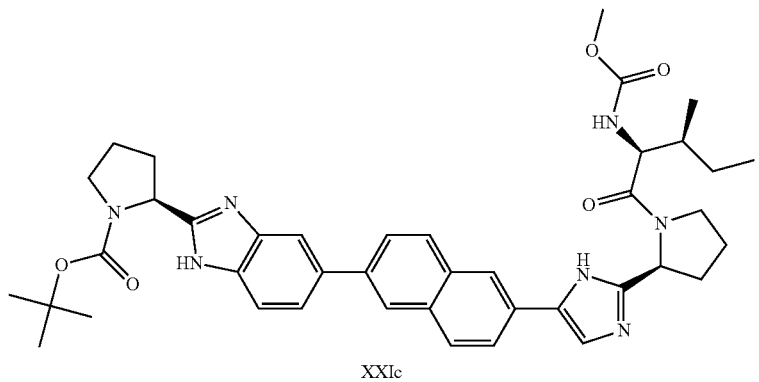

XXIc

To (2S,3S)-2-(methoxycarbonylamino)-3-methylpentanoic acid (2.39 g, 12.6 mmol, 1.05 equiv.) in a 100 mL round-bottomed flask, dimethylformamide (60 mL), triethylamine (3.34 mL, 24.1 mmol, 2.00 equiv.) and HATU (4.80 g, 12.6 mmol, 1.05 equiv.) were added. The reaction mixture was stirred for 5 minutes and XXVIb (6.60 g, 12.0 mmol, 1.00 equiv.) was added. The mixture was sonicated for one minute to dissolve everything. The reaction mixture was stirred for 20 minutes at room temperature. Saturated aqueous Na$_2$CO$_3$— solution (20 mL) was added to the mixture (pH paper check pH=11). The compound was extracted from the aqueous phase with dichloromethane (5×150 mL) and the combined organic layers were washed with saturated aqueous Na$_2$CO$_3$— solution (150 mL), dried on magnesium sulphate, filtered and the filtrate was evaporated to dryness to afford XXIc (9.3 g) which was used as such in next step.

3.3.3.2 Preparation of Intermediate XXIIc

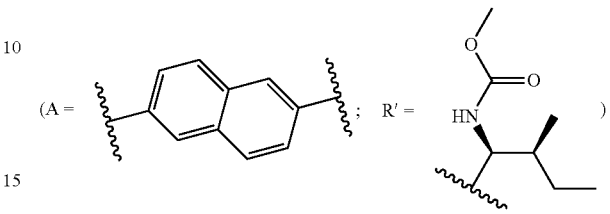

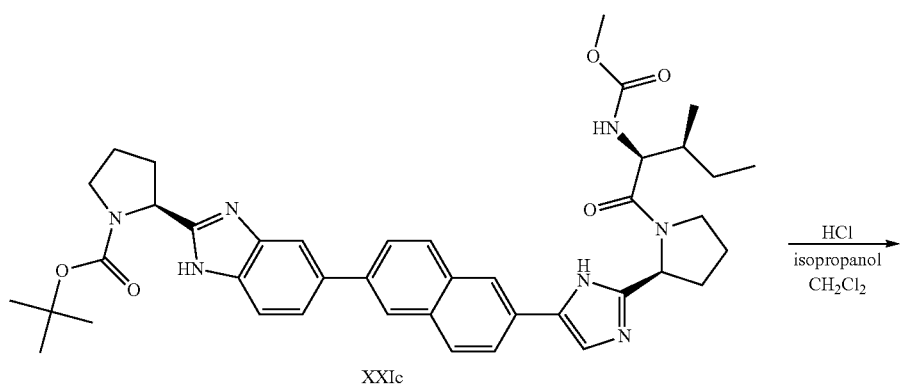

XXIc

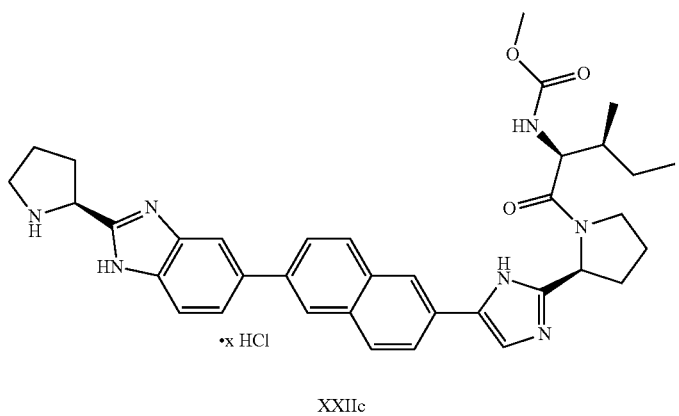

XXIIc

XXIc (8.66 g, 12.0 mmol, 1.0 equiv.) was dissolved in dichloromethane (40 mL) and 5-6 N HCl in isopropanol (40 mL, 200 mmol, 17 equiv.) was added. The reaction mixture was stirred overnight at room temperature. tBuOMe (400 mL) was added to the solution and the resulting slurry was stirred at room temperature for 30 minutes. The filtered solid was rinced with tBuOMe (2×100 mL) and dichloromethane (100 mL) and dried under vacuum overnight to afford XXIIc (8.35 g)

3.3.3.3 Preparation of Compound 16

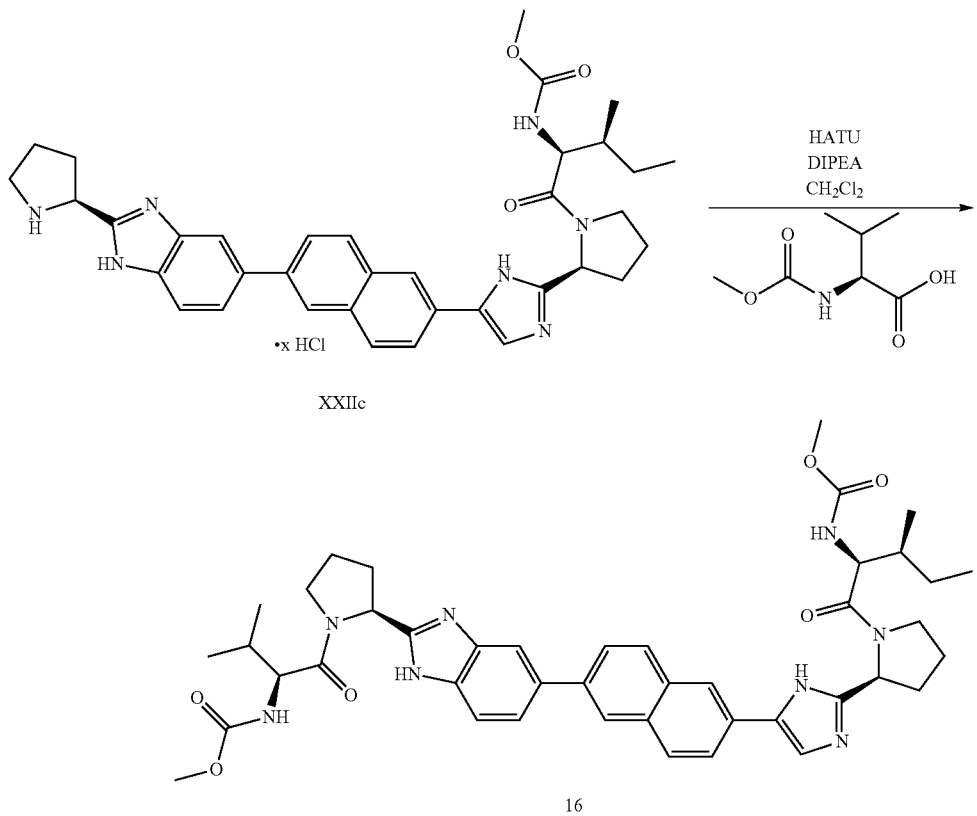

To (S)-2-(methoxycarbonylamino)-3-methylbutanoic acid (481 mg, 2.74 mmol) in a round-bottomed flask (500 mL), dichloromethane (300 mL), diisopropylethylamine (3.7 mL, 21 mmol) and HATU (1.04 g, 2.74 mmol) were added. The reaction mixture was stirred for 5 minutes and XXIIc (2.00 g, 2.74 mmol, if x HCl equals 3 HCl, 1.0 equiv.) was added. The reaction mixture was stirred for 2.5 hours at room temperature. The reaction mixture was washed with saturated aqueous Na$_2$CO$_3$-solution (2×100 mL), Brine (100 mL), dried on MgSO$_4$, filtered and the filtrate was evaporated to dryness to afford a brown residue. The residue was purified using silica gel column chromatography by gradient elution with 0-5% MeOH (7 N NH$_3$) in DCM, to afford a white powder (1.55 g). The powder was mixed with aqueous HCl (1 M) and methanol (15 mL) and again neutralized with saturated aqueous sodiumbicarbonate. The mixture was extracted with DCM (400 mL). The organic layer was separated and washed with water (4×150 mL); dried over magnesium sulphate and evaporated to dryness in vacuum. Drying over weekend in vacuum oven at 40° C. afforded compound 16 (1.49 g) as a white powder.

The HCl count on compound XXIIc was not determined. The procedure was performed with the amounts stated above. If x HCl equals 3 HCl in the above procedure, 1.0 equivalent of HATU and (S)-2-(methoxycarbonylamino)-3-methylbutanoic acid and ~8 equivalents diisopropylethylamine were used. In the theoretical case x HCl equals 4 HCl, 1.05 equivalent of HATU and S)-2-(methoxycarbonylamino)-3-methylbutanoic acid and ~8 equivalents diisopropylethylamine were used.

$^1$H NMR (400 MHz, MeOD) δ ppm 0.79-1.05 (m, 12H), 1.06-1.26 (m, 1H), 1.42-1.66 (m, 1H), 1.69-1.87 (m, 1H), 1.94-2.51 (m, 9H), 3.66 (2 s, 6H), 3.82-4.14 (m, 4H), 4.23-4.31 (m, 2H), 5.18-5.23 (m, 1H), 5.27-5.32 (m, 1H), 7.33-7.53 (m, 1H), 7.53-7.75 (m, 2H), 7.75-8.01 (m, 5H), 8.01-8.33 (m, 2H)

3.3.3.4 Preparation of Compound 17

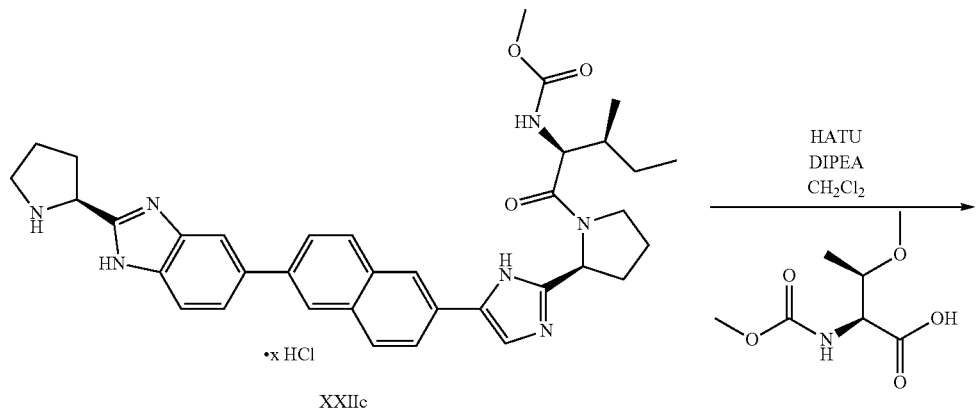

-continued

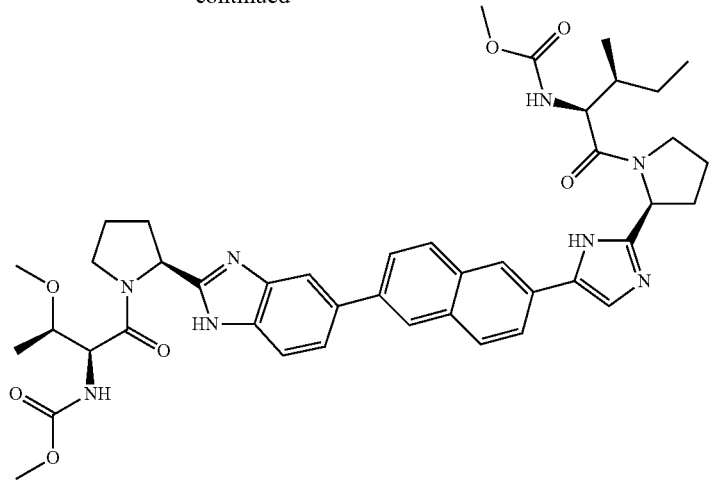

17

To (2S,3R)-3-methoxy-2-(methoxycarbonylamino)butanoic acid (524 mg, 2.74 mmol) in a round-bottomed flask (500 mL), dichloromethane (300 mL), diisopropylethylamine (3.7 mL, 21 mmol) and HATU (1.04 g, 2.74 mmol) were added. The reaction mixture was stirred for 5 minutes and XXIIc (2.00 g, 2.74 mmol, if x HCl equals 3 HCl, 1.0 equiv.) was added. The reaction mixture was stirred for 2.5 hours at room temperature. The reaction mixture was washed with saturated aqueous $Na_2CO_3$— solution (2×100 mL), Brine (100 mL), dried on $MgSO_4$ and filtered and the filtrate was evaporated to dryness to afford a brown residue. The residue was purified using silica gel column chromatography; by gradient elution with 0-5% MeOH (7N $NH_3$) in $CH_2Cl_2$ to afford compound 17 as a white powder (1.24 g). $[\alpha]_D^{20}=-158.7°$ (c 0.3472 w/v %, MeOH).

The HCl count on compound XXIIc was not determined. The procedure was performed with the amounts stated above. If x HCl equals 3 HCl in the above procedure, 1.0 equivalent of HATU and (2S,3R)-3-methoxy-2-(methoxycarbonylamino)butanoic acid and ~8 equivalents diisopropylethylamine were used. In the theoretical case x HCl equals 4 HCl, 1.05 equivalent of HATU and (2S,3R)-3-methoxy-2-(methoxycarbonylamino)butanoic acid and ~8 equivalents diisopropylethylamine were used.

$^1$H NMR (400 MHz, MeOD) δ ppm 0.83-1.00 (m, 6H), 1.10-1.22 (m, 4H), 1.49-1.65 (m, 1H), 1.72-1.85 (m, 1H), 1.92-2.52 (m, 8H), 3.27 (s, 3H), 3.62-3.77 (m, 7H), 3.84-4.08 (m, 4H), 4.28 (d, J=8.0 Hz, 1H), 4.48 (d, J=4.9 Hz, 1H), 5.16-5.25 (m, 1H), 5.33 (dd, J=8.2, 4.9 Hz, 1H), 7.24-8.35 (m, 10H)

Preparation of the .2 HCl.4H$_2$O Salt of the Compound 17

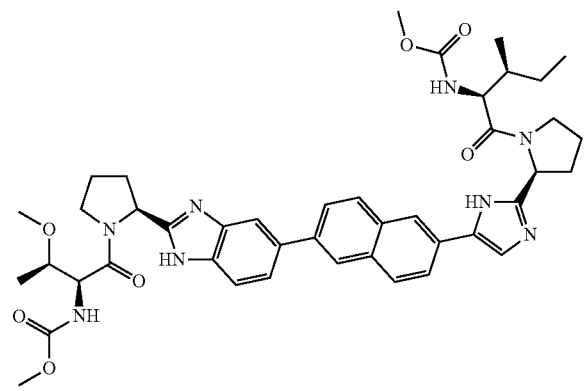

•2 HCl
•4 H$_2$O

Compound 17 (315 mg, 0.39 mmol) was dissolved in HCl/iPrOH (6N HCl) (10 mL) and the volatiles were removed. The salt was stirred at room temperature in acetonitrile (6 mL) overnight in an open flask. The mixture was evaporated to dryness. The residual water was azeotropically removed by repeated addition and evaporation, at 30° C. under reduced pressure, of acetonitrile (4×40 mL). The powder was then stirred in acetonitrile at room temperature in a closed round bottomed flask, overnight, filtered and immediately dried under vacuum overnight, to afford of a white powder (263 mg) The obtained solid was analyzed to have $C_{43}H_{52}N_8O_7$.2 HCl.4H$_2$O by elemental analysis, Anion Ion chromatography and H$_2$O titration.

Anal. Calcd for $C_{43}H_{52}N_8O_7$.2 HCl.4H$_2$O: C, 55.07; H, 6.66; N, 11.95. Found: C, 55.04; H, 6.57; N, 12.09. Calc.4H$_2$O: 7.68. Found: 7.96; Ion Chromatography (anion) Calc: 2 Cl$^-$ 7.56 Found: 7.75.

$^1$H NMR (600 MHz, DIMETHYLFORMAMIDE-d$_7$, 280K) δ ppm 0.85 (t, J=7.3 Hz, 3H), 0.91 (d, J=6.7 Hz, 3H), 1.07-1.13 (m, 1H), 1.15 (d, J=6.5 Hz, 3H), 1.40-1.47 (m, 1H), 1.98-2.05 (m, 1H), 2.08 (dt, J=12.4, 7.6 Hz, 1H), 2.12-2.19 (m, 1H), 2.29-2.37 (m, 1H), 2.40-2.45 (m, 1H), 2.48 (dd, J=12.9, 6.2 Hz, 1H), 2.50-2.55 (m, 2H), 2.56-2.62 (m, 1H), 3.27 (s, 3H), 3.61 (s, 3H), 3.62 (s, 3H), 3.93-4.04 (m, 3H), 4.29-4.33 (m, 2H), 4.35 (dd, J=8.7, 7.5 Hz, 1H), 4.50 (dd, J=8.8, 5.0 Hz, 1H), 5.46 (t, J=7.6 Hz, 1H), 5.53 (dd, J=8.2, 5.9 Hz, 1H), 7.00 (d, J=8.8 Hz, 1H), 7.26 (d, J=8.8 Hz, 1H), 8.00 (d, J=8.5 Hz, 1H), 8.02-8.06 (m, 2H), 8.09 (d, J=8.5 Hz, 1H), 8.20 (d, J=8.5 Hz, 1H), 8.22 (dd, J=8.8, 1.8 Hz, 1H), 8.26 (s, 1H), 8.33 (s, 1H), 8.42 (s, 1H), 8.89 (s, 1H)

$[\alpha]_D^{20}=-96.79°$ (c 9 (0.3492 w/v %, MeOH)

Preparation of the .H$_2$SO$_4$ Salt of the Compound 17

Compound 17 (15.0 g, 0.0189 mol) and ethanol (75 mL) were charged into a three-neck flask under N$_2$. The mixture was heated to 65-70° C. and stirred for 30 minutes. A solution of sulfuric acid (2.0 g, 0.0204 mol) in ethanol (75 mL) was added dropwise during 1 hour at 65-70° C. The mixture was stirred for 2 to 3 hours under N$_2$. The mixture was then cooled to 25-30° C. and stirred for another 1 to 2 hours. The resulting suspension was filtered and vacuum dried at 50-60° C. for at least 12 hours resulting in 16 g (94.8%) white solid which was analyzed to be the .H$_2$SO$_4$ salt of compound 17.

Aqueous solubility in mg/mL of this .H$_2$SO$_4$ salt at pH 1.2=32.23; at pH 2.2=13.34, at pH 4=0.26; at pH 7.4=0.001; at pH 12=0.02.

3.3.4 Preparation of Compound 18

To a solution of XXVIb (3.33 g, 6.07 mmol) in dry DMF (35 mL), was added DIPEA (1.57 mL, 9.104 mmol) and N-(methoxycarbonyl)-O-methyl-L-threonine (1.29 g, 6.68 mmol). This was stirred 5 minutes before HATU (2.53 g, 6.68 mmol) was added and the reaction was stirred 30 minutes at room temperature. The reaction was diluted with dichloromethane (100 mL) and washed saturated NaHCO$_3$-solution (3×100 mL). The organic phase was dried over MgSO$_4$, filtered, evaporated and the obtained compound XXId was used as such in next step.

3.3.4.2 Preparation of Intermediate XXIId

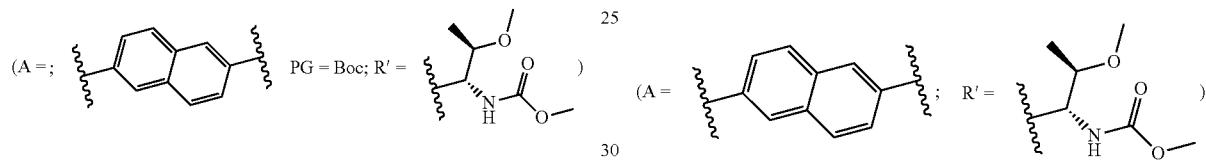

3.3.4.1 Preparation of Intermediate XXId

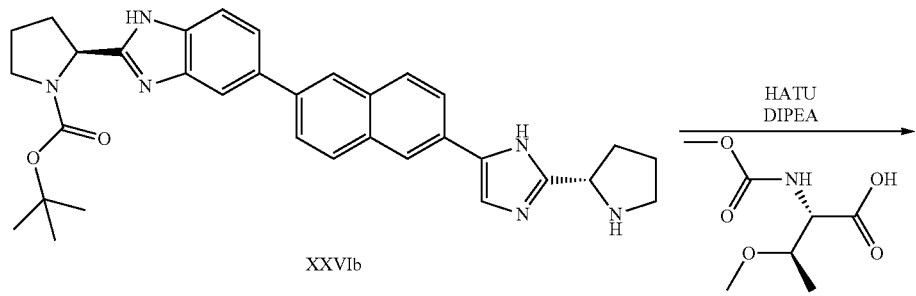

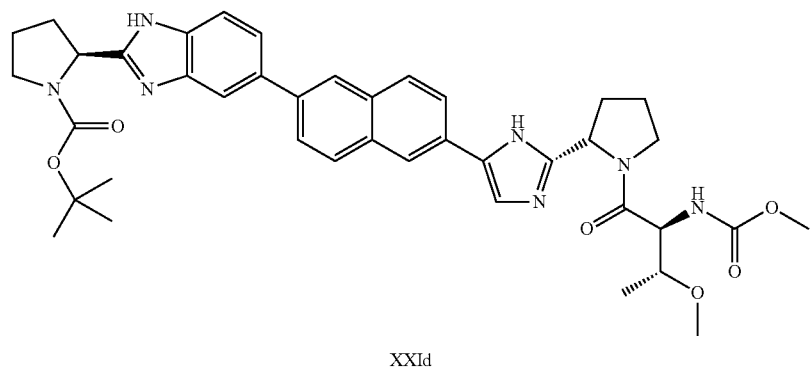

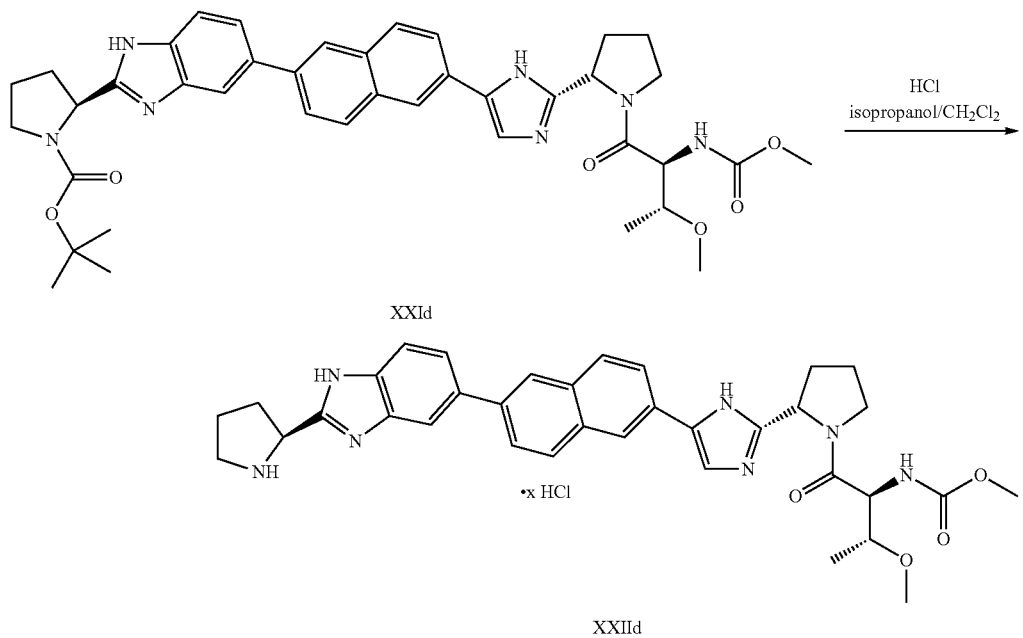

XXId

XXIId

To a solution of XXId (4.38 g, 6.07 mmol) in dichloromethane (40 mL) was added 5-6N HCl in isopropanol (50 mL) and the mixture was stirred at room temperature for 4 hours. tBuOMe (100 mL) was added and the slurry was stirred at room temperature for 30 minutes. The filtered solid was rinced with tBuOMe (50 mL) and to the filtrate was added again tBuOMe (100 mL). New precipitates were formed, filtered and washed with tBuOMe. All precipitates were collected and placed in vacuum oven overnight. Product XXIId was obtained as a white powder (3.61 g) and used as such in next step.

3.3.4.3 Preparation of Compound 18

HATU (1.97 g, 5.189 mmol), DIPEA (4.26 mL, 24.71 mmol) and N-methoxycarbonyl-L-isoleucine (981.8 mg, 5.189 mmol) are dissolved in dry DMF (10 mL) and stirred for 5 minutes at room temperature before XXIId (3.61 g, 4.94 mmol if x HCl equals 3 HCl) was added. After 1 hour at room temperature, concentrated HCl (3 mL) was added and this was stirred for 5 minutes. The reaction was neutralized with $Na_2CO_3$, diluted with dichloromethane (50 mL) and washed with water (2×100 mL). The organic phase was dried over $MgSO_4$, concentrated under reduced pressure and the residue purified by column chromatography (methanol in $CH_2Cl_2$) to yield 18 (2.17 g). $[\alpha]_D^{20}=-139.97°$ (c 0.3558 w/v %, MeOH)

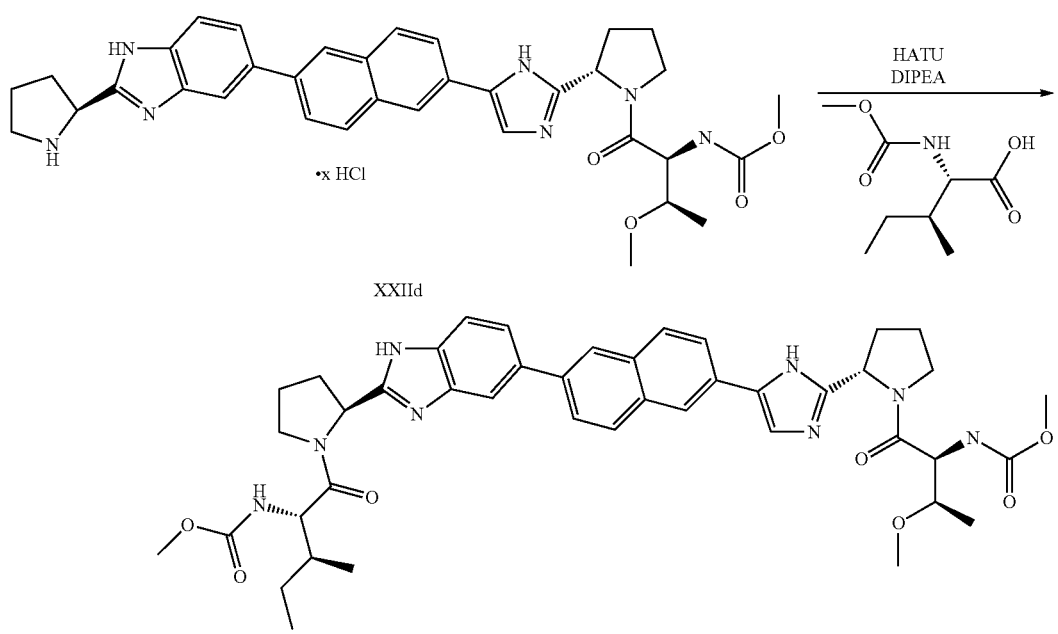

XXIId

18

Preparation of the 0.2 HCl.4H$_2$O Salt of the Compound 18

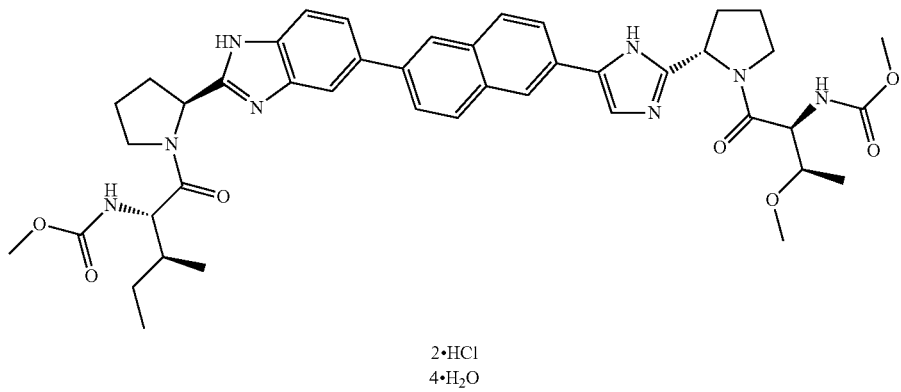 [SMILES: CC[C@H](C)[C@H](NC(=O)OC)C(=O)N1CCC[C@H]1c1nc2cc(-c3ccc4cc(-c5cnc([C@@H]6CCCN6C(=O)[C@@H](NC(=O)OC)[C@@H](C)OC)[nH]5)ccc4c3)ccc2[nH]1]

2·HCl
4·H$_2$O

Compound 18 (485 mg; 0.611 mmol) was dissolved in iPrOH (15 mL, 6N HCl) and the volatiles were removed in vacuum. Acetonitrile (10 mL) was added and the mixture was heated at 40° C. for 10 minutes to afford a sticky precipitate. Water (0.4 mL) was added to afford a colorless solution. Acetonitrile (15 mL) was added dropwise to afford a sticky precipitate. Part of the solution (~5 mL) was evaporated at 40° C. to afford a homogeneous solution. Again, acetonitrile (20 mL) was added and no precipitate was formed. The volatiles were removed in vacuum. The residual water was azeotropically removed by repeated addition and evaporation, at 30° C. under reduced pressure, of acetonitrile (4×40 mL). The obtained powder was stirred in acetonitrile at room temperature in a closed round bottomed flask overnight, filtered and immediately dried under vacuum overnight to afford a slightly yellow powder (365 mg).

The obtained solid was analyzed to have C$_{43}$H$_{52}$N$_8$O$_7$.2 HCl.4H$_2$O by elemental analysis, Anion Ion chromatography and H$_2$O titration Anal. Calcd for C$_{43}$H$_{52}$N$_8$O$_7$.2 HCl.4H$_2$O: C, 55.07; H, 6.66; N, 11.95. Found: C, 54.54; H, 6.54; N, 12.18. Calc.4H$_2$O: 7.68. Found: 7.55; Ion Chromatography (anion) Calc: 2 Cl$^-$ 7.56 Found: 7.36.

$[\alpha]_D^{20}$=−97.53° (c (0.324 w/v %, MeOH)

$^1$H NMR (600 MHz, DIMETHYLFORMAMIDE-d$_7$, 280K) δ ppm 0.84 (t, J=7.3 Hz, 3H), 0.91 (d, J=6.7 Hz, 3H), 1.05-1.14 (m, 1H), 1.15 (d, J=6.2 Hz, 3H), 1.39-1.50 (m, 1H), 1.93-2.02 (m, 1H), 2.04-2.12 (m, 1H), 2.12-2.19 (m, 1H), 2.28-2.37 (m, 1H), 2.40-2.62 (m, 5H), 3.27 (s, 3H), 3.61 (s, 3H), 3.62 (s, 3H), 3.93-4.00 (m, 2 H), 4.00-4.05 (m, 1H), 4.23-4.30 (m, 1H), 4.36 (m, 2H), 4.47 (dd, J=8.8, 4.7 Hz, 1H), 5.46 (t, J=7.6 Hz, 1H), 5.51 (dd, J=7.9, 5.6 Hz, 1H), 6.97 (d, J=8.5 Hz, 1H), 7.33 (d, J=8.8 Hz, 1H), 7.99 (d, J=8.5 Hz, 1H), 8.01-8.03 (m, 2H), 8.09 (d, J=8.5 Hz, 1H), 8.19 (d, J=8.5 Hz, 1H), 8.22 (dd, J=8.5, 1.5 Hz, 1H), 8.26 (s, 1H), 8.32 (s, 1H), 8.41 (s, 1H), 8.90 (s, 1H)

3.4 Preparation of Compounds 5 to 8, 10, 12, 14, 15, 19, 20, 21

3.4.1 Synthesis of compound 5

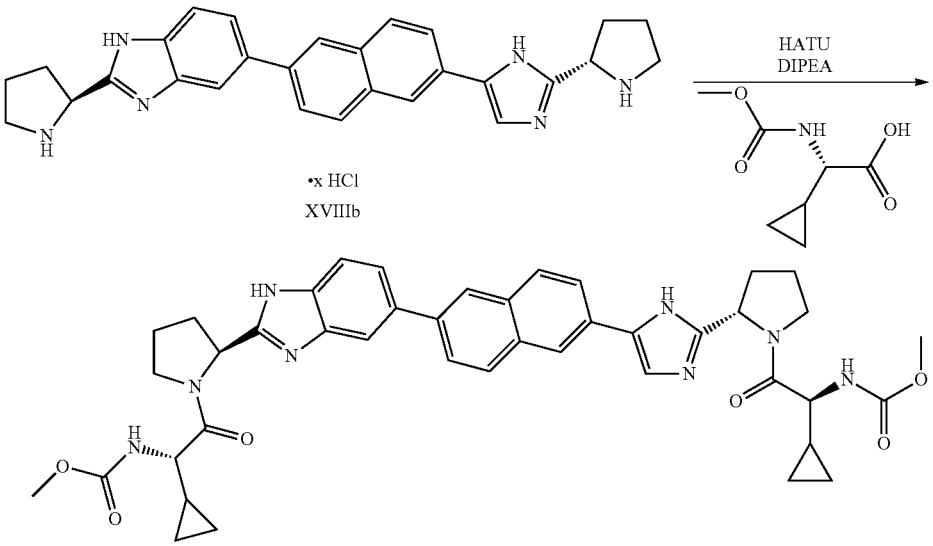

5

HATU (268 mg, 0.71 mmol), DIPEA (0.334 mL, 2 mmol), XVIIIb (200 mg, 0.34 mmol if x HCl equals 4 HCl) and (S)-2-cyclopropyl-2-(methoxycarbonylamino)-acetic acid (145 mg, 0.84 mmol) were mixed together in dry DMF (5 mL). The mixture was stirred for 1 hour at room temperature. $CH_2Cl_2$ was added and the mixture was washed twice with saturated $NaHCO_3$. The organic phase was dried with $MgSO_4$ and after filtration, the solvent was removed in vacuum. The mixture was purified by silicagel column chromatography (gradient elution with 0-5% MeOH in $CH_2Cl_2$) to yield compound 5 (100 mg, 38%).

3.4.2 Synthesis of Compounds 6 to 8, 10, 12, 14, 15, 19, 20, 21

Compound 6 can be synthesized following the procedure reported for compound 5 using (2S,3R)-3-hydroxy-2-(methoxycarbonylamino)butanoic acid instead of (S)-2-cyclopropyl-2-(methoxycarbonylamino)acetic acid.

Compound 7 can be synthesized following the procedure reported for compound 5 using (S)-2-(methoxycarbonylamino)-4-methylpentanoic acid instead of (S)-2-cyclopropyl-2-(methoxycarbonylamino)acetic acid.

Compound 8 can be synthesized following the procedure reported for compound 5 using (2S,3S)-2-(methoxycarbonylamino)-3-methylpentanoic acid instead of (S)-2-cyclopropyl-2-(methoxycarbonylamino)acetic acid.

$^1$H NMR (400 MHz, MeOD) δ ppm 0.82-0.94 (m, 12H), 1.04-1.28 (m, 2H), 1.41-1.62 (m, 2H), 1.72-1.86 (m, 2H), 2.12-2.45 (m, 6H), 2.53-2.73 (m, 2H), 3.66 (s, 6H), 3.82-4.00 (m, 2H), 4.13-4.23 (m, 2H), 4.24-4.31 (m, 2H), 5.25-5.31 (m, 1H), 5.34-5.41 (m, 1H), 7.84-7.91 (m, 2H), 7.94-8.05 (m, 3H), 8.07-8.17 (m, 3H), 8.25-8.33 (m, 2H)

Compound 10 can be synthesized following the procedure reported for compound 5 using (S)-4-methoxy-2-(methoxycarbonylamino)butanoic acid instead of (S)-2-cyclopropyl-2-(methoxycarbonylamino)acetic acid.

Compound 12 can be synthesized following the procedure reported for compound 5 using 2-(methoxycarbonylamino)-2-(tetrahydro-2H-pyran-4-yl)acetic acid instead of (S)-2-cyclopropyl-2-(methoxycarbonylamino)acetic acid.

Compound 14 can be synthesized following the procedure reported for compound 5 using (R)-2-(methoxycarbonylamino)-2-phenylacetic acid instead of (S)-2-cyclopropyl-2-(methoxycarbonylamino)acetic acid.

Compound 15 can be synthesized following the procedure reported for compound 5 using (S)-2-cyclopentyl-2-(methoxycarbonylamino)acetic acid instead of (S)-2-cyclopropyl-2-(methoxycarbonylamino)acetic acid.

Compound 19 can be synthesized following the procedure reported for compound 5 using (2S,3R)-2-(methoxycarbonylamino)-3-methylpentanoic acid instead of (S)-2-cyclopropyl-2-(methoxycarbonylamino)acetic acid.

Compound 20 and 21 can be synthesized according to procedures similar to those exemplified in the synthesis of compound 17 and 18 respectively, with the exception that the corresponding intermediate (S,R)-XXVc is synthesized starting from compound (S)-IIIa and (R)-VIIIc in contrast with the synthesis of (S,S)-XXVc from (S)-IIIa and (S)-VIIIc. (R)-VIIIc can be prepared as exemplified for (S)-VIIIc by using CBz-D-Proline instead of CBz-L-Proline.

All compounds were characterized by LC/MS.

Method A:

Liquid Chromatography: Waters Alliance 2695, UV detector: Waters 996 PDA, range: 210-400 nm; Mass detector: Waters ZQ, ion source: ES+, ES− Column used: SunFire C18 3.5µ 4.6×100 mm mobile phase A: 10 mM $NH_4OOCH$+ 0.1% HCOOH in $H_2O$; mobile phase B: $CH_3OH$; column temp.: 50° C.; flow: 1.5 mL/min Gradient time(min) [% A % B]0 [65/35] to 7[5/95] to 9.6[5/95] to 9.8[65/35] to 12 [65/35]

Method B:

Waters Acquity UPLC equipped with a PDA detector (range 210-400 nm) and a Waters SQD with a dual mode ion source ES+/−. The column used was a Halo C18, 2.7µ, 2.1×50 mm, and held at 50° C. A gradient of 95% aqueous formic acid (0.1%)/5% acetonitrile to 100% acetonitrile was ramped over 1.5 minutes, held for 0.6 minutes, then returns to 100% aqueous formic acid (0.1%) for 0.5 minutes. The flow rate was 0.6 mL/min.

TABLE 1a compounds of formula I

| Comp nr. | Z | Z' | A | Exact Mass | Observed Mass (M + H) | Rt (Min.) | Method |
|---|---|---|---|---|---|---|---|
| 2 | (methoxycarbonylamino threonine methyl ester) | (methoxycarbonylamino threonine methyl ester) | phenyl | 744.4 | 745.4 | 3.5 | A |

TABLE 1a-continued compounds of formula I

| Comp nr. | Z | Z' | A | Exact Mass | Observed Mass (M + H) | Rt (Min.) | Method |
|---|---|---|---|---|---|---|---|
| 3 | methyl carbamate-Val | methyl carbamate-Val | 2,6-naphthalene | 762.4 | 763.8 | 0.8 | B |
| 4 | methyl carbamate-O-methyl-Thr | methyl carbamate-O-methyl-Thr | 2,6-naphthalene | 794.4 | 795.8 | 0.75 | B |
| 5 | methyl carbamate-cyclopropylglycine | methyl carbamate-cyclopropylglycine | 2,6-naphthalene | 758.3 | 759.3 | 4.69 | A |
| 6 | methyl carbamate-Thr | methyl carbamate-Thr | 2,6-quinoline | 766.3 | 767.2 | 3.80 | A |
| 7 | methyl carbamate-Leu | methyl carbamate-Leu | 2,6-naphthalene | 790.4 | 791.3 | 6.04 | A |

TABLE 1a-continued compounds of formula I

| Comp nr. | Z | Z' | A | Exact Mass | Observed Mass (M + H) | Rt (Min.) | Method |
|---|---|---|---|---|---|---|---|
| 8 | | | naphthalene-2,6-diyl | 790.4 | 791.3 | 5.94 | A |
| 9 | | | naphthalene-2,6-diyl | 778.3 | 779.3 | 4.93 | A |
| 10 | | | naphthalene-2,6-diyl | 794.4 | 795.3 | 4.45 | A |
| 11 | | | naphthalene-2,6-diyl | 778.3 | 779.3 | 4.97 | A |
| 12 | | | naphthalene-2,6-diyl | 846.4 | 847.4 | 4.44, 4.52 | A |

TABLE 1a-continued
compounds of formula I
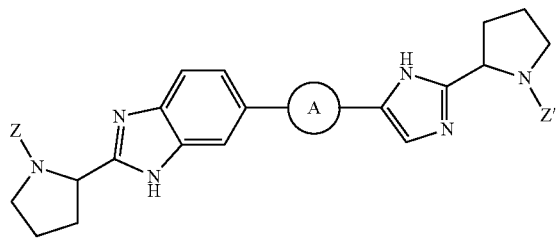
| Comp nr. | Z | Z' | ⸺A⸺ | Exact Mass | Observed Mass (M + H) | Rt (Min.) | Method |
|---|---|---|---|---|---|---|---|
| 13 | | | naphthalene-2,6-diyl | 776.4 | 777.4 | 5.57 | A |
| 14 | | | naphthalene-2,6-diyl | 830.3 | 831.6 | 0.9 | B |
| 15 | | | naphthalene-2,6-diyl | 814.4 | 815.4 | 6.14 | A |
| 16 | | | naphthalene-2,6-diyl | 776.4 | 777.3 | 5.59 | A |

TABLE 1a-continued compounds of formula I

| Comp nr. | Z | Z' | A | Exact Mass | Observed Mass (M + H) | Rt (Min.) | Method |
|---|---|---|---|---|---|---|---|
| 17 | | | | 792.4 | 793.3 | 5.31 | A |
| 18 | | | | 792.4 | 793.2 | 5.37 | A |
| 19 | | | | 790.4 | 791.3 | 5.93 | A |

The stereogenic carbon atom adjacent to the nitrogen of the pyrrolidine ring attached to the benzimidazole group has for all compounds in this Table 1a an "S" configuration.
The stereogenic carbon atom adjacent to the nitrogen of the pyrrolidine ring attached to the imidazole group has for all compounds in this Table 1a an "S" configuration.

In tables 1a and 1b, "*" in Z and Z' denotes the point of attachment. For instance for compound 2 in this Table 1a, Z being 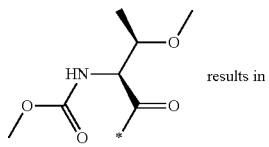 results in

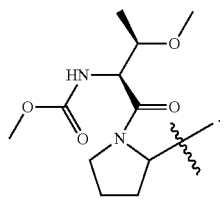

TABLE 1b further compounds of formula I

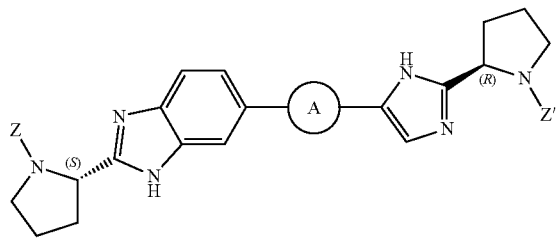

| Comp nr. | Z (* denotes point of attachment) | Z' (* denotes point of attachment) | —A— | Exact Mass | Observed Mass (M + H) | Rt (Min.) | Method |
|---|---|---|---|---|---|---|---|
| 20 | | | | 792.4 | 793.4 | 5.43 | A |
| 21 | | | | 792.4 | 793.4 | 5.49 | A |

Example 4

Anti-HCV Activity of Compounds of Formula I

Replicon Assay

The compounds of formula (I) were examined for inhibitory activity in the HCV replicon. This cellular assay is based on a bicistronic expression construct, as described by Lohmann et al. (Science (1999) 285: 110-113; Journal of Virology (2003) 77: 3007-3019) with modifications described by Krieger et al. (Journal of Virology (2001) 75: 4614-4624), and Lohmann et al. (Journal of Virology (2003) 77: 3007-3019) for genotype 1b and by Yi et al. (Journal of Virology (2004) 78: 7904-7915) for genotype 1a, in a multi-target screening strategy.

Stable Transfection

The method was as follows. The assay utilized the stably transfected cell line Huh-7 luc/neo (hereafter referred to as Huh-Luc). This cell line harbors an RNA encoding a bicistronic expression construct comprising the wild type NS3-NS5B regions of HCV type 1b translated from an Internal Ribosome Entry Site (IRES) from encephalomyocarditis virus (EMCV), preceded by a reporter portion (FfL-luciferase), and a selectable marker portion (neoR, neomycine phosphotransferase). The construct is flanked by 5' and 3' NTRs (non-translated regions) from HCV type 1b. Continued culture of the replicon cells in the presence of G418 (neoR) is dependent on the replication of the HCV RNA. The stably transfected replicon cells that replicate HCV RNA autonomously and to high levels, encoding inter alia luciferase, were used for screening the antiviral compounds.

The replicon cells were plated in 384 well plates in the presence of the test and control compounds which were added in various concentrations. Following an incubation of three days, HCV replication was measured by assaying luciferase activity (using standard luciferase assay substrates and reagents and a Perkin Elmer ViewLux™ ultraHTS microplate imager). Replicon cells in the control cultures have high luciferase expression in the absence of any inhibitor. The inhibitory activity of the compound was monitored on the Huh-Luc cells, enabling a dose-response curve for each test compound. $EC_{50}$ values were then calculated, which represent the amount of compound required to decrease the level of detected luciferase activity by 50%, or more specifically, to reduce the ability of the genetically linked HCV replicon RNA to replicate. Table 2 shows the replicon results obtained for compounds of the examples given above in the stably transfected cell lines ($EC_{50}$ 1b (stable)).

Where a compound of formula (I) was tested more than once in the replicon assay, the average of all test results is given in this Table 2.

TABLE 2

| STRUCTURE | Compound nr. | EC$_{50}$ 1b (stable) (nM) |
|---|---|---|
| 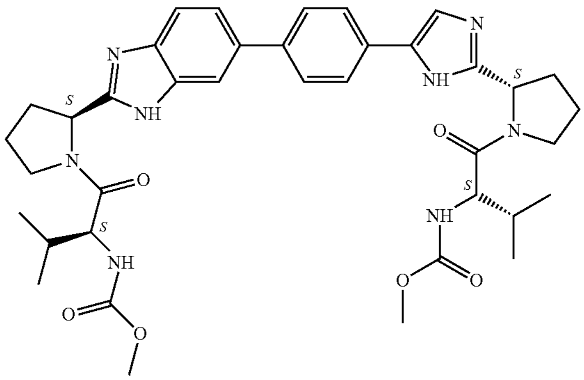 | 1 | 0.058 |
| 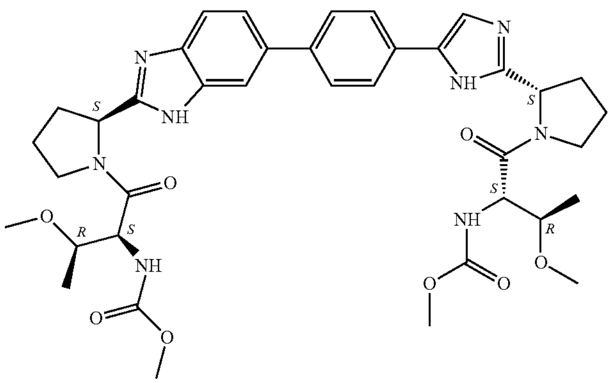 | 2 | 0.54 |
| 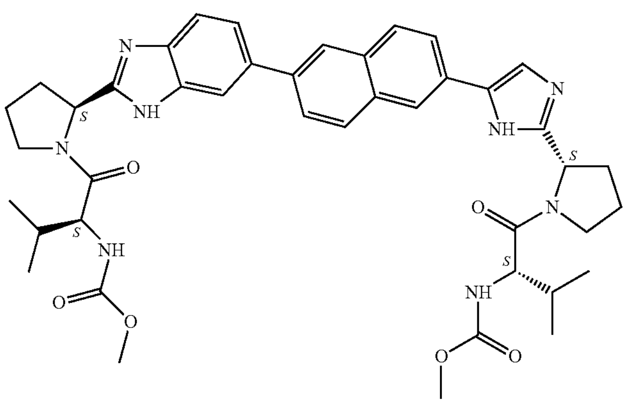 | 3 | 0.007 |
| 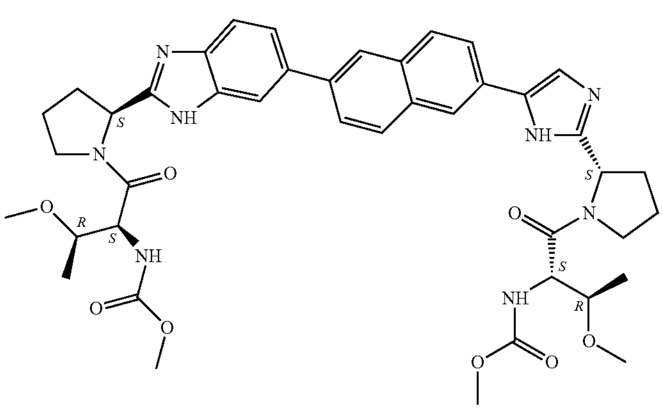 | 4 | 0.012 |

TABLE 2-continued

| STRUCTURE | Compound nr. | EC$_{50}$ 1b (stable) (nM) |
|---|---|---|
| 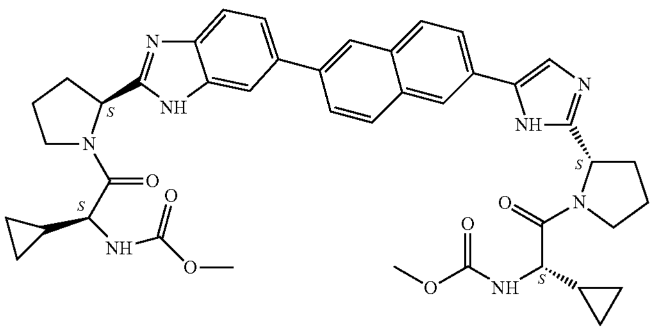 | 5 | 0.039 |
| 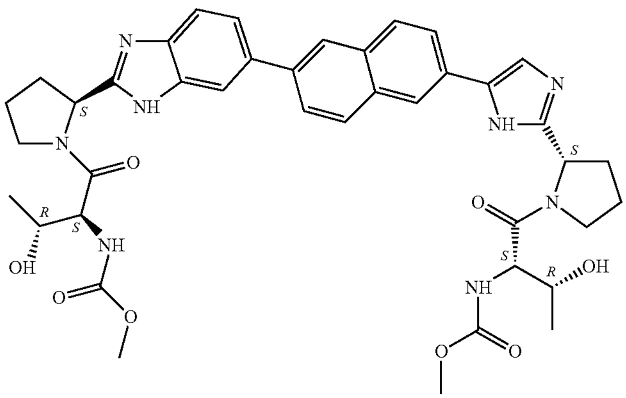 | 6 | 0.132 |
| 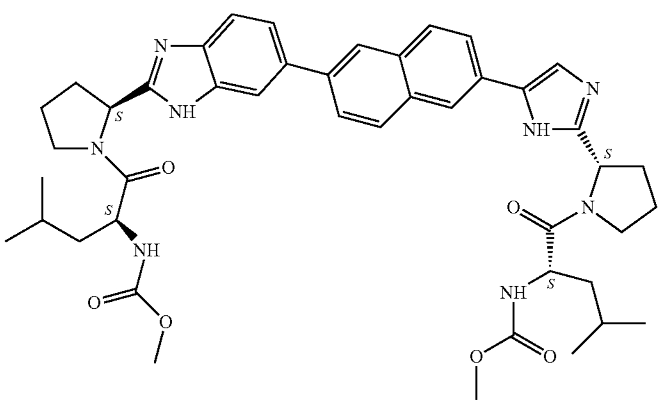 | 7 | 0.005 |
| 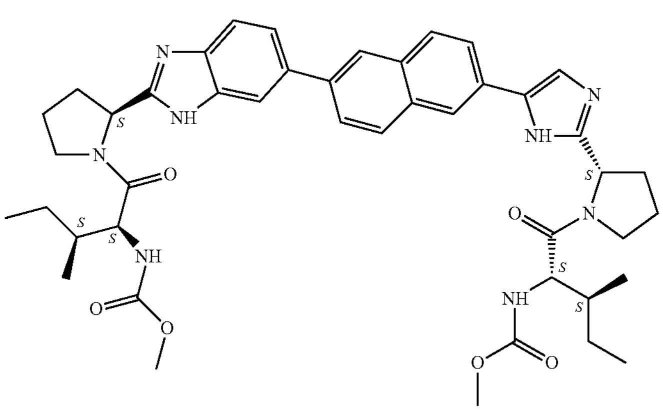 | 8 | 0.003 |

TABLE 2-continued

| STRUCTURE | Compound nr. | EC$_{50}$ 1b (stable) (nM) |
|---|---|---|
| 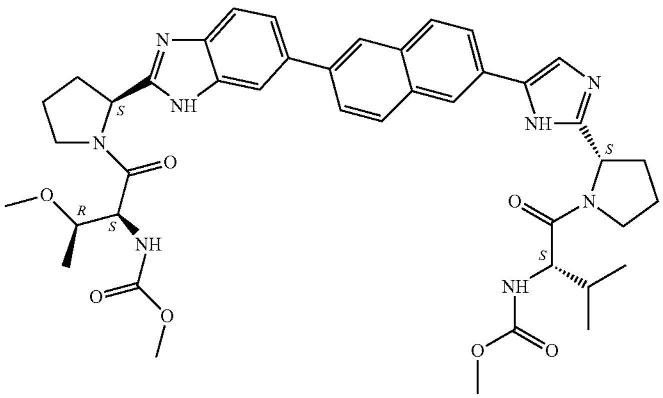 | 9 | 0.007 |
| 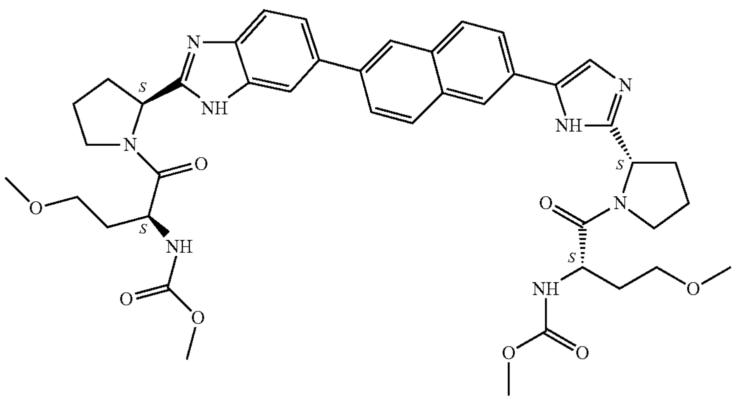 | 10 | 0.029 |
| 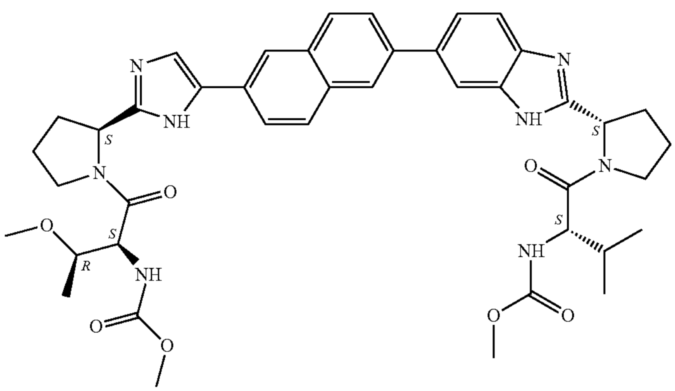 | 11 | 0.006 |
| 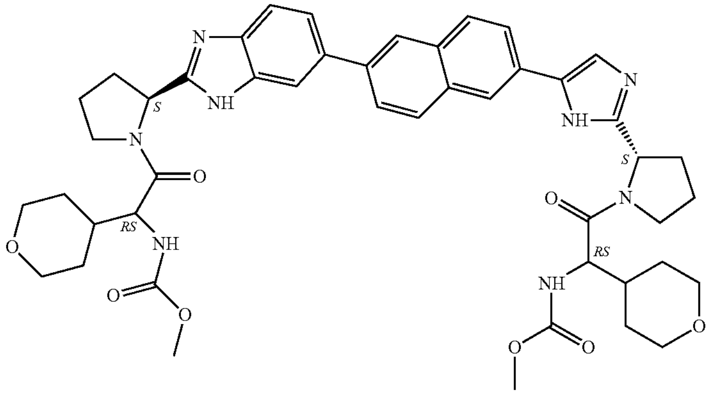 | 12 | 0.080 |

TABLE 2-continued

| STRUCTURE | Compound nr. | EC$_{50}$ 1b (stable) (nM) |
|---|---|---|
| 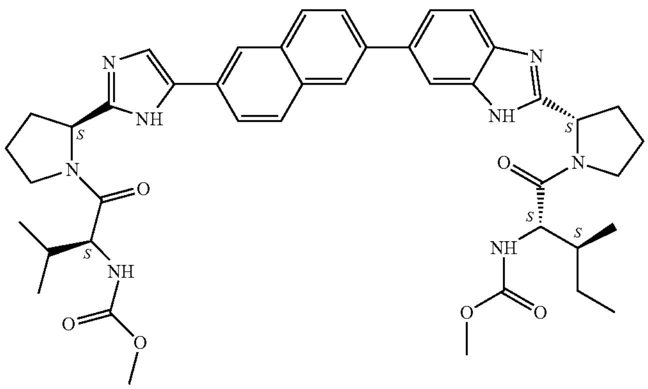 | 13 | 0.002 |
| 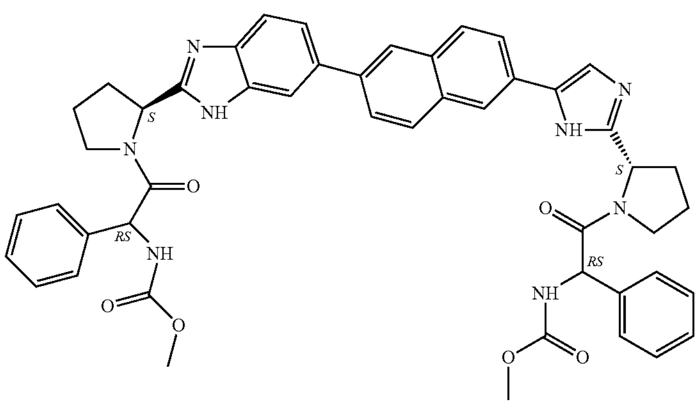 | 14 | 0.004 |
| 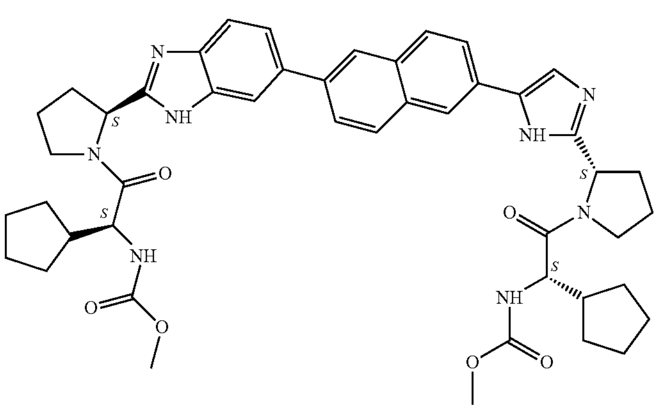 | 15 | 0.003 |

TABLE 2-continued

| STRUCTURE | Compound nr. | EC$_{50}$ 1b (stable) (nM) |
|---|---|---|
| 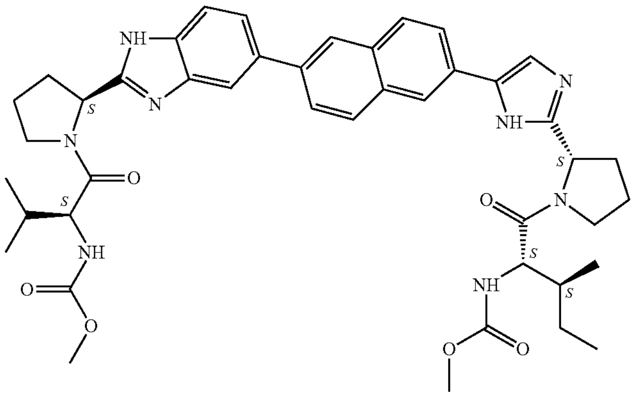 | 16 | 0.003 |
| 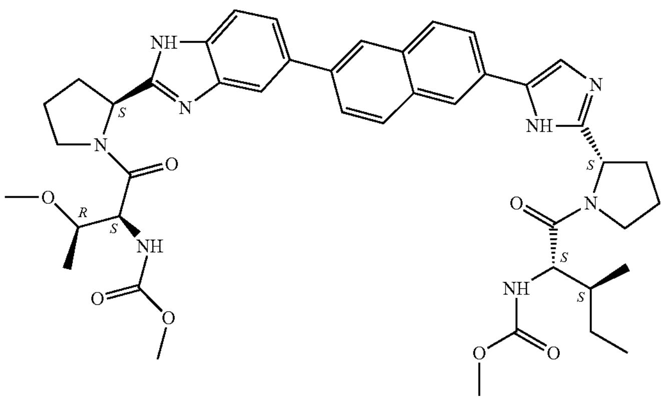 | 17 | 0.005 |
| 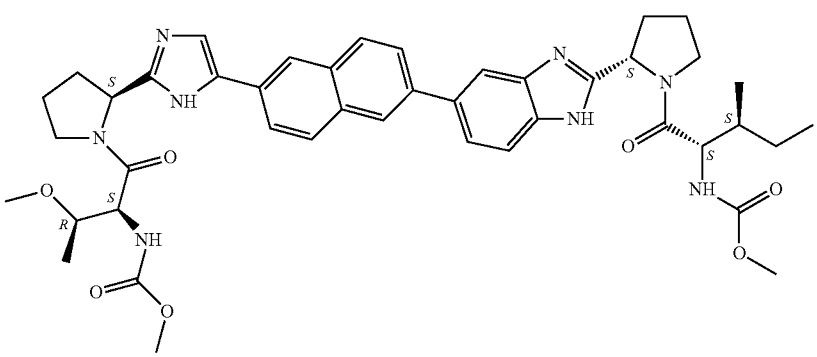 | 18 | 0.003 |
| 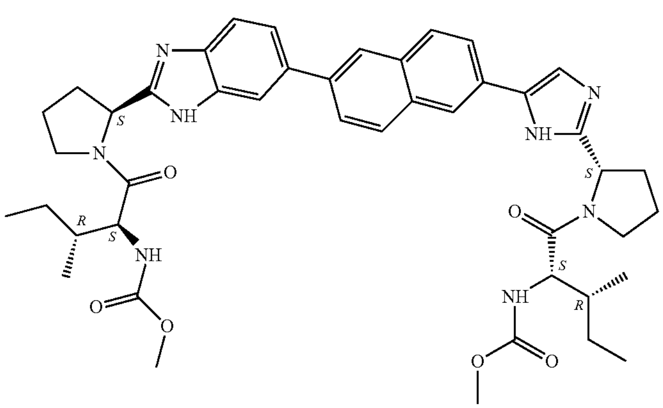 | 19 | 0.003 |

TABLE 2-continued

| STRUCTURE | Compound nr. | $EC_{50}$ 1b (stable) (nM) |
|---|---|---|
| 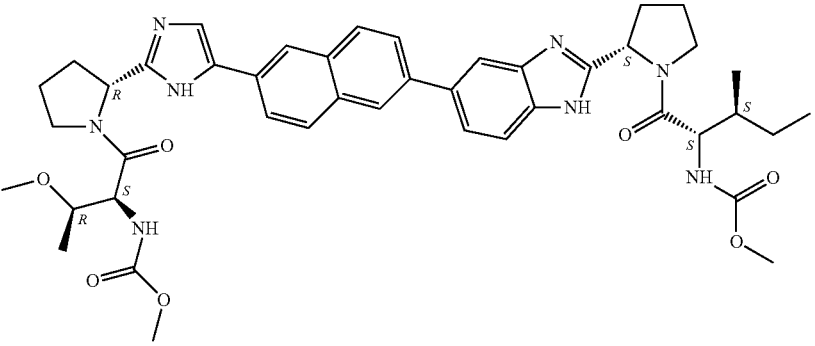 | 20 | 2.3 |
| 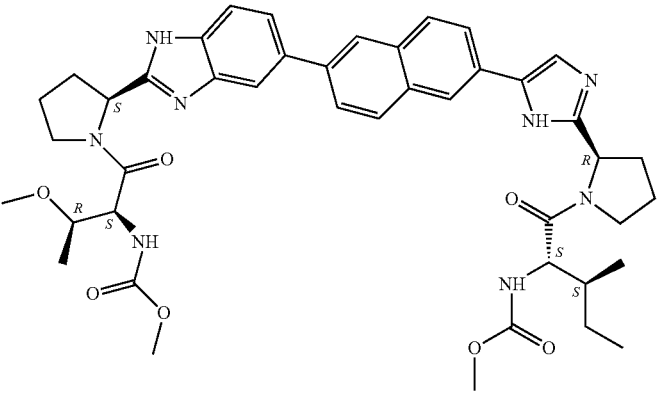 | 21 | 2.2 |

Transient Transfection

In a transient set-up, a Huh-7 lunet hepatoma cell line was transiently transfected with an autonomously replicating RNA encoding a bi-cistronic expression construct. This construct comprises a firefly luciferase reporter gene preceding the NS3-NS5B subgenomic region of HCV (genotype 1a H77 or 1b Con1). Translation of the HCV subgenomic region is mediated by an internal ribosome entry site of encephalomyocarditis virus. The construct is furthermore flanked by 5' and 3' untranslated regions of HCV (genotype 1a H77 or 1b Con 1, respectively), which allow for replication of the RNA.

In addition to the wild-type constructs, site-directed mutations were introduced into the transient HCV genotype 1b replicon in the gene encoding for the non-structural protein 5A (NS5A). More precisely, amino acid residues 28, 30, 31 and 93 in NS5A were independently altered.

Cells were plated in 384 well plates in the presence of test and control compounds, which were added in various concentrations. Following an incubation of two days, replication of the HCV subgenomic replicon RNA was measured by assaying luciferase activity (using standard luciferase assay substrates and reagents and a Perkin Elmer ViewLux™ ultraHTS microplate imager). HCV subgenomic replicon containing cells in the control cultures have high luciferase expression in the absence of any inhibitor. The inhibitory activity of the compound was monitored, enabling a dose-response curve for each test compound. $EC_{50}$ values were then calculated, which represent the amount of compound required to decrease the level of detected luciferase activity by 50%, or more specifically, to reduce the ability of the genetically linked HCV subgenomic RNA to replicate.

Table 3 shows the replicon results obtained for compounds of the examples given above in the transiently transfected cell lines for the 1a and 1b genotype ($EC_{50}$ 1a (transient), and, $EC_{50}$ 1b (transient) respectively). Table 4 shows the replicon results on the NS5A mutants in 1b obtained for compounds of the examples given above in the transiently transfected cell lines also as $EC_{50}$ values.

Counterscreens

Counterscreen cell lines included a Huh-7 hepatoma cell line containing a human cytomegalovirus major immediate-early promoter-Luc construct (Huh7-CMV-Luc) and an MT4 T-cell line containing a long terminal repeat-Luc reporter (MT4-LTR-Luc). Table 3 shows the counterscreen results obtained for compounds of the examples given above.

Where a compound of formula (I) was tested more than once in the transient replicon assay, the average of all test results is given in Table 3.

TABLE 3

| Compound number | $EC_{50}$ 1b (transient) (nM) | $EC_{50}$ 1a (transient) (nM) | $CC_{50}$ MT4-LTR-luc (μM) | $CC_{50}$ Huh7-CMV-luc (μM) |
|---|---|---|---|---|
| 1 | 0.058 | | >0.984 | |
| 2 | 0.909 | | >0.984 | >0.984 |
| 3 | 0.008 | 0.051 | 5.822 | 7.643 |
| 4 | 0.016 | 0.033 | >0.984 | >0.984 |
| 5 | 0.058 | | >0.984 | >0.984 |

TABLE 3-continued

| Compound number | EC$_{50}$ 1b (transient) (nM) | EC$_{50}$ 1a (transient) (nM) | CC$_{50}$ MT4-LTR-luc (μM) | CC$_{50}$ Huh7-CMV-luc (μM) |
|---|---|---|---|---|
| 6 | 0.142 | 0.181 | >0.984 | >0.984 |
| 7 | 0.003 | 0.989 | >0.984 | >0.984 |
| 8 | 0.005 | 0.204 | >0.984 | >0.984 |
| 9 | 0.007 | 0.030 | >0.984 | >0.984 |
| 10 | 0.057 |  | >0.984 | >0.984 |
| 11 | 0.012 | 0.048 | >0.984 | >0.984 |
| 12 | 0.110 | 0.268 | >0.984 | >0.984 |
| 13 | 0.002 | 0.051 | >0.984 | >0.984 |
| 14 | 0.004 | 0.836 | >0.984 | >0.984 |
| 15 | 0.003 | 0.277 | >0.984 | >0.984 |
| 16 | 0.003 | 0.098 | >0.984 | >0.984 |
| 17 | 0.005 | 0.049 | 9.305 | 11.10 |
| 18 | 0.004 | 0.018 | 9.678 | 8.684 |
| 19 | 0.002 | 0.471 | >0.984 | >0.984 |
| 20 | 4.103 | 323.504 | 9.413 | 8.165 |
| 21 | 2.898 | 482.403 | 9.144 | 8.163 |

TABLE 4

| Compound number | EC$_{50}$ (nM) | | | | | | |
|---|---|---|---|---|---|---|---|
|  | L28T | R30H | L31F | L31M | L31V | Y93H | Y93C |
| 1 | 4.121 | 0.600 | 0.775 |  | 1.059 | 1.331 | 0.076 |
| 2 | 9.049 | 2.686 | 1.813 |  | 1.378 | 2.882 | 0.655 |
| 3 | 0.229 | 0.072 | 0.032 | 0.184 | 0.504 | 0.470 | 0.012 |
| 4 | 0.052 | 0.056 | 0.020 | 0.052 | 0.048 | 0.034 | 0.013 |
| 5 |  |  |  |  |  | 10.848 |  |
| 6 |  |  |  |  |  | 1.013 |  |
| 7 |  |  |  |  |  | 3.411 |  |
| 8 | 0.206 | 0.116 | 0.016 | 0.258 | 0.311 | 0.587 | <0.013 |
| 9 | 0.081 | 0.045 | <0.017 | 0.072 | 0.086 | 0.042 | <0.013 |
| 10 |  |  |  |  |  | 1.032 |  |
| 11 | 0.117 | 0.050 | 0.021 | 0.087 | 0.141 | 0.167 | <0.013 |
| 12 |  |  |  |  |  | 0.275 |  |
| 13 | 0.109 | 0.027 | <0.013 | 0.053 | 0.141 | 0.215 | <0.013 |
| 14 |  |  |  |  |  | 0.093 |  |
| 15 |  |  |  |  |  | 1.192 |  |
| 16 | 0.151 | 0.070 | 0.017 | 0.093 | 0.411 | 0.343 | <0.013 |
| 17 | 0.037 | 0.036 | 0.005 | 0.025 | 0.037 | 0.034 | 0.003 |
| 18 | 0.041 | 0.039 | 0.005 | 0.054 | 0.052 | 0.080 | 0.003 |
| 19 |  |  |  |  |  | 5.186 |  |
| 20 |  |  |  |  |  | 336 |  |
| 21 |  |  |  |  |  | 275 |  |

Example 5

Pharmacokinetic Analysis after Single Oral Administration I

Compounds were dosed orally as a solution in PEG400 to male Sprague-Dawley rats at a dose level of 10 mg/kg. At serial time points, after dosing, the animals were sacrificed and liver samples collected. All samples were analyzed using a qualified research LC-MS/MS method to determine the concentration of the tested compounds in liver. Non-compartmental analysis using the lin/log trapezoidal rule was performed using WinNonlin™ Professional (Version 5.2.1). The results are summarized in Table 5.

TABLE 5

| Compound number | Liver AUC (ng * h/g) |
|---|---|
| 3 | 23157 |
| 4 | 1539 |
| 8 | 50655 |

TABLE 5-continued

| Compound number | Liver AUC (ng * h/g) |
|---|---|
| 9 | 6202 |
| 11 | 7928 |
| 13 | 51330 |
| 16 | 12630 |
| 17 | 4213 |
| 18 | 14091 |

Example 6

Inhibitor Combination Studies

In certain embodiments, three compounds from table 2 were combined with a compound that inhibits replication of hepatitis C virus, such as, for example, TMC435350, MK-7009, ITMN-191, or a polymerase inhibitor (nucleoside-based inhibitor: compound A and PSI-6130; non-nucleoside-based inhibitor: compound B). The experiment was set-up in a "checkerboard" motif with one drug being titrated horizontally and the other one vertically on Huh7-Luc cells containing the stably transfected HCV 1b replicon. Each two-way combination was performed at least three times and analyzed with the MacSynergy™ II software to obtain the percent synergy/antagonism volumes (expressed as nM$^2$%).

The theoretical calculations of additive interactions in MacSynergy™ II were derived from dose response curves of each individual compound. The calculated additive surface was then subtracted from the experimental surface to obtain a synergy surface. Additive interactions resulted in a horizontal plane at 0%. A peak above the 0% plane indicated synergy, a depression below the 0% plane referred to antagonism. The 95% confidence interval for the experimental dose-response surfaces was calculated to evaluate the statistical significance of the synergy or antagonism.

Volumes obtained by MacSynergy™ II upon combination are mentioned in Table 6. Given that synergy volume ranges for the tested combinations, as derived from the 95% confidence envelope for Bliss independence, span volume ranges determined as synergistic and Bliss independent, the tested combinations were considered to act additive to synergistic. No significant antagonism was observed in any of the tested combinations (Table 6).

Compound A

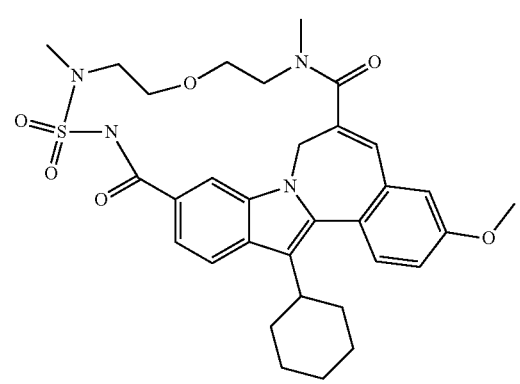 [SMILES: COc1ccc2c(c1)C=C1Cn3c-2c(C2CCCCC2)c2ccc(cc23)C(=O)NS(=O)(=O)N(C)CCOCCN(C)C1=O]

TABLE 6

| Inhibitor class | Compound combination | Synergy volume (95% confidence interval) nM² % | Antagonism volume (95% confidence interval) nM² % |
|---|---|---|---|
| | Compound 3 + | | |
| PI | TMC435350 | 20 (34-5) | −4 (0--7) |
| PI | MK-7009 | 70 (132-7) | −3 (−1--4) |
| PI | ITMN-191 | 58 (112-3) | −4 (−2--6) |
| NI | PSI-6130 | 25 (47-4) | −3 (−1--4) |
| NNI | Compound A | 57 (108-6) | −3 (−1--5) |
| | Compound 17 + | | |
| PI | TMC435350 | 125 (220-29) | −2 (n.s.) |
| PI | MK-7009 | 77 (142-11) | −2 (n.s.) |
| NNI | Compound A | 158 (289-28) | −6 (−1--11) |
| PI | ITMN-191 | not determined | |
| NI | PSI-6130 | not determined | |
| | Compound 18 + | | |
| PI | TMC435350 | 24 (43-5) | −2 (−1--4) |
| PI | MK-7009 | 125 (223-27) | −3 (−1--4) |
| NI | PSI-6130 | 60 (102-18) | −2 (0--4) |
| NNI | Compound A | 37 (53-21) | −11 (−5--18) |
| PI | ITMN-191 | not determined | | n.s. = 'Not Significant' as referred to by MacSynergy™ II

Example 7

Pharmaceutical Compositions

"Active ingredient" as used throughout this example relates to a compound of formula (I), including any stereochemically isomeric form thereof, a pharmaceutically acceptable salt thereof or a solvate thereof; in particular to any one of the exemplified compounds.

Typical examples of formulations of a compound of this invention are as follows:

1. Film-Coated Tablets

Preparation of Tablet Core

A mixture of 100 g of active ingredient, 570 g lactose and 200 g starch is mixed well and thereafter humidified with a solution of 5 g sodium dodecyl sulphate and 10 g polyvinyl-pyrrolidone in about 200 ml of water. The wet powder mixture is sieved, dried and sieved again. Then there is added 100 g microcrystalline cellulose and 15 g hydrogenated vegetable oil. The whole is mixed well and compressed into tablets, giving 10.000 tablets, each comprising 10 mg of active ingredient.

Coating

To a solution of 10 g methyl cellulose in 75 ml of denaturated ethanol there is added a solution of 5 g of ethyl cellulose in 150 ml of dichloromethane. Then there are added 75 ml of dichloromethane and 2.5 ml 1,2,3-propanetriol 10 g of polyethylene glycol is molten and dissolved in 75 ml of dichloromethane. The latter solution is added to the former and then there are added 2.5 g of magnesium octadecanoate, 5 g of polyvinyl-pyrrolidone and 30 ml of concentrated colour suspension and the whole is homogenated. The tablet cores are coated with the thus obtained mixture in a coating apparatus.

2. Suspension

An aqueous suspension is prepared for oral administration so that each milliliter contains 1 to 5 mg of active ingredient, 50 mg of sodium carboxymethyl cellulose, 1 mg of sodium benzoate, 500 mg of sorbitol and water ad 1 ml.

3. Injectable

A parenteral composition is prepared by stirring 1.5% (weight/volume) of active ingredient in 0.9% NaCl solution or in 10% by volume propylene glycol in water.

The invention claimed is:

1. A method of treating HCV infection in a mammal comprising administer to said mammal a composition comprising a compound of Formula I:

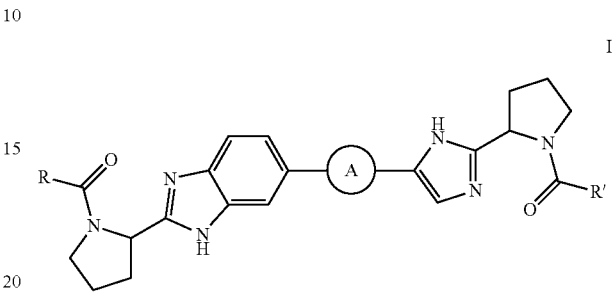

I or a stereoisomeric form thereof, wherein:

A is naphthylene, which is optionally substituted with 1, 2 or 3 substituents selected from halo and $C_{1-3}$alkyl;

R and R' are, each independently, —$CR_1R_2R_3$, aryl, heteroaryl, or heteroC$_{4-6}$cycloalkyl, whereby aryl and heteroaryl may optionally be substituted with 1 or 2 substituents selected from halo and methyl; and wherein $R_1$ is hydrogen;

$C_{1-4}$alkyl optionally substituted with methoxy or dimethylamino;

phenyl optionally substituted with 1, 2 or 3 substituents independently selected from halo, $C_{1-4}$alkoxy, and trifluoromethoxy;

1,3-benzodioxolanyl;

benzyl optionally substituted with 1, 2 or 3 substituents independently selected from halo and methoxy;

$C_{3-6}$cycloalkyl;

heteroaryl;

heteroC$_{4-6}$cycloalkyl; or heteroarylmethyl;

$R_2$ is hydrogen, hydroxyl, amino, mono- or di-$C_{1-4}$alkylamino, $C_{1-4}$alkylcarbonylamino, $C_{1-4}$alkyloxycarbonylamino, $C_{1-4}$alkylaminocarbonylamino, piperidin-1-yl or imidazol-1-yl;

$R_3$ is hydrogen, or $R_1$ and $R_3$ together form a cyclopropyl group;

or $R_2$ and $R_3$ form oxo;

or a pharmaceutically acceptable salt or a solvate thereof; wherein the compound is not

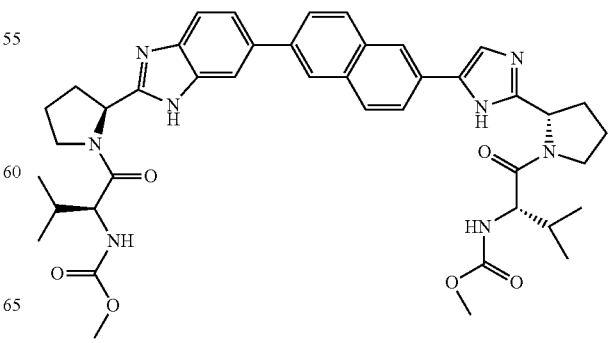

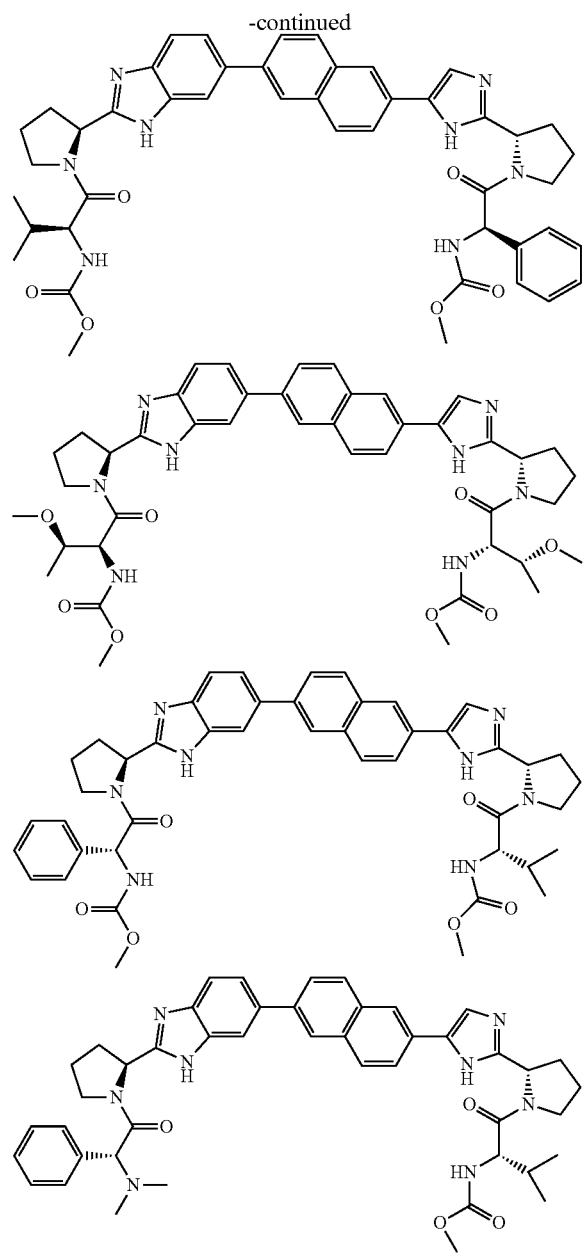

2. The method of claim 1 wherein A is 2,6-naphthylene optionally substituted with 1, 2, or 3 substituents selected from halo and $C_{1-3}$alkyl.

3. The method of claim 1 wherein A is 2,6-napthylene.

4. The method of claim 1 wherein $R_1$ is different from unsubstituted 2-propyl and when $R_1$ in R is 1-methoxyethyl, then $R_1$ in R' is different from 1-methoxyethyl.

5. The method of claim 1 wherein $R_1$ is other than 2 propyl when $R_2$ is methoxycarbonylamino; and $R_1$ in R' is other than 1-methoxyethyl when $R_2$ in R' is methoxycarbonylamino.

6. The method of claim 1 wherein R and R' are different from one another.

7. The method of claim 1 wherein R and R' are the same.

8. The method of claim 1 wherein R and R' each independently are —$CR_1R_2R_3$.

9. The method of claim 1 comprising administering to a mammal a composition comprising (a) a compound of Formula I as defined 1, and (b) another HCV inhibitor, as a combined preparation for simultaneous, separate or sequential use in the treatment of HCV infections.

10. The method of claim 1 comprising administering to a mammal a composition comprising (a) a compound of Formula I as defined by 1, and (b) an immunomodulatory agent, as a combined preparation for simultaneous, separate or sequential use in the treatment of HCV infections.

\* \* \* \* \*

UNITED STATES PATENT AND TRADEMARK OFFICE
CERTIFICATE OF CORRECTION

PATENT NO. : 9,433,609 B2  Page 1 of 1
APPLICATION NO. : 13/836816
DATED : September 6, 2016
INVENTOR(S) : Vandyck et al.

It is certified that error appears in the above-identified patent and that said Letters Patent is hereby corrected as shown below:

In the Claims

Column 114, Line 39 (Claim 9), after "defined" insert --by--

Signed and Sealed this
Seventh Day of February, 2017

Michelle K. Lee
*Director of the United States Patent and Trademark Office*